United States Patent
Ishikawa et al.

(10) Patent No.: US 7,923,462 B2
(45) Date of Patent: Apr. 12, 2011

(54) CATECHOL DERIVATIVE, PHARMACEUTICAL COMPOSITION CONTAINING THE SAME, USE OF THE CATECHOL DERIVATIVE, AND USE OF THE PHARMACEUTICAL COMPOSITION

(75) Inventors: Takehiro Ishikawa, Azumino (JP); Hitoshi Inoue, Azumino (JP); Satoko Kobayashi, Azumino (JP); Masako Yoshida, Azumino (JP); Hiroaki Shiohara, Azumino (JP); Yasunori Ueno, Azumino (JP); Nobuyuki Tanaka, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 12/810,275

(22) PCT Filed: Dec. 22, 2008

(86) PCT No.: PCT/JP2008/073269
§ 371 (c)(1),
(2), (4) Date: Jun. 23, 2010

(87) PCT Pub. No.: WO2009/081891
PCT Pub. Date: Jul. 2, 2009

(65) Prior Publication Data
US 2010/0280083 A1    Nov. 4, 2010

(30) Foreign Application Priority Data
Dec. 25, 2007  (JP) ................. 2007-331896

(51) Int. Cl.
*A61K 31/4245* (2006.01)
*A61K 31/427* (2006.01)
*C07D 271/06* (2006.01)
*C07D 413/04* (2006.01)
*C07D 417/10* (2006.01)
*A61P 25/16* (2006.01)

(52) U.S. Cl. ...................... 514/364; 548/131
(58) Field of Classification Search .................. 514/364; 548/131
See application file for complete search history.

(56) References Cited

U.S. PATENT DOCUMENTS

| 4,871,753 A | 10/1989 | Rohr |
| 5,389,653 A | 2/1995 | Bernauer et al. |

FOREIGN PATENT DOCUMENTS

| JP | 62-240649 A | 10/1987 |
| JP | 63-162680 A | 7/1988 |
| WO | 2007/013830 A1 | 2/2007 |
| WO | 2007/117165 A1 | 10/2007 |

OTHER PUBLICATIONS

Learmonth et al, caplus an 2007:117521.*
D. A. Learmonth, et al., "Synthesis of 1-(3,4-Dihydroxy-5-nitrophenyl)-2-phenyl-ethanone and Derivatives as Potent and Long-Acting Peripheral Inhibitors of Catechol-O-methyltransferase," J. Med. Chem., 2002, pp. 685-695, vol. 45, American Chemical Society.

* cited by examiner

*Primary Examiner* — Sun Jae Y Loewe
(74) *Attorney, Agent, or Firm* — Sughrue Mion, PLLC

(57) ABSTRACT

The present invention provides compounds represented by general formula (I):

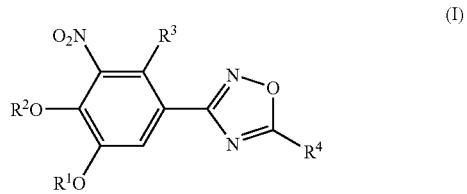

or pharmaceutical acceptable salts thereof, wherein $R^1$ and $R^2$ are each hydrogen, lower acyl, lower alkoxycarbonyl or the like; $R^3$ is halo-lower alkyl, lower acyl, halo-lower alkylcarbonyl, cycloalkylcarbonyl, optionally substituted arylcarbonyl, lower alkoxycarbonyl or the like; $R^4$ is lower alkyl, halo-lower alkyl, cycloalkyl, lower alkoxy-lower alkyl or the like, which exhibit potent COMT inhibitory activities. The present invention also provides pharmaceutical compositions containing said compound, and uses thereof.

10 Claims, No Drawings

US 7,923,462 B2

CATECHOL DERIVATIVE, PHARMACEUTICAL COMPOSITION CONTAINING THE SAME, USE OF THE CATECHOL DERIVATIVE, AND USE OF THE PHARMACEUTICAL COMPOSITION

TECHNICAL FIELD

The present invention relates to novel catechol derivatives, which exhibit catechol-O-methyltransferase inhibitory activities, pharmaceutical compositions containing the same, and their uses.

BACKGROUND ART

Parkinson's disease is a progressive neurodegenerative disease which usually affects elderly patients. The number of parkinsonian patients is growing with progressive aging of society. Parkinson's disease is characterized by impairment in coordinated motor function such as rest tremor, rigidity, akinesia, postural instability and the like. It is thought that Parkinson's disease results from deficiency of dopamine in the striatum, which is caused by degeneration of dopamine neuron in the substantia nigra. For that reasons, L-dopa or dopamine receptor stimulants are used for the treatment of Parkinson's disease.

L-dopa is a precursor of dopamine, and is metabolized to dopamine which exerts its efficacy in the brain. Since L-dopa has a very short serum half-life, L-dopa is administered usually in combination with a peripheral aromatic L-amino acid decarboxylase inhibitor and/or a catechol-O-methyltransferase inhibitor, which inhibit the metabolism of L-dopa in the body. Catechol-O-methyltransferase (thereinafter referred to as "COMT") is an enzyme that catalyze the transfer of the methyl group of S-adenosyl-L-methionine to chatechol substrates. The inhibition of the COMT enzyme slows down the metabolism of L-dopa to 3-O-methyl-L-dopa, which results in the significant increase in serum half-life of L-dopa and the amount of L-dopa crossing the blood-brain-barrier. In this way, a COMT inhibitor, when administered in combination with L-dopa, increases the bioavailability of L-dopa and prolongs its effects (see Non Patent Literature 1).

COMT inhibitors are also expected to be useful for treating or preventing hypertension since COMT inhibitors exhibit urinary sodium excretion promoting activities (see Non Patent Literature 2). COMT inhibitors are also expected to be useful for treating or preventing depression (see Non Patent Literature 3).

A variety of COMT inhibitors have been reported recently. Among them, tolcopone (3,4-dihydroxy-4'-methyl-5-nitro-benzophenone, Patent Literature 1) and entacapone ((E)-2-cyano-N,N-diethyl-3-(3,4-dihydroxy-5-nitrophenyl)acrylamide, Patent Literature 2) are the most potent COMT inhibitors known to date. Tolcapone or entacapone are clinically administered to patients for treating Parkinson's disease. However, it has been reported that tolcapone causes severe liver function damage, and can only be used in parkinsonian patients strictly with regular monitoring of liver function (see Non Patent Literature 4). On the other hand, entacapone has less potent efficacy than tolcapone, and has a problem to have a very limited duration of effect (see Non Patent Literature 5). Accordingly, there is still a need for novel COMT inhibitors with potent COMT inhibitory activities and a desirable safety profile.

Patent Literature 1 discloses 5-(3-methyl-1,2,4-oxadiazol-5-yl)-3-nitropyrocatechol as an [1,2,4]oxadiazole derivative having COMT inhibitory activities (see example 75 in Patent Literature 1). However, the binding position of the 1,2,4-oxadiazole ring to nitro catechol moiety in the compounds of Patent Literature 1 is different from those in compounds of the present invention.

CITATION LIST

Patent Literature

1. Publication of Unexamined Application of European Patent Specification No. 237929
2. Publication of Unexamined Application of British Patent Specification No. 2200109

Non Patent Literature

1. Nutt J. G. et al, "Lancet", 1998, vol. 351, No. 9111, p. 1221-1222
2. Eklof A. C. et al, "Kidney Int.", 1997, vol. 52, No. 3, p. 742-747
3. Moreau J. L. et al, "Behav. Pharmacol.", 1994, vol. 5, No. 3, p. 344-350
4. Benabou R. et al, "Expert Opin. Drug Saf.", 2003, vol. 2, No. 3, p. 263-267
5. Forsberg M. et al, "J. Pharmacol. Exp. Ther.", 2003, vol. 304, No. 2, p. 498-506
6. Koga K. et al, "Eur. J. Pharmacol.", 2000, vol. 408, p. 249-255

DISCLOSURE OF THE INVENTION

An object of the present invention is to provide a novel compound having potent COMT inhibitory activities, and more preferably possessing a desirable safety profile.

The inventors of the present invention diligently worked to achieve the foregoing object and found that catechol derivatives represented by general formula (I) show excellent COMT inhibitory activities and possess high safety. Based on these findings, the present invention has been accomplished.

The present invention therefore provides a compound represented by general formula (I):

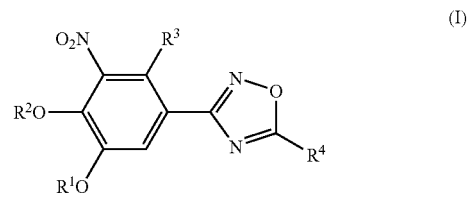

or a pharmaceutically acceptable salt thereof,
wherein
$R^1$ and $R^2$ are each independently a hydrogen atom, a lower acyl group, a lower alkoxycarbonyl group, an aralkylcarbonyl group or —C(O)NR$^{11}$R$^{12}$, or $R^1$ and $R^2$ are joined together to form —C(O)— or a lower alkylene group;
$R^3$ is:
a) a halo-lower alkyl group,
b) a lower acyl group,
c) a halo-lower alkylcarbonyl group,
d) a cycloalkylcarbonyl group,
e) an arylcarbonyl group, wherein the ring of the arylcarbonyl group is unsubstituted or substituted with 1 to 5 substituents selected from the group consisting of a halogen atom, a lower alkyl group, a halo-lower alkyl group, a lower alkoxy group, a cycloalkyl-lower alkoxy group, a hydroxy group, a lower alkoxycarbonyl group, —C(O)NR$^{11}$R$^{12}$ and a cyano group, f) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group, g) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group, h) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group, i) a lower alkoxycarbonyl group,
    j) a cycloalkyloxycarbonyl group,
    k) a lower alkoxy-lower alkoxycarbonyl group,
    l) a carboxy group,
    m) a cyano group,
    n) —C(O)NR$^{11}$R$^{12}$,
    o) —C(O)C(O)NR$^{11}$R$^{12}$,
    p) a lower alkylsulfonyl group,
    q) —SO$_2$NR$^{11}$R$^{12}$ or
    r) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group;

R$^4$ is:
    a) a lower alkyl group,
    b) a halo-lower alkyl group,
    c) a cycloalkyl group,
    d) a heterocycloalkyl group,
    e) a lower alkoxy-lower alkyl group,
    f) an aryloxy-lower alkyl group,
    g) a lower alkoxycarbonyl-lower alkyl group or
    h) a hydroxy-lower alkyl group; and R$^{11}$ and R$^{12}$ are each independently a hydrogen atom, a lower alkyl group, a cycloalkyl group, a bridged cyclic hydrocarbon group, a phenyl group or an aralkyl group, or R$^{11}$ and R$^{12}$, together with the nitrogen atom to which they are bonded, form a cyclic amino group.

In another aspect, the present invention provides a pharmaceutical composition which comprises, as an active ingredient, a compound of general formula (I) or a pharmaceutically acceptable salt thereof.

In still another aspect, the present invention provides a catechol-O-methyltransferase inhibitor which comprises, as an active ingredient, a compound of general formula (I) or a pharmaceutically acceptable salt thereof.

In still another aspect, the present invention provides a pharmaceutical combination which comprises a compound of general formula (I) or a pharmaceutically acceptable salt thereof and at least one selected from L-dopa or an aromatic L-amino acid decarboxylase inhibitor.

In still another aspect, the present invention provides a therapeutic or prophylactic agent for Parkinson's disease, depression or hypertension, which comprises, as an active ingredient, a compound of general formula (I) or a pharmaceutically acceptable salt thereof.

In still another aspect, the present invention provides a use of a compound represented by general formula (I) or a pharmaceutically acceptable salt thereof for the manufacture of a medicament for treating or preventing Parkinson's disease, depression or hypertension.

In still another aspect, the present invention provides a method for treating or preventing Parkinson's disease, depression or hypertension, which comprises administering an effective amount of a compound represented by general formula (I) or a pharmaceutically acceptable salt thereof.

The invention is described using the terms defined below unless otherwise specified.

The term "lower" herein denotes residues with 1 to 6 carbon atoms unless otherwise specified.

The term "halogen atom" refers to a fluorine, chlorine, bromine or iodine atom.

The term "lower alkyl group" refers to a straight chained or branched $C_{1-6}$ alkyl group such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl group and the like. Preferred lower alkyl groups for R$^4$, R$^{11}$ and R$^{12}$ are a $C_{1-4}$ alkyl group, and more preferably a methyl group.

The term "halo-lower alkyl group" refers to a $C_{1-6}$ alkyl group substituted with the same or different 1 to 3 halogen atoms such as a fluoromethyl, difluoromethyl, trifluoromethyl, 2,2,2-trifluoroethyl group and the like, preferably a difluoromethyl or trifluoromethyl group.

The term "hydroxy-lower alkyl group" refers to a hydroxy-$C_{1-6}$ alkyl group such as a hydroxymethyl, 1-hydroxyethyl, 1-hydroxy-1,1-dimethylmethyl, 2-hydroxyethyl, 2-hydroxy-2-methylpropyl, 3-hydroxypropyl group and the like.

The term "lower alkoxy group" refers to a straight chained or branched $C_{1-6}$ alkoxy group such as a methoxy, ethoxy, propoxy, isopropoxy, butoxy isobutoxy, sec-butoxy, tert-butoxy, pentyloxy, hexyloxy group and the like.

The term "cycloalkyl group" refers to a 3- to 7-membered saturated cyclic hydrocarbon such as a cyclopropyl, cyclobutyl, cyclopentyl, cyclohexyl and cycloheptyl group.

The term "heterocycloalkyl group" refers to a 4- to 7-membered saturated heterocyclic group which contains —NH—, —O— or —S— as a member of the ring and is bonded via a carbon atom. Examples of heterocycloalkyl groups include a tetrahydrofuryl, tetrahydrothienyl, tetrahydropyranyl, pyrrolidin-2-yl, pyrrolidin-3-yl, piperidin-2-yl, piperidin-3-yl, piperidin-4-yl group and the like.

The term "bridged cyclic hydrocarbon group" refers to a 5- to 7-membered bridged saturated cyclic hydrocarbon having 7 to 10 carbon atoms such as a bicyclo[2.2.1]heptan-2-yl, adamantan-1-yl group and the like.

The term "aryl group" refers to a $C_{6-10}$ aromatic hydrocarbon group such as a phenyl, 1-naphtyl and 2-naphthyl group, preferably a phenyl group.

The term "aralkyl group" refers to an aryl-$C_{1-6}$ alkyl group such as a benzyl, phenethyl, 1-phenylethyl, 3-phenylpropyl, 4-phenylbutyl, naphthylmethyl group and the like.

The term "cycloalyl-lower alkoxy group" refers to a cycloalkyl-$C_{1-6}$ alkoxy group such as a cyclopropylmethoxy, cyclopentylmethoxy, cyclohexylmethoxy group and the like.

The term "heteroaryl group" refers to a 5- or 6-membered monocyclic aromatic heterocycle having 1 to 5 carbon atoms and to 4 heteroatoms selected independently from the group consisting of an oxygen, nitrogen and sulfur atom, or a 8- to 10-membered bicyclic aromatic heterocycle having 1 to 9 carbon atoms and 1 to 4 heteroatoms selected independently from the group consisting of an oxygen, nitrogen and sulfur atom, provided that said heterocycles do not include adjacent oxygen and/or sulfur atoms. Examples of monocyclic heteroaryl groups include pyrrolyl, furyl, thienyl, imidazolyl, pyrazolyl, oxazolyl, isoxazolyl, 1,2,4-oxadiazolyl, tetrazolyl, triazolyl, isothiazolyl, 1,2,3-thiadiazolyl, triazolyl, pyridyl, pyrazinyl, pyrimidyl and pyridazinyl, preferably pyridyl, thiazoryl or 1,2,4-oxadiazolyl. Examples of bicyclic heteroaryl groups include indolyl, indazolyl, benzofuranyl, benzothienyl, benzothiazolyl, quinolyl, isoquinolyl, phthalazinyl, benzimidazolyl, benzoxazolyl and the like. The heterocycles include all position isomers such as 2-pyridyl, 3-pyridyl or 4-pyridyl.

The term "lower alkoxy-lower alkyl group" refers to a $C_{1-6}$ alkoxy-$C_{1-6}$ alkyl group such as a methoxymethyl, 2-methoxyethyl, ethoxymethyl, 2-ethoxyethyl group and the like, preferably a methoxylmethyl or 2-ethoxyethyl group.

The term "aryloxy-lower alkyl group" refers to an aryloxy-$C_{1-6}$ alkyl group such as a phenoxymethyl, 1-phenoxyethyl, 2-phenoxyethyl, 1-methyl-1-phenoxyethyl, 3-phenoxypropyl, naphthyloxymethyl group and the like.

The term "lower acyl group" refers to a $(C_{1-6}$ alkyl)-CO— group such as an acetyl, propionyl, butyryl, isobutyryl, pivaloyl, valeryl, isovaleryl group and the like.

The term "halo-lower alkylcarbonyl group" refers to a (halo-$C_{1-6}$ alkyl)-C(O)— group such as trifluoroacetyl, trichloroacetyl group and the like.

The term "cycloalkylcarbonyl group" refers to a (cycloalkyl)-C(O)— group such as a cyclopropylcarbonyl, cyclobutylcarbonyl, cyclopentylcarbonyl, cyclohexylcarbonyl group and the like.

The term "arylcarbonyl group" refers to a (aryl)-C(O)— group such as a benzoyl group and the like.

Examples of "arylcarbonyl group, wherein the ring of the arylcarbonyl group is unsubstituted or substituted with 1 to 5 substituents selected from the group consisting of a halogen atom, a lower alkyl group, a halo-lower alkyl group, a lower alkoxy group, a cycloalkyl-lower alkoxy group, a hydroxy group, a lower alkoxycarbonyl group, —C(O)NR$^{11}$R$^{12}$ and a cyano group" for R$^3$ include a benzoyl, 2-fluorobenzoyl, 3-fluorobenzoyl, 4-fluorobenzoyl, 2,4-difluorobenzoyl, 4-chlorobenzoyl, 2-methylbenzoyl, 3-methylbenzoyl, 4-methylbenzoyl, 2-methoxybenzoyl, 3-methoxybenzoyl, 4-methoxybenzoyl, 4-hydroxybenzoyl, 4-cyanobenzoyl, 4-methoxycarbonylbenzoyl, 4-ethoxycarbonylbenzoyl, 4-cyclopropylmethylbenzoyl group and the like, preferably a benzoyl, 2-fluorobenzoyl or 4-hydroxybenzoyl group, and more preferably a benzoyl group.

The term "heteroarylcarbonyl group" refers to a (heteroaryl)-C(O)— group such as a 2-furylcarbonyl, 2-thienylcarbonyl, 2-oxazolylcarbonyl, 2-thiazolylcarbonyl, 5-isoxazolylcarbonyl, 2-pyridylcarbonyl, 3-pyridylcarbonyl, 4-pyridylcarbonyl group and the like.

The term "aralkylcarbonyl group" refers to an (aralkyl)-C(O)— group such as a benzylcarbonyl, 2-phenylethylcarbonyl group and the like.

The term "aryloxy-lower alkylcarbonyl group" refers to a (aryloxy-$C_{1-6}$ alkyl)-C(O)— group such as a phenoxymethylcarbonyl group and the like.

The term "lower alkoxycarbonyl group" refers to a $(C_{1-6}$ alkoxy)-C(O)— group such as a methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl group and the like.

The term "cycloalkyloxycarbonyl group" refers to a (cycloalkyl)-O—C(O)— group such as a cyclopentyloxycarbonyl, cyclohexyloxycarbonyl group and the like.

The term "lower alkoxy-lower alkoxycarbonyl group" refers to a $(C_{1-6}$ alkoxy-$C_{1-6}$ alkoxy)-C(O)— group such as 2-methoxyethoxycarbonyl, 2-ethoxyethoxycarbonyl, 3-methoxy-propoxycarbonyl group and the like.

The term "lower alkoxycarbonyl-lower alkyl group" refers to a $(C_{1-6}$ alkoxy)-C(O)—$C_{1-6}$ alkyl group such as a methoxycarbonylmethyl, ethoxycarbonylmethyl, 2-(ethoxy-carbonyl)ethyl group and the like.

The term "lower alkylsulfonyl group" refers to a $(C_{1-6}$ alkyl)-SO$_2$— group such as a methanesulfonyl, ethanesulfonyl, propanesulfonyl, butane sulfonyl, pentanesulfonyl, hexanesulfonyl group and the like, preferable a methanesulfonyl group.

The term "cyclic amino group" refers to a 5- to 7-membered saturated cyclic amine which may contain —NH—, —O— or —S— as a member of the ring. Examples of cyclic amino groups include a 1-pyrrolidyl, piperidino, piperazino, morpholino, thiomorpholino group. The cyclic amino group may be optionally substituted with one or two alkyl group.

The term "lower alkylene group" refers to a bivalent saturated $C_{1-6}$ hydrocarbon chain, which may be straight chained or branched. Examples of lower alkylene groups include —CH$_2$—, —CH$_2$CH$_2$—, —CH(CH$_3$)—, —CH(CH$_3$)CH$_2$—, —CH$_2$CH(CH$_3$)—, —C(CH$_3$)$_2$— and the like, preferably —CH(CH$_3$)— or —C(CH$_3$)$_2$—.

In the case where a compound represented by general formula (I) contains one or more asymmetric carbons, then all stereoisomers in the R- or S-configuration at each of asymmetric carbons and their mixture are contemplated within the scope of the present invention. In such cases, racemic compounds, racemic mixtures, individual enantiomers and mixtures of diastereomers are also contemplated within the scope of the present invention.

In the case where a compound represented by general formula (I) exists in one or more geometrical isomers, then all geometrical isomers are also contemplated within the scope of the present invention.

In the case where a compound represented by general formula (I) exists in one or more atrop-isomers, then all atrop-isomers are also contemplated within the scope of the present invention.

A compound represented by general formula (I) may form a solvate with a pharmaceutically acceptable solvent such as water, ethanol and the like.

Compounds represented by general formula (I) may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; basic salts formed with inorganic bases such as lithium, sodium, potassium, calcium, magnesium and the like; basic salts formed with organic bases such as triethylamine, piperidine, morpholine, lysine and the like.

In an embodiment of a compound represented by general formula (I) of the present invention, preferably R$^1$ and R$^2$ are each independently a hydrogen atom, a lower acyl group, a lower alkoxycarbonyl group or —C(O)NR$^{11}$R$^{12}$, or R$^1$ and R$^2$ are joined together to form —C(O)—, and more preferably R$^1$ and R$^2$ are a hydrogen atom;

R$^3$ is preferably:
a) a halo-lower alkyl group,
b) a lower acyl group, c) a halo-lower alkylcarbonyl group,
d) a cycloalkylcarbonyl group,
e) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
f) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
g) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
h) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
i) a lower alkoxycarbonyl group,
j) a cycloalkyloxycarbonyl group,
k) a lower alkoxy-lower alkoxycarbonyl group,
l) a carboxy group,
m) a cyano group,
n) —C(O)NR$^{11}$R$^{12}$,
o) —C(O)C(O)NR$^{11}$R$^{12}$,
p) a lower alkylsulfonyl group,
q) —SO$_2$NR$^{11}$R$^{12}$ or
r) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group,
more preferably R$^3$ is:
a) a lower acyl group,
b) a halo-lower alkylcarbonyl group,
c) a cycloalkylcarbonyl group,
d) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
e) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
f) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
g) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
h) a lower alkoxycarbonyl group,
i) a cycloalkyloxycarbonyl group,
j) a lower alkoxy-lower alkoxycarbonyl group,
k) —C(O)C(O)NR$^{11}$R$^{12}$ or
l) a lower alkylsulfonyl group, even more preferably R$^3$ is:
a) a lower acyl group,
b) a cycloalkylcarbonyl group,
c) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
d) a lower alkoxycarbonyl group,
e) a cycloalkyloxycarbonyl group,
f) a lower alkoxy-lower alkoxycarbonyl group or
g) —C(O)C(O)NR$^{11}$R$^{12}$, and
especially preferably R$^3$ is:
a) a lower acyl group,
b) a cycloalkylcarbonyl group,
c) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
d) a lower alkoxycarbonyl group or
e) —C(O)C(O)NR$^{11}$R$^{12}$;
R$^4$ is preferably:
a) a lower alkyl group,
b) a halo-lower alkyl group,
c) a cycloalkyl group,
d) a heterocycloalkyl group,
e) a lower alkoxy-lower alkyl group,
f) an aryloxy-lower alkyl group or
g) a lower alkoxycarbonyl-lower alkyl group, and
more preferably R$^4$ is:
a) a lower alkyl group,
b) a cycloalkyl group,
c) a lower alkoxy-lower alkyl group or
d) a lower alkoxycarbonyl-lower alkyl group; or
preferably R$^{11}$ and R$^{12}$ are each independently a hydrogen atom, a lower alkyl group, a cycloalkyl group, a bridged cyclic hydrocarbon group or a phenyl group.
In a preferable embodiment of the present invention,
R$^1$ and R$^2$ are each independently a hydrogen atom, a lower acyl group, a lower alkoxycarbonyl group or —C(O)NR$^{11}$R$^{12}$, or R$^1$ and R$^2$ are joined together to form —C(O)—;
R$^3$ is:
a) a halo-lower alkyl group,
b) a lower acyl group,
c) a halo-lower alkylcarbonyl group,
d) a cycloalkylcarbonyl group,
e) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
f) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
g) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
h) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
i) a lower alkoxycarbonyl group,
j) a cycloalkyloxycarbonyl group, k) a lower alkoxy-lower alkoxycarbonyl group,
l) a carboxy group,
m) a cyano group,
n) —C(O)NR$^{11}$R$^{12}$,
o) —C(O)C(O)NR$^{11}$R$^{12}$,
p) a lower alkylsulfonyl group,
q) —SO$_2$NR$^{11}$R$^{12}$ or
r) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group;

R$^4$ is:
a) a lower alkyl group,
b) a halo-lower alkyl group,
c) a cycloalkyl group,
d) a heterocycloalkyl group,
e) a lower alkoxy-lower alkyl group,
f) an aryloxy-lower alkyl group or
g) a lower alkoxycarbonyl-lower alkyl group; and R$^{11}$ and R$^{12}$ are each independently a hydrogen atom, a lower alkyl group, a cycloalkyl group, a bridged cyclic hydrocarbon group, a phenyl group or an aralkyl group, or R$^{11}$ and R$^{12}$, together with the nitrogen atom to which they are bonded, form a cyclic amino group.

In a more preferable embodiment of the present invention,
R$^1$ and R$^2$ are a hydrogen atom,
R$^3$ is:
a) a halo-lower alkyl group,
b) a lower acyl group,
c) a halo-lower alkylcarbonyl group,
d) a cycloalkylcarbonyl group,
e) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
f) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
g) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
h) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
i) a lower alkoxycarbonyl group,
j) a cycloalkyloxycarbonyl group,
k) a lower alkoxy-lower alkoxycarbonyl group,
l) a carboxy group,
m) a cyano group,
n) —C(O)NR$^{11}$R$^{12}$,
o) —C(O)C(O)NR$^{11}$R$^{12}$,
p) a lower alkylsulfonyl group,
q) —SO$_2$NR$^{11}$R$^{12}$ or
r) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group;

R$^4$ is:
a) a lower alkyl group,
b) a halo-lower alkyl group,
c) a cycloalkyl group,
d) a heterocycloalkyl group,
e) a lower alkoxy-lower alkyl group,
f) an aryloxy-lower alkyl group or
g) a lower alkoxycarbonyl-lower alkyl group; and R$^{11}$ and R$^{12}$ are each independently a hydrogen atom, a lower alkyl group, a cycloalkyl group, a bridged cyclic hydrocarbon group, a phenyl group or an aralkyl group, or R$^{11}$ and R$^{12}$, together with the nitrogen atom to which they are bonded, form a cyclic amino group.

In an even more preferable embodiment of the present invention,
R$^1$ and R$^2$ are a hydrogen atom,
R$^3$ is:
a) a lower acyl group,
b) a halo-lower alkylcarbonyl group,
c) a cycloalkylcarbonyl group,
d) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
e) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
f) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
g) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
h) a lower alkoxycarbonyl group,
i) a cycloalkyloxycarbonyl group,
j) a lower alkoxy-lower alkoxycarbonyl group,
k) —C(O)C(O)NR$^{11}$R$^{12}$ or
l) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group;

R$^4$ is:
a) a lower alkyl group,
b) a halo-lower alkyl group,
c) a cycloalkyl group,
d) a heterocycloalkyl group,
e) a lower alkoxy-lower alkyl group,
f) an aryloxy-lower alkyl group or
g) a lower alkoxycarbonyl-lower alkyl group; and R$^{11}$ and R$^{12}$ are each independently a hydrogen atom, a lower alkyl group, a cycloalkyl group, a bridged cyclic hydrocarbon group, a phenyl group or an aralkyl group, or R$^{11}$ and R$^{12}$, together with the nitrogen atom to which they are bonded, form a cyclic amino group.

In another even more preferable embodiment of the present invention,
R$^1$ and R$^2$ are a hydrogen atom,
R$^3$ is:
a) a lower acyl group,
b) a halo-lower alkylcarbonyl group, c) a cycloalkylcarbonyl group, d) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group, e) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group, f) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group, g) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group, h) a lower alkoxycarbonyl group, i) a cycloalkyloxycarbonyl group, j) a lower alkoxy-lower alkoxycarbonyl group, k) —C(O)C(O)NR$^{11}$R$^{12}$ or l) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group; and R$^4$ is:

a) a lower alkyl group, b) a cycloalkyl group, c) a lower alkoxy-lower alkyl group, or d) a lower alkoxycarbonyl-lower alkyl group.

In another even more preferable embodiment of the present invention,

R$^1$ and R$^2$ are a hydrogen atom,

R$^3$ is:

a) a lower acyl group, b) a cycloalkylcarbonyl group, c) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group, d) a lower alkoxycarbonyl group, e) a cycloalkyloxycarbonyl group, f) a lower alkoxy-lower alkoxycarbonyl group, or g) —C(O)C(O)NR$^{11}$R$^{12}$; and R$^4$ is:

a) a lower alkyl group, b) a cycloalkyl group, c) a lower alkoxy-lower alkyl group, or d) a lower alkoxycarbonyl-lower alkyl group.

In an especially preferable embodiment of the present invention,

R$^1$ and R$^2$ are a hydrogen atom,

R$^3$ is:

a) a lower acyl group, b) a cycloalkylcarbonyl group, c) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group, d) a lower alkoxycarbonyl group, or e) —C(O)C(O)NR$^{11}$R$^{12}$; and R$^4$ is:

a) a lower alkyl group, b) a cycloalkyl group, c) a lower alkoxy-lower alkyl group, or d) a lower alkoxycarbonyl-lower alkyl group.

Specific examples of preferred embodiments of the present invention are compounds selected form the group consisting of:

[3,4-dihydroxy-6-(5-methyl-[1,2,4]oxadiazol-3-yl)-2-nitrophenyl]phenylmethanone;

1-[3,4-dihydroxy-6-(5-methyl-[1,2,4]oxadiazol-3-yl)-2-nitrophenyl]ethanone;

methyl 3,4-dihydroxy-6-(5-methyl-[1,2,4]oxadiazol-3-yl)-2-nitrobenzoate;

N-cyclohexyl-2-[3,4-dihydroxy-6-(5-methyl-[1,2,4]oxadiazol-3-yl)-2-nitrophenyl]-2-oxoacetamide;

N-cyclohexyl-2-[3,4-dihydroxy-6-(5-methyl-[1,2,4]oxadiazol-3-yl)-2-nitrophenyl]-N-methyl-2-oxoacetamide;

1-{6-[5-(2-ethoxyethyl)-[1,2,4]oxadiazol-3-yl]-3,4-dihydroxy-2-nitrophenyl}ethanone; and cyclohexyl-[3,4-dihydroxy-6-(5-methyl-[1,2,4]oxa-diazol-3-yl)-2-nitrophenyl]methanone.

Compound represented by general formula (I) can be prepared by the methods as illustrated in schemes 1 to 5.

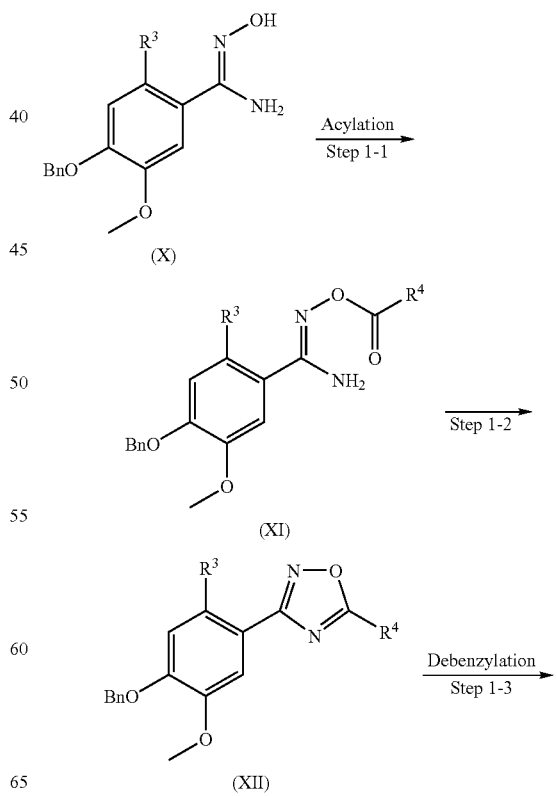

Scheme 1

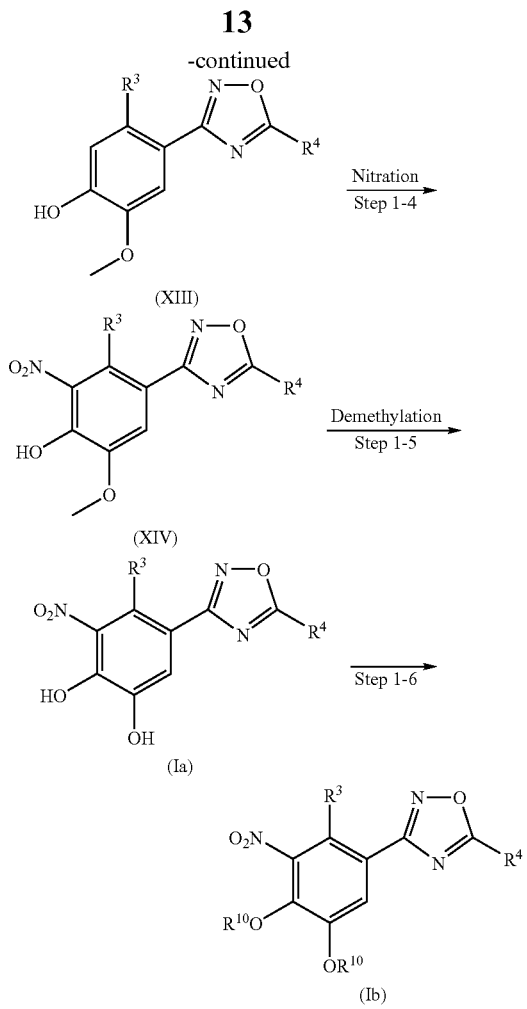

wherein $R^3$ and $R^4$ are as defined above, $R^{10}$ is a lower acyl or lower alkoxycarbonyl group or —CONR$^{11}$R$^{12}$, and Bn is a benzyl group.

Step 1-1

Acylation of amidoxime (X) with an acylating reagent in the presence of a base in an inert solvent or in a base-solvent provides acylamidoxime derivative (XI). The acylating reagents employed in the acylation reaction include acid halide, acid anhydride, mixed acid anhydride, benzotriazol-1-yl ester, 4-nitrophenyl ester, 2,5-dioxapyrrolidine ester or the like. The bases include triethylamine, pyridine, N,N-di-isopropyl-ethylamine or the like. The inert solvents include tetrahydro-furan, methylene chloride or the like. The acylation reaction is carried out ordinarily at −20° C. to reflux temperature. The reaction time varies depending on the starting materials employed, the solvent, the reaction temperature or the like, but is usually 15 minutes to 24 hours.

Alternatively, the acylamidoxime derivative (XI) can be prepared by condensing amidoxime (X) with carboxylic acid in the presence of a condensing reagent such as dicyclohexylcarbodiimide, 1-(3-dimethylaminopropyl)-3-ethylcarbodiimide hydrochloride, ethyl cyanophosphate, diphenylphosphoryl azide or the like. The condensing reaction is carried out ordinarily at −20° C. to reflux temperature. The reaction time varies depending on the starting materials employed, the solvent, the reaction temperature or the like, but is usually 15 minutes to 24 hours.

Step 1-2

Cyclization of acylamidoxime derivative (XI) in the presence of a base such as pyridine, tetrabutylammonium fluoride or the like in an inert solvent such as tetrahydrofuran or the like provides oxadiazole derivative (XII). The reaction is carried out ordinarily at 0° C. to 120° C. The reaction time varies depending on the starting materials employed, the solvent, the reaction temperature or the like, but is usually 15 minutes to 12 hours.

Alternatively, the oxadiazole derivative (XII) can be prepared by cyclizing acylamidoxime derivative (XI) in a base such as pyridine or the like. The cyclization is carried out ordinarily at 20° C. to reflux temperature. The reaction time varies depending on the starting materials employed, the solvent, the reaction temperature or the like, but is usually 15 minutes to 24 hours.

Step 1-3

The benzyl group of oxadiazole derivative (XII) is removed in the presence of a metal catalyst such as palladium carbon, platinum oxide or the like under an atmosphere of hydrogen in an inert solvent such as ethanol, N,N-dimethylformamide, tetrahydrofuran or the like to afford phenol derivative (XIII). The reaction is carried out ordinarily at room temperature to 80° C. The reaction time varies depending on the starting materials employed, the solvent, the reaction temperature or the like, but is usually 30 minutes to 12 hours.

Alternatively, the debenzylation reaction can be carried out by treating oxadiazole derivative (XII) with an acid or Lewis acid such hydrogen bromide, aluminum chloride, titanium tetrachloride or the like in an inert solvent such as methylene chloride, toluene or the like. The reaction is carried out ordinarily at 0° C. to 80° C. The reaction time varies depending on the starting materials employed, the solvent, the reaction temperature or the like, but is usually 15 minutes to 24 hours.

Step 1-4

Nitration of phenol derivative (XIII) with a nitrating reagent in an inert solvent provides nitrophenol derivative (XIV). The inert solvents employed in the reaction include methylene chloride, 1,2-dichloroethane, ethyl acetate, acetic acid, tetrahydrofuran, acetic anhydride or the like. The nitrating reagents include nitric acid, fuming nitric acid, nitronium tetrafluoroborate or the like. The reaction is carried out ordinarily at −40° C. to 80° C. The reaction time varies depending on the starting materials employed, the solvent, the reaction temperature or the like, but is usually 5 minutes to 12 hours. The nitration reaction can also be carried out, if desired, by adding an additive such as sulfuric acid or the like.

Step 1-5

Demethylation of nitrophenol derivative (XIV) with a demethylation reagent in an inert solvent provides compound (Ia). The inert solvents employed in the reaction include ethyl acetate, pyridine, 1,4-dioxane or the like. The demethylation reagents include aluminum chloride-pyridine, boron tribromide or the like. The reaction is carried out ordinarily at −20° C. to 120° C. The reaction time varies depending on the starting materials employed, the solvent, the reaction temperature or the like, but is usually 1 hour to 24 hours.

Alternatively, the demethylation can be carried out by treating nitrophenol derivative (XIV) with hydrobromic acid or hydroiodic acid in a solvent of acetic acid. The reaction is carried out ordinarily at 20° C. to reflux temperature. The reaction time varies depending on the starting materials employed, the reaction temperature or the like, but is usually 1 hour to 24 hours.

Step 1-6

Acylation of compound (Ia) with an acylating reagent provides compound (Ib). Such acylation reactions are well known to those ordinarily skilled in the art, and can be carried out according to procedures as described in T. W. Green and P. G. H. Wuts, "Protective Groups in Organic Synthesis" the fourth edition.
Scheme 2
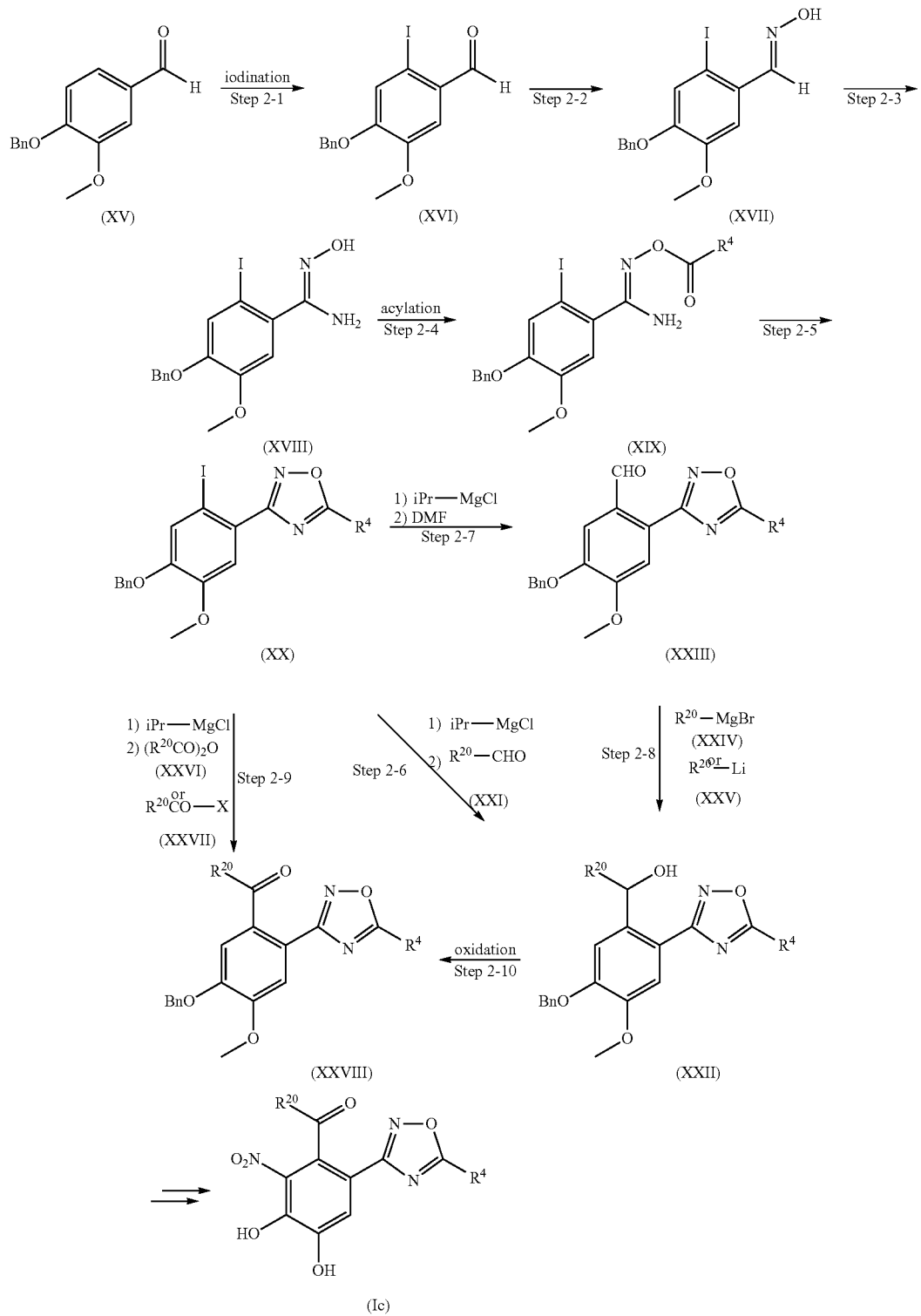
wherein $R^4$ and Bn are as defined above, $R^{20}$ represnts aryl, lower alkyl, halo-lower alkyl, cycloalkyl, heteroaryl or aralkyl, and X represents chloro, bromo or —N($CH_3$)$OCH_3$.

Step 2-1

Iodination of aldehyde derivative (XV) with an iodinating reagent such as iodine, N-iodosuccinimide or iodine monochloride in an inert solvent such as methylene chloride, methanol, acetic acid or the like provides iodobenzaldehyde (XVI). The reaction is carried out ordinarily at 20° C. to reflux temperature. The reaction time varies depending on the starting materials employed, the reaction temperature or the like, but is usually 15 minutes to 24 hours.

The iodination can be also carried out, if desired, by adding an additive such as trifluoroacetic acid, silver trifluoroacetate or the like.

Step 2-2

Oximation of iodobenzaldehyde (XVI) with hydroxylamine in an inert solvent such as ethanol, N,N-dimethylformamide, tetrahydrofuran or the like provides oxime derivative (XVII). The reaction is carried out ordinarily at 20° C. to reflux temperature. The reaction time varies depending on the starting materials employed, the reaction temperature or the like, but is usually 15 minutes to 24 hours. The reaction can also be carried out, if desired, by adding an additive such as sodium acetate, sodium hydroxide or the like.

Step 2-3

Chlorination of oxime derivative (XVII) with a chlorinating reagent such as N-chlorosuccinimide in an inert solvent such as N,N-dimethylformamide, tetrahydrofuran or the like provides a N-hydroxybenzimidoyl chloride derivative. The reaction is carried out at 0° C. to 80° C. The reaction time varies depending on the starting materials employed, the reaction temperature or the like, but is usually 5 minutes to 24 hours.

The N-hydroxybenzimidoyl chloride derivative is treated with an aminating reagent such as aqueous ammonia or the like in an inert solvent such as N,N-dimethylformamide, tetrahydrofuran or the like to afford amidoxime derivative (XVIII). The reaction is carried out at 0° C. to 30° C. The reaction time varies depending on the starting materials employed, the reaction temperature or the like, but is usually 15 minutes to 24 hours.

Step 2-4

Acylation of amidoxime derivative (XVIII) according to the procedures as described in Step 1-1 provides acylamidoxime derivative (XIX).

Step 2-5

Cyclization of acylamidoxime derivative (XIX) according to the procedures as described in Step 1-2 provides oxadiazole derivative (XX).

Step 2-6

Oxadiazole derivative (XX) is treated with an organic magnesium reagent in an inert solvent, followed by reaction with aldehyde (XXI) to afford benzylalcohol derivative (XXII). The inert solvents employed in the reaction include tetrahydrofuran or the like. The organic magnesium reagents include isopropyl magnesium chloride or the like. The reaction is carried out ordinarily at −78° C. to 10° C. The reaction time varies depending on the starting materials employed, the solvent, the reaction temperature or the like, but is usually 15 minutes to 2 hours.

Step 2-7

Oxadiazole derivative (XX) is treated with an organic magnesium reagent in an inert solvent, followed by reaction with N,N-dimethylformamide (DMF) to afford aldehyde derivative (XXIII). The inert solvents employed in the reaction include tetrahydrofuran or the like. The organic magnesium reagents include isopropyl magnesium chloride or the like. The reaction is carried out ordinarily at −78° C. to 10° C. The reaction time varies depending on the starting materials employed, the solvent, the reaction temperature or the like, but is usually 15 minutes to 2 hours.

Step 2-8

Aldehyde derivative (XXIII) is treated with an organic magnesium reagent (XXIV) or an organic lithium reagent (XXV) in an inert solvent such as tetrahydrofuran or the like to afford benzylalcohol derivative (XXII). The reaction is carried out ordinarily at −78° C. to 10° C. The reaction time varies depending on the starting materials employed, the solvent, the reaction temperature or the like, but is usually 15 minutes to 2 hours.

Step 2-9

Oxadiazole derivative (XX) is treated with an organic magnesium reagent in an inert solvent, followed by reaction with acid anhydride (XXVI), acid halide or N-methoxy-N-methylamide (XXVII) to afford ketone derivative (XXVIII). The inert solvents employed in the reaction include tetrahydrofuran or the like. The organic magnesium reagents include isopropyl magnesium chloride or the like. The reaction is carried out ordinarily at −78° C. to 50° C. The reaction time varies depending on the starting materials employed, the solvent, the reaction temperature or the like, but is usually 15 minutes to 2 hours.

Step 2-10

Oxidation of benzylalcohol derivative (XXII) with an oxidizing agent in a suitable solvent provides ketone derivative (XXVIII). The solvents employed in the reaction include methylene chloride, acetonitrile or the like. The oxidizing agents include manganese dioxide, sulfur trioxide-pyridine complex-dimethylsulfoxide, 4-methylmorpholine-N-oxide or the like. The reaction is carried out ordinarily at 0° C. to 30° C. The reaction time varies depending on the starting materials employed, the solvent, the oxidizing agent, the reaction temperature or the like, but is usually 15 minutes to 3 days.

Thereafter, compound (Ic) can be prepared from ketone derivative (XXVIII) according to the procedures as described in Step 1-3 to Step 1-5.

Scheme 3

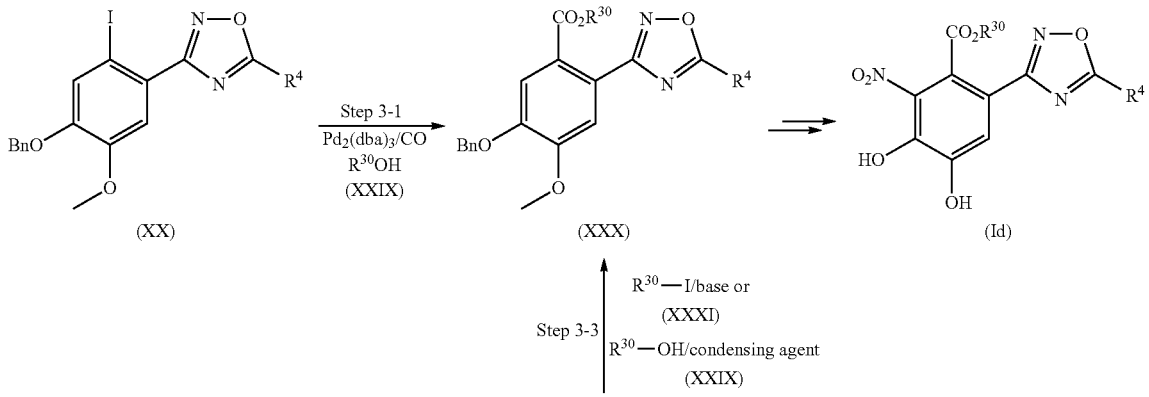

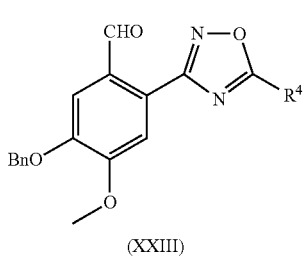 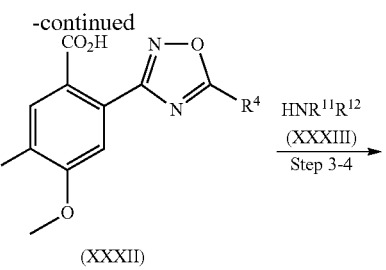

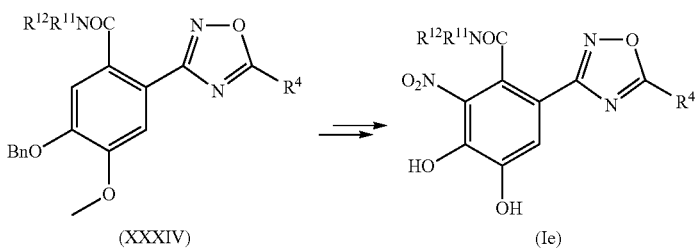

wherein $R^4$, $R^{11}$, $R^{12}$ and Bn are as defined above, $R^{30}$ represents lower alkyl, cycloalkyl or lower alkoxy-lower alkyl.

Step 3-1

Condensation of compound (XX) with alcohol (XXIX) under an atmosphere of carbon monoxide in the presence of a base, a palladium catalyst and a phosphine ligand in an inert solvent provides ester derivative (XXX). The inert solvents employed in the reaction include N,N-dimethylformamide, 1,4-dioxane, 1,2-dimethoxyethane, tetrahydrofuran, toluene or the like. The bases include triethylamine, N,N-diisopropylethylamine or the like. The palladium catalysts include tris(dibenzylidene-acetone)dipalladium(0), palladium acetate or the like. The phosphine ligands include 1,1'-bis(diphenylphosphino) ferrocene, triphenylphosphine or the like. The reaction is carried out ordinarily at 80° C. to 110° C. The reaction time varies depending on the starting materials employed, the solvent, the reaction temperature or the like, but is usually 1 hour to 24 hours.

Step 3-2

Oxidation of aldehyde derivative (XXIII) with an oxidizing agent in an inert solvent provides carboxylic acid derivative (XXXII). The solvents employed in the reaction include methylene chloride, acetonitrile, water, methanol or the like. The oxidizing agents include potassium permanganate, manganese dioxide, sodium chlorite-hydrogen peroxide, sodium chlorite-dimethylsulfoxide or the like. The reaction is carried out ordinarily at 0° C. to 80° C. The reaction time varies depending on the starting materials employed, the solvent, the oxidizing agent, the reaction temperature or the like, but is usually 15 minutes to 3 days. The reaction can be carried out, if desired, by adding an additive such as sodium hydrogen phosphate, sulfuric acid or the like.

Step 3-3

Carboxylic acid derivative (XXXII) is treated with alkyl halide (XXXI) in the presence of a base in an inert solvent provides ester derivative (XXX). The inert solvents employed in the reaction include 1,4-dioxane, N,N-dimethylformamide, 1,2-dimethoxyethane, tetrahydrofuran or the like. The bases include sodium tert-butoxide, potassium tert-butoxide, potassium carbonate or the like. The reaction is carried out ordinarily at 0° C. to 100° C. The reaction time varies depending on the starting materials employed, the solvent, the reaction temperature or the like, but is usually 5 minutes to 24 hours.

The ester derivative (XXX) can be prepared by condensing carboxylic acid derivative (XXXII) with alcohol (XXIX) in the presence of a condensing agent such as dicyclohexylcarbodiimide, 1-(3-dimethylaminopropyl)-3-ethylcarbodiimide hydrochloride, diethyl cyanophosphate, diphenylphosphoryl-azide or the like in an inert solvent such as methylene chloride, N,N-dimethylformamide or the like. The reaction can be carried out, if desired, by adding a base such as triethylamine or the like.

Step 3-4

Carboxylic acid derivative (XXXII) is treated with amine (XXXIII) in the presence of a condensing agent such as dicyclohexylcarbodiimide, 1-(3-dimethylaminopropyl)-3-ethyl-carbodiimide hydrochloride, diethyl cyanophosphate, diphenylphosphorylazide or the like in an inert solvent such as methylene chloride, N,N-dimethylformamide, tetrahydrofuran or the like to afford amide derivative (XXXIV). The reaction is carried out ordinarily at −20° C. to reflux temperature. The reaction time varies depending on the starting materials employed, the solvent, the reaction temperature or the like, but is usually 15 minutes to 24 hours. The reaction can be carried out, if desired, by adding an additive such as triethylamine or the like.

Thereafter, compound (Id) can be prepared from compound (XXX) according to the procedures as described in Step 1-3 to Step 1-5. Compound (Ie) can be prepared from compound (XXXIV) according to the procedures as described in Step 1-3 to Step 1-5.

Scheme 4

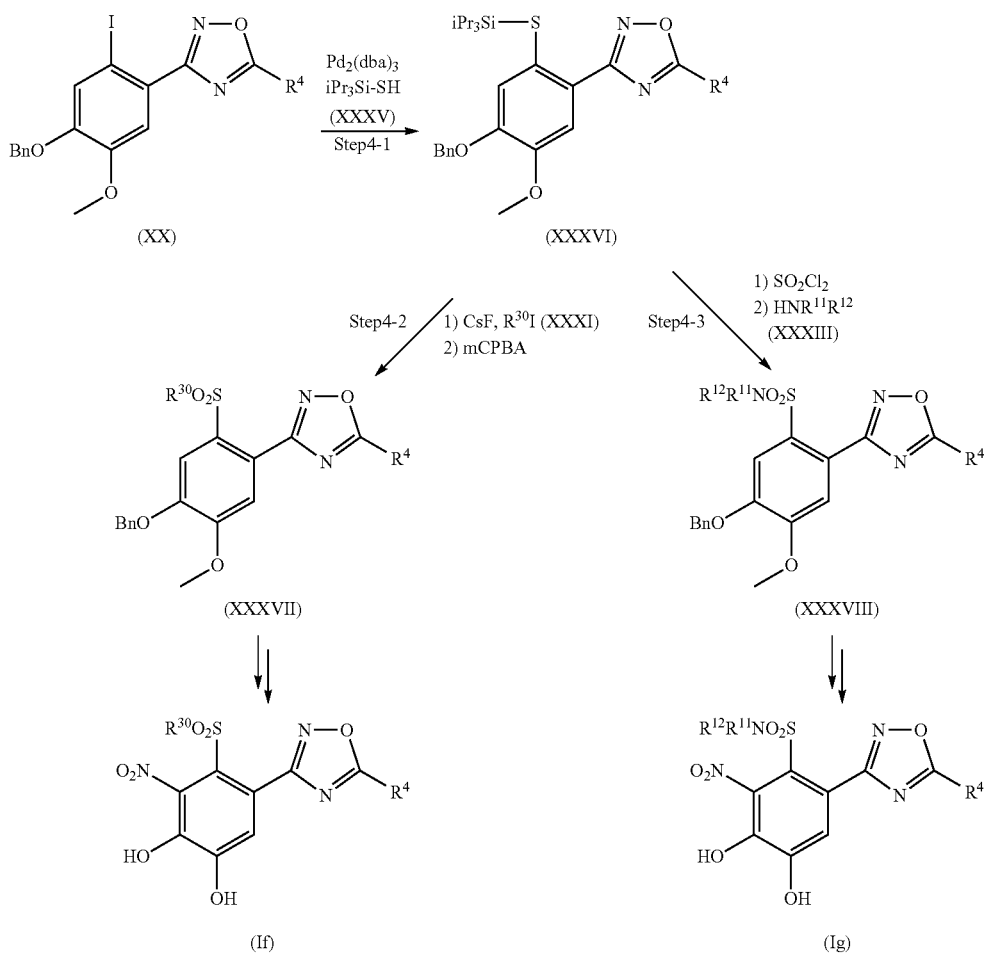

wherein $R^4$, $R^{11}$, $R^{12}$, $R^{30}$ and Bn are as defined above.

Step 4-1

Condensation of compound (XX) with triisopropylsilanethiol (XXXV) in the presence of a base, a palladium catalyst and a phosphine ligand in an inert solvent provides triisopropylsilyl phenyl thioether (XXXVI). The inert solvents employed in the reaction include toluene, N,N-dimethylformamide, 1,4-dioxane, 1,2-dimethoxymethane or the like. The bases include sodium hexamethyldisilazide, lithium hexamethyldisilazide, potassium tert-butoxide or the like. The paladium catalysts include tris(dibenzylidene-acetone)dipalladium(0), tetrakis(triphenylphosphine)palladium(0), palladium acetate or the like. The phosphine ligands include (oxydi-2,1-phenylene)bis(diphenylphosphine) or the like. The reaction is carried out ordinarily at 60° C. to 110° C. The reaction time varies depending on the starting materials employed, the solvent, the reaction temperature or the like, but is usually 1 hour to 24 hours.

Step 4-2

The triisopropylsilyl group of triisopropylsilyl phenyl thioether derivative (XXXVI) is converted to the corresponding alkyl group ($R^{30}$) by treatment of alkyl halide (XXXI) in the presence of a base such as cesium fluoride, tetrabutylammonium fluoride or the like in an inert solvent such as 1,4-dioxane, N,N-dimethylformamide, 1,2-dimethoxyethane, tetrahydrofuran or the like to afford an alkyl phenyl thioether derivative. The reaction is carried out ordinarily at 0° C. to 100° C. The reaction time varies depending on the starting materials employed, the solvent, the reaction temperature or the like, but is usually 5 minutes to 24 hours.

Oxidation of the alkyl phenyl thioether derivative with an oxidizing agent in a suitable solvent provides sulfone derivative (XXXVII). The solvents employed in the reaction include methylene chloride, acetone, acetic acid, water or the like. The oxidizing agents include m-chloroperbenzoic acid, oxone (registered mark), hydrogen peroxide solution, sodium perborate or the like. The reaction is carried out ordinarily at 0° C. to 80° C. The reaction time varies depending on the starting materials employed, the solvent, the reaction temperature or the like, but is usually 5 minutes to 24 hours.

Step 4-3

Triisopropylsilyl phenyl thioether derivative (XXXVI) is treated with sulfuryl chloride in the presence of a nitrate such as potassium nitrate, sodium nitrate, silver nitrate or the like in an inert solvent such as acetonitrile, N,N-dimethylformamide or the like to afford a sulfonyl chloride derivative. The reaction is carried out ordinarily at 0° C. to 40° C. The reaction time varies depending on the starting materials employed, the solvent, the reaction temperature or the like, but is usually 5 minutes to 5 hours.

Condensation of the sulfonyl chloride derivative with amine (XXXIII) in the presence of a base such as triethylamine, N,N-diisopropylethylamine or the like in an inert solvent such as tetrahydrofuran, N,N-dimethylformamide, ethyl acetate, methylene chloride or the like provides sulfonamide derivative (XXXVIII). The reaction is carried out ordinarily at 0° C. to 40° C. The reaction time varies depending on the starting materials employed, the solvent, the reaction temperature or the like, but is usually 5 minutes to 5 hours.

Thereafter, compound (If) can be prepared from compound (XXXVII) according to the procedures as described in Step 1-3 to Step 1-5. Compound (Ig) can be prepared from compound (XXXVIII) according to the procedures as described in Step 1-3 to Step 1-5.

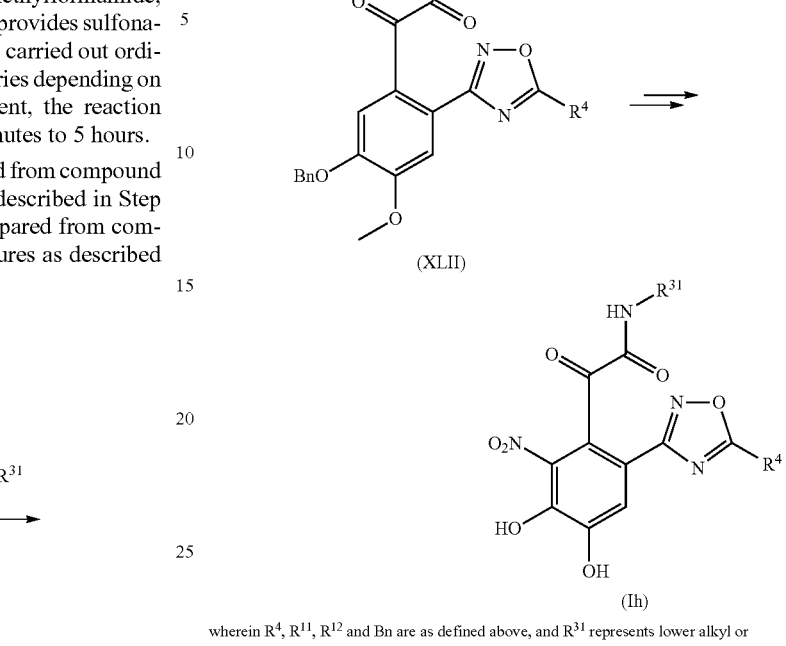

wherein $R^4$, $R^{11}$, $R^{12}$ and Bn are as defined above, and $R^{31}$ represents lower alkyl or cycloalkyl.

Step 5-1

Condensation of aldehyde derivative (XXIII) with isocyanide (XXXIX) in the presence of acetic acid in an inert solvent such as acetonitrile, methylene chloride, diethyl ether or the like provides ester derivative (XL). The reaction is carried out ordinarily at 20° C. to 100° C. The reaction time varies depending on the starting materials employed, the solvent, the reaction temperature or the like, but is usually 5 minutes to 24 hours. The reaction can also be carried out, if desired, by adding an additive such as titanium tetrachloride or the like.

Step 5-2

Hydrolysis of ester derivative (XL) in the presence of a base such as sodium hydroxide, potassium hydroxide, lithium hydroxide or the like in an inert solvent such as tetrahydrofuran, methanol, ethanol, water or the like provides alcohol derivative (XLI). The reaction is carried out ordinarily at 20° C. to 100° C. The reaction time varies depending on the starting materials employed, the solvent, the reaction temperature or the like, but is usually 5 minutes to 24 hours.

Step 5-3

Oxidation of alcohol derivative (XLI) according to the procedures as described in Step 2-10 provides ketone derivative (XLII).

Thereafter, compound (Ih) can be prepared from compound (XLII) according to the procedures as described in Step 1-3 to Step 1-5.

The forementioned schemes are exemplary for preparing compounds represented by general formula (I) of the present invention and synthetic intermediates thereof. Those ordinarily skilled in the art will appreciate that various changes or modifications of the forementioned schemes may be made without departing from the scope of the invention.

Compounds represented by general formula (I) of the present invention and intermediates for preparing the compounds of the present invention can be isolated or purified, if required, according to conventional isolation or purification techniques well known to those skilled in the art, such as solvent extraction, crystallization, recrystallization, chromatography, preparative high performance liquid chromatography or the like.

Compounds of general formula (I) exhibit excellent COMT inhibitory activities, and are useful as a therapeutic or prophylactic agent for Parkinson's disease. Compounds of general formula (I) are preferably used in combination with L-dopa. Compounds of general formula (I) may be used in combination with L-dopa and an aromatic L-amino acid decarboxylase inhibitor. Examples of aromatic L-amino acid decarboxylase inhibitors which may be used in combination with COMT inhibitors of the present invention, include carbidopa, benserazide or the like.

COMT inhibitors of the present invention can be used, if required, in combination with anti-Parkinson drugs other than L-dopa. Such anti-Parkinson drugs include droxidopa, melevodopa, threodops; dopamine $D_2$ receptor agonists such as cabergoline, bromocriptine mesylate, terguride, talipexole hydrochloride, ropinirole hydrochloride, pergolide mesylate, pramipexole hydrochloride, rotigotine and the like; anticholinergic agents such as profenamine, trihexyphenidyl hydrochloride, mazaticol hydrochloride, biperiden, piroheptinehydrochloride, methixene hydrochloride and the like; adenosine $A_{2A}$ receptor antagonists such as istradefylline and the like; NMDA antagonists such as budipine and the like; monoamine oxidase B inhibitors such as selegiline hydrochloride, rasagiline mesylate, safinamide mesylate and the like; zonisamide; amantadine hydrochloride and the like.

Compounds of the present invention are useful as a therapeutic or prophylactic agent for depression. Compounds of the present invention are useful as a therapeutic agent for hypertension since compounds of the present invention exhibit urinary sodium excretion promoting activities.

Pharmaceutical compositions comprising a compound of general formula (I) or a pharmaceutically acceptable salt thereof can be administered in various dosage forms depending on their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical carriers such as excipients, disintegrators, binders, lubricants, diluents, buffers, isotonic agents, preservatives, wetting agents, emulsifying agents, dispersing agents, stabilizing agents, solubilizing agents and the like, according to a conventional formulation procedure depending upon their dosage forms.

The dosage of a compound represented by general formula (I) or a pharmaceutically acceptable salt thereof is appropriately determined depending on the age, sex or body weight of the individual patient, the severity of the disease, the condition to be treated and the like. A typical dosage for oral administration is in the range of from about 10 mg to about 3000 mg per day per adult human. A typical dosage for parenteral administration is in the range of from about 5 mg to about 1000 mg per day per adult human. The dosages may be administered in single or divided doses, for example one to several times daily.

A pharmaceutical combination comprising a compound represented by general formula (I) or a pharmaceutically acceptable salt thereof, and at least one selected from L-dopa and an aromatic L-amino acid decarboxylase inhibitor, can be administered as a single pharmaceutical composition comprising all of active ingredients, or as separately formulated pharmaceutical compositions each of which comprises a single active ingredient. Where separately formulated pharmaceutical compositions are used, the compositions may be administered separately, concurrently or at different intervals. Alternatively, where separately formulated pharmaceutical compositions are used, the compositions may be mixed together with an appropriate diluent, and administered simultaneously.

In a pharmaceutical combination comprising a compound represented by general formula (I) or a pharmaceutically acceptable salt thereof, and at least one selected from L-dopa and an aromatic L-amino acid decarboxylase inhibitor, the dosage of each active ingredient may be appropriately determined depending on the age, sex or body weight of the individual patient, the severity of the disease, administration time, dosage form, administration method, combination of active ingredients and the like.

Advantageous Effects of Invention

Compounds of the present invention exhibit potent COMT inhibitory activities. Moreover, compounds of the present invention have a desirable safety profile since compounds of the present invention have extremely slight hepatotoxicity. Accordingly, compounds of the present invention are useful as a therapeutic or prophylactic agent for Parkinson's disease, depression or hypertension. Especially, compounds of the present invention are useful as a therapeutic or prophylactic agent for Parkinson's disease since use of compounds of the present invention in combination with L-dopa increases the bioavailability of L-dopa remarkably.

BEST MODE FOR CARRYING OUT THE INVENTION

The following reference examples, examples and test examples illustrate the invention in further detail. It is to be understood, however, that they are not to be construed as limiting the scope of the invention in any way.

Reference Example 1-1

4-Benzyloxy-2-iodo-5-methoxybenzaldehyde

To a mixture of 4-benzyloxy-3-methoxybenzaldehyde (10 g), silver trifluoroacetate (11.4 g) and methylene chloride (105 mL) was added iodine (13.1 g) at room temperature. After stirring for 2 hours, the mixture was passed through a layer of Celite (registered mark). The filtrate was washed with an aqueous solution of sodium hydrogen sulfite and brine successively, dried over anhydrous magnesium sulfate, and concentrated under reduced pressure. The residue was triturated with methanol:water=4:1 to give the title compound (13.2 g).

$^1$H-NMR (CDCl$_3$) δ ppm: 3.91 (3H, s), 5.19 (2H, s), 7.30-7.50 (7H, m), 9.86 (1H, s)

Reference Example 1-2

5-Benzyloxy-2-iodo-4-methoxybenzaldehyde

The title compound was prepared in a manner similar to those as described in Reference example 1-1 using 3-benzyloxy-4-methoxybenzaldehyde instead of 4-benzyloxy-3-methoxybenz-aldehyde.

$^1$H-NMR (CDCl$_3$) δ ppm: 3.95 (3H, s), 5.16 (2H, s), 7.29-7.47 (6H, m), 7.48 (1H, s), 9.84 (1H, s)

Reference Example 2-1

4-Benzyloxy-2-iodo-5-methoxybenzaldehyde oxime

A mixture of 4-benzyloxy-2-iodo-5-methoxybenzaldehyde (Reference example 1-1) (12.2 g), hydroxylamine hydrochloride (2.54 g), sodium acetate (6 g) and ethanol (170 mL) was stirred at 70° C. for 1.5 hours. The mixture was concentrated under reduced pressure. Water was added to the residue, and the mixture was stirred at room temperature for 30 minutes. The solid was collected by filtration to give the title compound (12.8 g).

$^1$H-NMR (CDCl$_3$) δ ppm: 3.88 (3H, s), 5.13 (2H, s), 7.19 (1H, s), 7.29 (1H, s), 7.30-7.50 (6H, m), 8.30 (1H, s)

Reference examples 2-2 to 2-3 were prepared in a manner similar to those as described in Reference example 2-1 using the corresponding aldehydes instead of 4-benzyloxy-2-iodo-5-methoxybenzaldehyde. These were illustrated in table 1.

TABLE 1

| Reference example | Structure |
| --- | --- |
| 2-1 | 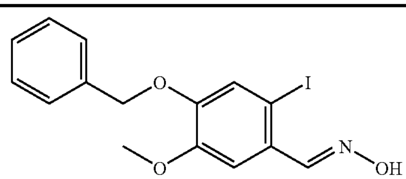 |
| 2-2 | 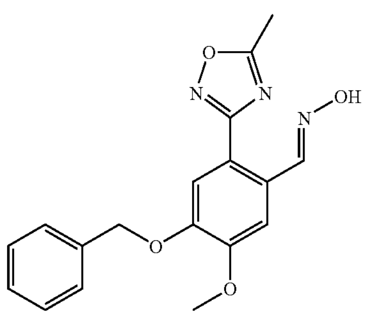 |
| 2-3 | 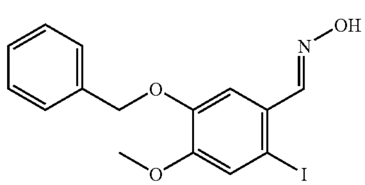 |

The physical data of reference example 2-3 was shown below.

Reference Example 2-3

$^1$H-NMR (CDCl$_3$) δ ppm: 3.88 (3H, s), 5.13 (2H, s), 7.25 (1H, s), 7.29-7.45 (6H, m), 8.28 (1H, s)

Reference Example 3-1

4-Benzyloxy-N-hydroxy-2-iodo-5-methoxybenzamidine

To a mixture of 4-benzyloxy-2-iodo-5-methoxy-benzaldehyde oxime (reference example 2-1) (12.8 g) and N,N-dimethylformamide (110 mL) was added N-chlorosuccinimide (4.9 g) at room temperature. After stirring at room temperature for 20 minutes, water and ethyl acetate were added to the mixture under ice-bath cooling. The separated organic layer was dried over anhydrous magnesium sulfate, and concentrated under reduced pressure to give 4-benzyloxy-N-hydroxy-2-iodo-5-methoxy-benzimidoylchloride.

To a mixture of 4-benzyloxy-N-hydroxy-2-iodo-5-methoxy-benzimidoylchloride and N,N-dimethylformamide (110 mL) was added a 28% ammonia in water (12 mL) under ice-bath cooling. After stirring for 3 hours under ice-bath cooling, water and ethyl acetate were added to the mixture. The separated organic layer was washed with water and brine successively, dried over anhydrous magnesium sulfate, and concentrated under reduced pressure. The residue was triturated with hexane:diethyl ether=1:4 to give the title compound (9.3 g).

$^1$H-NMR (DMSO-d$_6$) δ ppm: 3.77 (3H, s), 5.12 (2H, s), 5.65 (2H, br s), 6.91 (1H, s), 7.30-7.50 (6H, m), 9.35 (1H, s)

Reference examples 3-2 to 3-3 were prepared in a manner similar to those as described in Reference example 3-1 using the corresponding oximes instead of 4-benzyloxy-2-iodo-5-methoxybenzaldehyde oxime. These were illustrated in table 2.

TABLE 2

| Reference example | Structure |
| --- | --- |
| 3-1 | 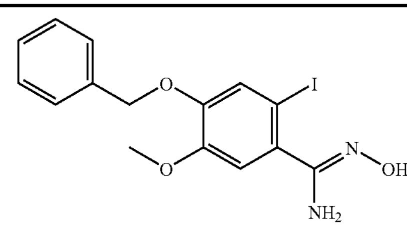 |
| 3-2 | 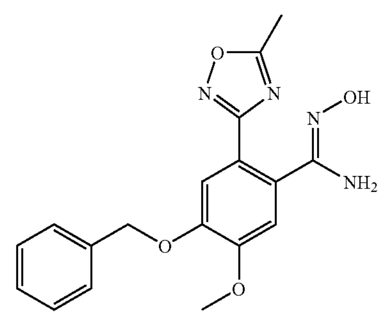 |
| 3-3 | 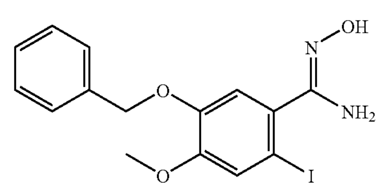 |

The physical data of reference example 3-3 was shown below.

Reference Example 3-3

$^1$H-NMR (CDCl$_3$) δ ppm: 3.87 (3H, s), 5.09 (2H, s), 7.00 (1H, s), 7.27-7.50 (5H, m)

Reference Example 4-1

3-(4-Benzyloxy-2-iodo-5-methoxyphenyl)-5-methyl-[1,2,4]oxa-diazole

To a mixture of 4-benzyloxy-N-hydroxy-2-iodo-5-methoxy-benzamidine (reference example 3-1) (35 g), triethylamine (31 mL) and tetrahydrofuran (31 mL) was added acetyl chloride (8.2 mL) under ice-bath cooling. The mixture was stirred at the same temperature for 1 hour. Insoluble materials were removed by filtration. To the filtrate was added tetrabutylammonium fluoride (1 mol/L tetrahydrofuran solution, 89 mL). After stirring at the same temperature for 2 hours, water and ethylacetate were added to the mixture. The separated organic layer was washed with 1 mol/L hydrochloric acid, a 1 mol/L aqueous solution of sodium hydroxide, an aqueous solution of sodium bicarbonate and brine successively, dried over anhydrous magnesium sulfate, and concentrated under reduced pressure. The residue was triturated with methanol to give the title compound (31.5 g).

$^1$H-NMR (CDCl$_3$) δ ppm: 2.67 (3H, s), 3.90 (3H, s), 5.16 (2H, s), 7.28 (1H, s), 7.30-7.50 (6H, m)

Reference Example 4-2

3-(5-Benzyloxy-2-iodo-4-methoxyphenyl)-5-methyl-[1,2,4]oxa-diazole

To a mixture of 5-benzyloxy-N-hydroxy-2-iodo-4-methoxy-benzamidine (reference example 3-3) (20 g) and pyridine (115 mL) was added acetyl chloride (3.8 mL) under ice-bath cooling. After stirring at the same temperature for 3 hours, the mixture was stirred and heated at 120° C. for 3 hours. After cooling to room temperature, the mixture was concentrated under reduced pressure. To the residue were added ethyl acetate and 2 mol/L hydrochloric acid. The separated organic layer was washed with 2 mol/L hydrochloric acid and brine successively, dried over anhydrous magnesium sulfate, and concentrated under reduced pressure. The residue was purified by silica gel column chromatography (eluent: 15%-50% ethyl acetate/hexane, gradient elution) to give the title compound (17.0 g).

$^1$H-NMR (CDCl$_3$) δ ppm: 2.66 (3H, s), 3.91 (3H, s), 5.14 (2H, s), 7.25-7.50 (7H, m)

Reference examples 4-3 to 4-13 were prepared in a manner similar to those as described in Reference example 4-1 using the corresponding amidines and acid chlorides or acid anhydrides instead of 4-benzyloxy-N-hydroxy-2-iodo-5-methoxybenzamidine and acetyl chloride. These were illustrated in table 3.

TABLE 3

| Reference example | Structure |
|---|---|
| 4-1 | 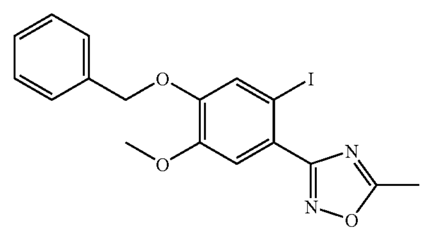 |
| 4-2 | 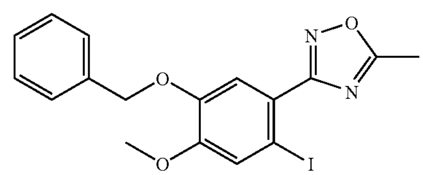 |
| 4-3 | 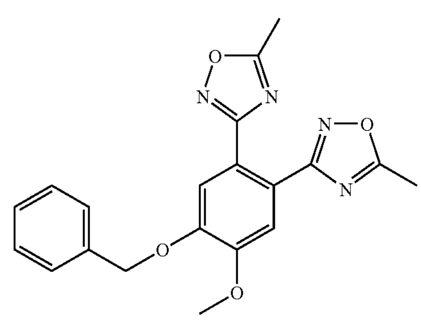 |

TABLE 3-continued

| Reference example | Structure |
|---|---|
| 4-4 | 3-(4-benzyloxy-2-iodo-5-methoxyphenyl)-5-cyclopropyl-1,2,4-oxadiazole |
| 4-5 | 3-(4-benzyloxy-2-iodo-5-methoxyphenyl)-5-(methoxymethyl)-1,2,4-oxadiazole |
| 4-6 | 3-(4-benzyloxy-2-iodo-5-methoxyphenyl)-5-tert-butyl-1,2,4-oxadiazole |
| 4-7 | 3-(4-benzyloxy-2-iodo-5-methoxyphenyl)-5-(phenoxymethyl)-1,2,4-oxadiazole |
| 4-8 | 3-(4-benzyloxy-2-iodo-5-methoxyphenyl)-5-isopropyl-1,2,4-oxadiazole |
| 4-9 | 3-(4-benzyloxy-2-iodo-5-methoxyphenyl)-5-propyl-1,2,4-oxadiazole |

TABLE 3-continued

| Reference example | Structure |
|---|---|
| 4-10 | (structure: 4-benzyloxy-2-iodo-5-methoxyphenyl-1,2,4-oxadiazole with ethyl propanoate substituent) |
| 4-11 | (structure: 4-benzyloxy-2-iodo-5-methoxyphenyl-1,2,4-oxadiazole with CF₃ substituent) |
| 4-12 | (structure: 4-benzyloxy-2-iodo-5-methoxyphenyl-1,2,4-oxadiazole with tetrahydropyran substituent) |
| 4-13 | (structure: 4-benzyloxy-2-iodo-5-methoxyphenyl-1,2,4-oxadiazole with 2-ethoxyethyl substituent) |

The physical data of reference examples 4-3 to 4-13 were shown below.

Reference Example 4-3

$^1$H-NMR (CDCl$_3$) δ ppm: 2.59 (3H, s), 2.60 (3H, s), 3.97 (3H, s), 5.22 (2H, s), 7.25-7.50 (7H, m)

Reference Example 4-4

$^1$H-NMR (CDCl$_3$) δ ppm: 1.23-1.28 (2H, m), 1.30-1.34 (2H, m), 2.24-2.30 (1H, m), 3.89 (3H, s), 5.15 (2H, s), 7.25 (1H, s), 7.31-7.45 (6H, m)

Reference Example 4-5

$^1$H-NMR (CDCl$_3$) δ ppm: 3.57 (3H, s), 3.90 (3H, s), 4.77 (2H, s), 5.17 (2H, s), 7.32 (1H, s), 7.33-7.46 (5H, m), 7.47 (1H, s)

Reference Example 4-6

$^1$H-NMR (CDCl$_3$) δ ppm: 1.51 (9H, s), 3.91 (3H, s), 5.16 (2H, s), 7.29 (1H, s), 7.31-7.45 (6H, m)

Reference Example 4-7

$^1$H-NMR (CDCl$_3$) δ ppm: 3.90 (3H, s), 5.17 (2H, s), 5.37 (2H, s), 7.00-7.10 (3H, m), 7.25-7.50 (9H, m)

Reference Example 4-8

$^1$H-NMR (CDCl$_3$) δ ppm: 1.40-1.50 (6H, m), 3.20-3.40 (1H, m), 3.90 (3H, s), 5.16 (2H, s), 7.29 (1H, s), 7.30-7.50 (6H, m)

Reference Example 4-9

$^1$H-NMR (CDCl$_3$) δ ppm: 1.00-1.10 (3H, m), 1.80-2.00 (2H, m), 2.90-3.00 (2H, m), 3.90 (3H, s), 5.16 (2H, s), 7.28 (1H, s), 7.30-7.50 (6H, m)

Reference Example 4-10

$^1$H-NMR (CDCl$_3$) δ ppm: 1.27 (3H, t, J=7.2 Hz), 2.94 (2H, t, J=7.4 Hz), 3.28 (2H, t, J=7.4 Hz), 3.90 (3H, s), 4.19 (2H, q, J=7.2 Hz), 5.16 (2H, s), 7.20-7.50 (7H, m)

Reference Example 4-11

¹H-NMR (CDCl₃) δ ppm: 3.92 (3H, s), 5.18 (2H, s), 7.33-7.46 (6H, m), 7.50 (1H, s)

Reference Example 4-12

¹H-NMR (CDCl₃) δ ppm: 2.05-2.15 (4H, m), 3.24-3.34 (1H, m), 3.54-3.64 (2H, m), 3.90 (3H, s), 4.03-4.10 (2H, m), 5.16 (2H, s), 7.30 (1H, s), 7.31-7.48 (6H, m)

Reference Example 4-13

¹H-NMR (CDCl₃) δ ppm: 1.20 (3H, t, J=6.8 Hz), 3.24 (2H, t, J=6.7 Hz), 3.56 (2H, q, J=6.8 Hz), 3.85-4.00 (5H, m), 5.16 (2H, s), 7.30 (1H, s), 7.30-7.50 (6H, m)

Reference Example 5-1

5-Benzyloxy-4-methoxy-2-(5-methyl-[1,2,4]oxadiazol-3-yl)benzoic acid

To a mixture of 5-benzyloxy-4-methoxy-2-(5-methyl-[1,2,4]oxadiazol-3-yl)benzaldehyde (reference example 15-1) (5.38 g), dimethyl sulfoxide (5.89 mL), concentrated sulfuric acid (0.506 mL), water (8 mL) and acetonitrile (41 mL) was added a mixture of sodium chlorite (2.25 g) and water (10 mL). After stirring at room temperature for 30 minutes, water was added to the mixture. The solid was collected by filtration to give the title compound (3.58 g).

¹H-NMR (CDCl₃) δ ppm: 2.67 (3H, s), 3.95 (3H, s), 5.23 (2H, s), 7.19 (1H, s), 7.30-7.50 (5H, m), 7.68 (1H, s)

Reference Example 6-1

[5-Benzyloxy-4-methoxy-2-(5-methyl-[1,2,4]oxadiazol-3-yl)phenyl]phenylmethanol

To a mixture of 5-benzyloxy-4-methoxy-2-(5-methyl-[1,2,4]oxadiazol-3-yl)benzaldehyde (reference example 15-1) (450 mg) and tetrahydrofuran (5.6 mL) was added dropwise phenylmagnesium bromide (1.08 mol/L tetrahydrofuran solution, 1.4 mL) in an ice salt bath. After stirring at the same temperature for 30 minutes, an aqueous solution of ammonium chloride, 2 mol/L hydrochloric acid and ethyl acetate were added to the mixture. The separated organic layer was dried over anhydrous magnesium sulfate, and concentrated under reduced pressure to give the title compound (564 mg).

¹H-NMR (CDCl₃) δ ppm: 2.64 (3H, s), 3.94 (3H, s), 4.60-4.70 (1H, m), 4.90-5.10 (2H, m), 6.10-6.20 (1H, m), 6.72 (1H, s), 7.20-7.40 (10H, m), 7.49 (1H, s)

Reference examples 6-2 to 6-7 were prepared in a manner similar to those as described in Reference example 6-1 using the corresponding aldehydes and organomagnesium instead of 5-benzyloxy-4-methoxy-2-(5-methyl-[1,2,4]oxadiazol-3-yl)benzaldehyde and phenylmagnesium bromide. These were illustrated in table 4.

TABLE 4

| Reference example | Structure |
|---|---|
| 6-1 | 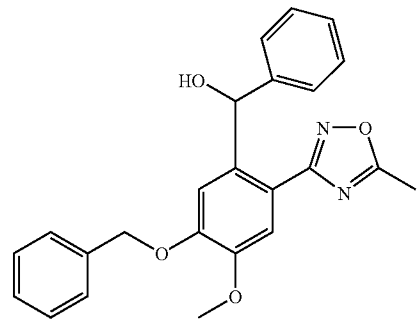 |
| 6-2 | 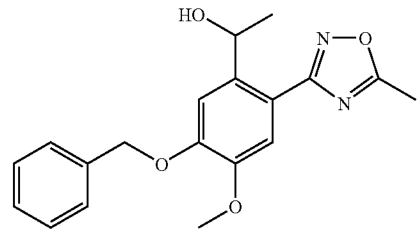 |
| 6-3 | 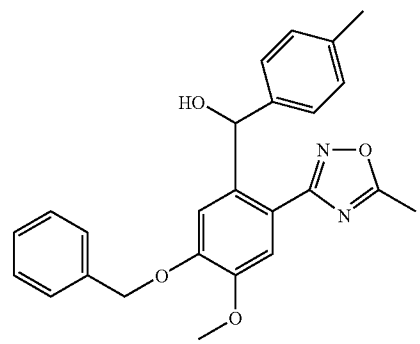 |
| 6-4 | 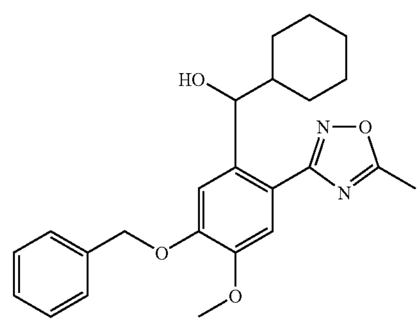 |
| 6-5 | 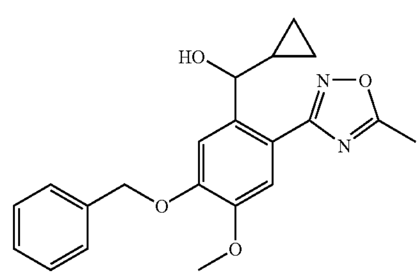 |

TABLE 4-continued

| Reference example | Structure |
|---|---|
| 6-6 | [Structure: 1-(4-benzyloxy-5-methoxy-2-(5-isopropyl-1,2,4-oxadiazol-3-yl)phenyl)ethan-1-ol] |
| 6-7 | [Structure: 1-(4-benzyloxy-5-methoxy-2-(5-propyl-1,2,4-oxadiazol-3-yl)phenyl)ethan-1-ol] |

The physical data of reference examples 6-2 to 6-4 and 6-6 to 6-7 were shown below.

Reference Example 6-2

$^1$H-NMR (CDCl$_3$) δ ppm: 1.40-1.50 (3H, m), 2.67 (3H, s), 3.76 (1H, br s), 3.94 (3H, s), 5.20-5.30 (3H, m), 7.20 (1H, s), 7.30-7.50 (6H, m)

Reference Example 6-3

$^1$H-NMR (CDCl$_3$) δ ppm: 2.35 (3H, s), 2.63 (3H, s), 3.94 (3H, s), 4.50-4.60 (1H, m), 4.90-5.10 (2H, m), 6.10-6.20 (1H, m), 6.76 (1H, s), 7.00-7.30 (9H, m), 7.48 (1H, br s)

Reference Example 6-4

$^1$H-NMR (CDCl$_3$) δ ppm: 0.76-1.18 (7H, m), 1.51-1.72 (3H, m), 1.95-1.99 (1H, m), 2.65 (3H, s), 3.20 (1H, d, J=5.5 Hz), 3.94 (3H, s), 4.76-5.81 (1H, m), 5.20-5.30 (2H, m), 7.07 (1H, s), 7.27-7.45 (6H, m)

Reference Example 6-6

$^1$H-NMR (CDCl$_3$) δ ppm: 1.40-1.50 (9H, m), 3.20-3.40 (1H, m), 3.94 (3H, s), 3.95-4.10 (1H, m), 5.00-5.20 (1H, m), 5.20-5.30 (2H, m), 7.19 (1H, s), 7.30-7.50 (6H, m)

Reference Example 6-7

$^1$H-NMR (CDCl$_3$) δ ppm: 1.00-1.10 (3H, m), 1.40-1.50 (3H, m), 1.80-2.00 (2H, m), 2.90-3.00 (2H, m), 3.90-4.00 (4H, m), 5.10-5.30 (3H, m), 7.19 (1H, s), 7.20-7.50 (6H, m)

Reference Example 7-1

1-[5-Benzyloxy-4-methoxy-2-(5-methyl-[1,2,4]oxadiazol-3-yl)phenyl]-2-methylpropan-1-ol A mixture of 3-(4-benzyloxy-2-iodo-5-methoxy-phenyl)-5-methyl-[1,2,4]oxadiazole (reference example 4-1) (844 mg) and tetrahydrofuran (6 mL) was cooled in an ice salt bath under an argon atmosphere. Isopropylmagnesium chloride (2.0 mol/L tetrahydrofuran solution, 1.2 mL) was added, and the mixture was stirred under ice-salt-bath cooling for 10 minutes. After an addition of isobutyraldehyde (0.55 mL), the mixture was stirred in an ice salt bath for 10 minutes, and at room temperature for 30 minutes. Water and 2 mol/L hydrochloric acid were added to the mixture, and the mixture was extracted with ethyl acetate. The separated organic layer was washed with brine, dried over anhydrous magnesium sulfate, and concentrated under reduced pressure. The residue was purified by silica gel column chromatography (eluent: 15%-35% ethyl acetate/hexane, gradient elution) to give the title compound (533 mg).

$^1$H-NMR (CDCl$_3$) δ ppm: 0.63 (3H, d, J=6.7 Hz), 0.98 (3H, d, J=6.7 Hz), 1.87-1.96 (1H, m), 2.66 (3H, s), 3.36 (1H, d, J=5.5 Hz), 3.94 (3H, s), 4.69-4.72 (1H, m), 5.21 (1H, d, J=12.3 Hz), 5.27 (1H, d, J=12.3 Hz), 7.10 (1H, s), 7.28-7.39 (3H, m), 7.44-7.46 (3H, m)

Reference examples 7-2 to 7-8 were prepared in a manner similar to those as described in Reference example 7-1 using the corresponding iodobenzenes and aldehydes or N,N-dimethyl-formamide instead of 3-(4-benzyloxy-2-iodo-5-methoxyphenyl)-5-methyl-[1,2,4]oxadiazole and isobutyraldehyde. These were illustrated in table 5.

TABLE 5

| Reference example | Structure |
|---|---|
| 7-1 | [Structure: 1-[5-Benzyloxy-4-methoxy-2-(5-methyl-[1,2,4]oxadiazol-3-yl)phenyl]-2-methylpropan-1-ol] |
| 7-2 | [Structure: pyridin-2-yl-(4-benzyloxy-5-methoxy-2-(5-methyl-1,2,4-oxadiazol-3-yl)phenyl)methanol] |
| 7-3 | [Structure: (2-fluorophenyl)-(4-benzyloxy-5-methoxy-2-(5-methyl-1,2,4-oxadiazol-3-yl)phenyl)methanol] |

TABLE 5-continued

| Reference example | Structure |
|---|---|
| 7-4 | (structure) |
| 7-5 | (structure) |
| 7-6 | (structure) |
| 7-7 | (structure) |
| 7-8 | (structure) |

The physical data of reference examples 7-2 to 7-3 and 7-5 to 7-8 were shown below.

Reference Example 7-2

$^1$H-NMR (CDCl$_3$) δ ppm: 2.66 (3H, s), 3.93 (3H, s), 4.95-5.15 (2H, m), 5.60 (1H, d, J=4.4 Hz), 6.50-6.60 (1H, m), 6.79 (1H, s), 7.10-7.40 (7H, m), 7.47 (1H, s), 7.50-7.65 (1H, m), 8.45-8.55 (1H, m)

Reference Example 7-3

MS (ESI, m/z): 391 (M+Na)+

Reference Example 7-5

$^1$H-NMR (CDCl$_3$) δ ppm: 1.92-2.01 (1H, m), 2.07-2.17 (1H, m), 2.57-2.66 (4H, m), 2.73-2.81 (1H, m), 3.68 (1H, d, J=5.0 Hz), 3.94 (3H, s), 5.01-5.06 (1H, m), 5.17-5.26 (2H, m), 7.12-7.46 (12H, m)

Reference Example 7-6

$^1$H-NMR (CDCl$_3$) δ ppm: 0.73 (9H, s), 2.25 (1H, bs), 2.64 (3H, s), 3.94 (3H, s), 5.21 (1H, d, J=12.6 Hz), 5.29 (1H, d, J=12.6 Hz), 5.45 (1H, bs), 7.21 (1H, s), 7.28-7.31 (1H, m), 7.33-7.38 (3H, m), 7.44-7.46 (2H, m)

Reference Example 7-7

$^1$H-NMR (CDCl$_3$) δ ppm: 2.61 (3H, s), 3.93 (3H, s), 4.57 (1H, d, J=5.2 Hz), 4.99-5.10 (4H, m), 6.13 (1H, d, J=5.2 Hz), 6.77 (1H, s), 6.88 (2H, d, J=8.7 Hz), 7.18 (2H, d, J=8.7 Hz), 7.23-7.47 (10H, m), 7.48 (1H, s)

Reference Example 7-8

$^1$H-NMR (CDCl$_3$) δ ppm: 0.33-0.39 (2H, m), 0.62-0.69 (2H, m), 1.22-1.35 (1H, m), 2.64 (3H, s), 3.80 (2H, d, J=7.0 Hz), 3.94 (3H, s), 4.56 (1H, d, J=5.5 Hz), 4.99-5.11 (2H, m), 6.11 (1H, d, J=5.5 Hz), 6.77 (1H, s), 6.81 (2H, d, J=8.6 Hz), 7.16 (2H, d, J=8.6 Hz), 7.25-7.34 (5H, m), 7.48 (1H, s)

Reference Example 8-1

5-Benzyloxy-4-methoxy-2-(5-methyl-[1,2,4]oxadiazol-3-yl)benzonitrile

A mixture of 3-(4-benzyloxy-2-iodo-5-methoxy-phenyl)-5-methyl-[1,2,4]oxadiazole (reference example 4-1) (500 mg), cuprous cyanide (424 mg), tris(dibenzylidene-acetone) dipalladium (0) (271 mg), tetraethylammonium cyanide (222 mg), 1,1'-bis(diphenylphosphino)ferrocene (525 mg) and 1,4-dioxane (12 mL) was stirred at 105° C. under an argon atmosphere for 2.5 hours. After cooling to room temperature, the mixture was passed through a layer of Celite (registered mark). The filtrate was concentrated under reduced pressure. The residue was purified by silica gel column chromatography (eluent: 25%-50% ethyl acetate/hexane, gradient elution) to give the title compound (231 mg).

$^1$H-NMR (CDCl$_3$) δ ppm: 2.69 (3H, s), 4.01 (3H, s), 5.21 (2H, s), 7.24 (1H, s), 7.30-7.50 (5H, m), 7.57 (1H, s)

Reference Example 9-1

1-[5-Benzyloxy-4-methoxy-2-(5-methyl-[1,2,4]oxadiazol-3-yl)phenyl]-2-phenylethanone A mixture of 5-benzyloxy-4-methoxy-2-(5-methyl-[1,2,4]oxadiazol-3-yl)benzoic acid (reference example 5-1) (817 mg), thionyl chloride (0.53 mL), N,N-dimethylformamide (1 drop) and toluene (10 mL) was stirred at 80° C. for 30 minutes. The mixture was concentrated under reduced pressure. Toluene was added to the residue, and the mixture was concentrated under reduced pressure to give 5-benzyloxy-4-methoxy-2-(5-methyl-[1,2,4]oxadiazol-3-yl)benzoyl chloride.

A mixture of 5-benzyloxy-4-methoxy-2-(5-methyl-[1,2,4]oxadiazol-3-yl)benzoyl chloride, benzylzinc bromide (0.5 mol/L, tetrahydrofuran solution, 4.4 mL), dichlorobis-(triphenylphosphine)palladium(II) (153 mg) and toluene (6 mL) was stirred at room temperature under an argon atmosphere for 5 hours. Ethyl acetate and 2 mol/L hydrochloric acid were added to the mixture. The separated organic layer was washed with water, an aqueous solution of sodium bicarbonate and brine successively, dried over anhydrous magnesium sulfate, and concentrated under reduced pressure. The residue was purified by silica gel column chromatography (eluent: 5%-20% ethyl acetate/hexane, gradient elution) to give the title compound (307 mg).

$^1$H-NMR (CDCl$_3$) δ ppm: 1.84 (3H, s), 3.29 (1H, d, J=14.2 Hz), 3.42 (1H, d, J=14.2 Hz), 3.91 (3H, s), 5.19-5.25 (2H, m), 7.11 (1H, s), 7.15-7.20 (3H, m), 7.26-7.28 (2H, m), 7.30 (1H, s), 7.32-7.45 (5H, m)

Reference Example 10-1

5-Benzyloxy-4-methoxy-2-(5-methyl-[1,2,4]oxadiazol-3-yl)-N-phenylbenzamide

To a mixture of 5-benzyloxy-4-methoxy-2-(5-methyl-[1,2,4]oxadiazol-3-yl)benzoic acid (reference example 5-1) (500 mg), benzotriazol-1-yloxytripyrrolidinephosphonium hexafluorophosphate (1.15 g), 1-hydroxybenzotriazole (20 mg), methylene chloride (3 mL) and N,N-dimethylformamide (3 mL) were added aniline (0.2 mL) and triethylamine (0.62 mL). After stirring at room temperature for 4 hours, ethyl acetate and 2 mol/L hydrochloric acid were added to the mixture. The separated organic layer was washed with a 2 mol/L aqueous solution of sodium hydroxide, an aqueous solution of sodium bicarbonate and brine successively, dried over anhydrous magnesium sulfate, and concentrated under reduced pressure. The residue was triturated with methanol to give the title compound (449 mg).

$^1$H-NMR (CDCl$_3$) δ ppm: 2.58 (3H, s), 3.96 (3H, s), 5.22 (2H, s), 7.11-7.14 (1H, m), 7.31-7.56 (11H, m), 8.03 (1H, br)

Reference examples 10-2 to 10-4 were prepared in a manner similar to those as described in Reference example 10-1 using the corresponding amines or alcohols instead of aniline. These were illustrated in table 6.

TABLE 6

| Reference example | Structure |
|---|---|
| 10-1 | 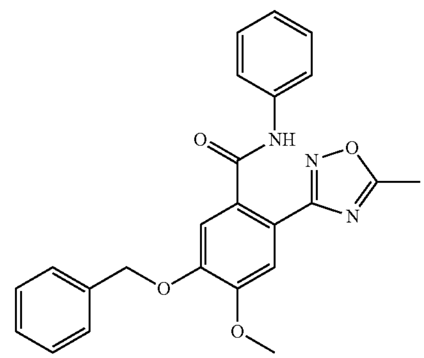 |
| 10-2 | 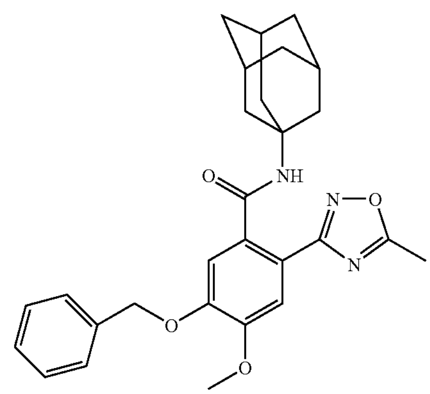 |
| 10-3 | 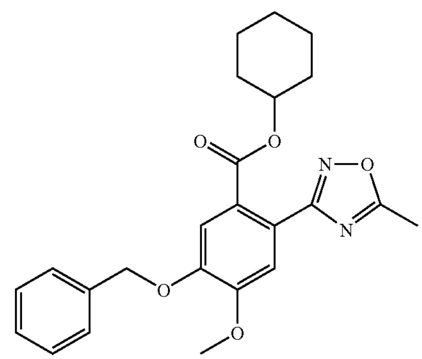 |
| 10-4 | 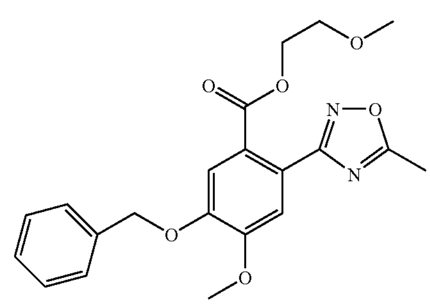 |

The physical data of reference examples 10-2 and 10-4 were shown below.

Reference Example 10-2

¹H-NMR (CDCl₃) δ ppm: 1.70 (6H, br s), 2.00-2.20 (9H, m), 2.63 (3H, s), 3.93 (3H, s), 5.20 (2H, s), 5.53 (1H, br s), 7.14 (1H, br s), 7.28 (1H, br s), 7.30-7.50 (5H, m)

Reference Example 10-4

¹H-NMR (CDCl₃) δ ppm: 2.63 (3H, s), 3.32 (3H, s), 3.50-3.60 (2H, m), 3.94 (3H, s), 4.20-4.40 (2H, m), 5.22 (2H, s), 7.14 (1H, s), 7.30-7.50 (6H, m)

Reference Example 11-1

Isopropyl 5-benzyloxy-4-methoxy-2-(5-methyl-[1,2,4]oxa-diazol-3-yl)benzoate

A mixture of 5-benzyloxy-4-methoxy-2-(5-methyl-[1,2,4]oxadiazol-3-yl)benzoic acid (reference example 5-1) (308 mg), 2-iodopropane (0.225 mL), potassium carbonate (312 mg) and N,N-dimethylformamide (2.6 mL) was stirred at 60° C. for 2.5 hours. After cooling to room temperature, water and ethyl acetate were added to the mixture. The separated organic layer was washed with water, dried over anhydrous magnesium sulfate, and concentrated under reduced pressure to give the title compound (342 mg).
¹H-NMR (CDCl₃) δ ppm: 1.10-1.25 (6H, m), 2.64 (3H, s), 3.93 (3H, s), 5.00-5.20 (1H, m), 5.23 (2H, s), 7.10 (1H, s), 7.33-7.50 (6H, m)

Reference Example 11-2

Ethyl 5-benzyloxy-4-methoxy-2-(5-methyl-[1,2,4]oxadiazol-3-yl)benzoate

The title compound was prepared in a manner similar to those as described in Reference example 11-1 using iodoethane instead of 2-iodopropane.
¹H-NMR (CDCl₃) δ ppm: 1.10-1.30 (3H, m), 2.64 (3H, s), 3.94 (3H, s), 4.20-4.30 (2H, m), 5.22 (2H, s), 7.13 (1H, s), 7.30-7.50 (6H, m)

Reference Example 12-1

Acetic Acid [5-benzyloxy-4-methoxy-2-(5-methyl-[1,2,4]-oxadiazol-3-yl)phenyl]tert-butylcarbamoylmethyl Ester A mixture of 5-benzyloxy-4-methoxy-2-(5-methyl-[1,2,4]oxadiazol-3-yl)benzaldehyde (Reference example 15-1) (453 mg), tert-butylisocyanide (465 mg), acetic acid (0.32 mL) and acetonitrile (8 mL) was stirred at 70° C. for 13 hours. After cooling to room temperature, ethyl acetate and water were added to the mixture. The separated organic layer was washed with water, an aqueous solution of sodium bicarbonate, and brine successively, dried over anhydrous magnesium sulfate, and concentrated under reduced pressure. The residue was purified by silica gel column chromatography (eluent: 15%-50% ethyl acetate/hexane, gradient elution) to give the title compound (604 mg).
¹H-NMR (CDCl₃) δ ppm: 1.26 (9H, s), 2.06 (3H, s), 2.69 (3H, s), 3.95 (3H, s), 5.21-5.30 (2H, m), 6.38 (1H, s), 7.27-7.50 (8H, m)

Reference Example 12-2

Acetic Acid [5-benzyloxy-4-methoxy-2-(5-methyl-[1,2,4]-oxadiazol-3-yl)phenyl]cyclohexylcarbamoylmethyl Ester The title compound was prepared in a manner similar to those as described in Reference example 12-1 using cyclohexyl isocyanide instead of tert-butyl isocyanide.
¹H-NMR (CDCl₃) δ ppm: 0.95-1.43 (5H, m), 1.48-1.71 (4H, m), 1.93-1.99 (1H, m), 2.07 (3H, s), 2.70 (3H, s), 3.67-3.76 (1H, m), 3.94 (3H, s), 5.20-5.30 (2H, m), 6.48 (1H, s), 7.28-7.50 (8H, m)

Reference Example 13-1

2-[5-Benzyloxy-4-methoxy-2-(5-methyl-[1,2,4]oxadiazol-3-yl)phenyl]N-tert-butyl-2-hydroxyacetamide A mixture of acetic acid [5-benzyloxy-4-methoxy-2-(5-methyl-[1,2,4]oxadiazol-3-yl)phenyl]-tert-butylcarbamoyl methyl ester (Reference example 12-1) (604 mg), a 5 mol/L aqueous solution of sodium hydroxide (1 mL) and methanol (8 mL) was stirred at room temperature for 1.5 hours. Ethyl acetate and water were added to the mixture. The separated organic layer was washed with water, an aqueous solution of sodium bicarbonate successively, dried over anhydrous magnesium sulfate, and concentrated under reduced pressure to give the title compound (552 mg).
MS (ESI, m/z): 426 (M+1)

Reference Example 13-2

2-[5-Benzyloxy-4-methoxy-2-(5-methyl-[1,2,4]oxadiazol-3-yl)phenyl]N-cyclohexyl-2-hydroxyacetamide The title compound was prepared in a manner similar to those as described in Reference example 13-1 using acetic acid [5-benzyloxy-4-methoxy-2-(5-methyl-[1,2,4]oxadiazol-3-yl)phenyl]cyclohexylcarbamoylmethyl ester (reference example 12-2) instead of acetic acid [5-benzyloxy-4-methoxy-2-(5-methyl-[1,2,4]oxadiazol-3-yl)phenyl]tert-butylcarbamoyl-methyl ester.
¹H-NMR (CDCl₃) δ ppm: 0.97-1.48 (5H, m), 1.54-1.95 (5H, m), 2.69 (3H, s), 3.71-3.80 (1H, m), 3.93 (3H, s), 4.84 (1H, d, J=5.5 Hz), 5.18 (2H, s), 5.51 (1H, d, J=5.5 Hz), 7.16 (1H, s), 7.29-7.47 (6H, m), 7.67 (1H, d, J=7.6 Hz)

Reference Example 14-1

[5-Benzyloxy-4-methoxy-2-(5-methyl-[1,2,4]oxadiazol-3-yl)phenyl]phenylmethanone

A mixture of [5-benzyloxy-4-methoxy-2-(5-methyl-[1,2,4]oxadiazol-3-yl]phenyl)phenylmethanol (reference example 6-1) (526 mg), manganese dioxide (1.18 g) and methylene chloride (6.8 mL) was stirred at room temperature overnight. After addition of manganese dioxide (1.18 g), the mixture was stirred for 7.5 hours, and manganese dioxide (0.59 g) was added, and the mixture was stirred overnight. The mixture was passed through a layer of Celite (registered mark). The filtrate was concentrated under reduced pressure to give the title compound (526 mg).
¹H-NMR (CDCl₃) δ ppm: 2.42 (3H, s), 4.01 (3H, s), 5.18 (2H, s), 7.06 (1H, s), 7.30-7.50 (9H, m), 7.60-7.70 (2H, m)

Reference Example 14-2

1-[5-Benzyloxy-4-methoxy-2-(5-methyl-[1,2,4]oxadiazol-3-yl)phenyl]ethanone

To a mixture of 1-[5-benzyloxy-4-methoxy-2-(5-methyl-[1,2,4]oxadiazol-3-yl)phenyl]ethanol (reference example 6-2) (467 mg), triethylamine (0.956 mL) and dimethyl sulfoxide (6 mL) was added a mixture of pyridine sulfur trioxide complex (655 mg) and dimethyl sulfoxide (2 mL). After stirring at room temperature for 2 hours, water and ethyl acetate were added to the mixture. The separated organic layer was washed with 2 mol/L hydrochloric acid and brine successively, dried over anhydrous magnesium sulfate, and concentrated under reduced pressure. The residue was purified by silica gel column chromatography (eluent: 25%-34% ethyl acetate/hexane, gradient elution) to give the title compound (365 mg).

$^1$H-NMR (CDCl$_3$) δ ppm: 2.38 (3H, s), 2.64 (3H, s), 3.96 (3H, s), 5.22 (2H, s), 7.13 (1H, s), 7.28 (1H, s), 7.30-7.50 (5H, m)

Reference examples 14-3 to 14-7 were prepared in a manner similar to those as described in Reference example 14-1 or Reference example 14-2 using the corresponding alcohols instead of [5-benzyloxy-4-methoxy-2-(5-methyl-[1,2,4]oxadiazole-3-yl)phenyl]phenylmethanol or 1-[5-benzyloxy-4-methoxy-2-(5-methyl-[1,2,4]oxadiazol-3-yl)phenyl]ethanol. These were illustrated in table 7.

TABLE 7

| Reference example | Structure |
|---|---|
| 14-1 | (structure) |
| 14-2 | (structure) |
| 14-3 | (structure) |
| 14-4 | (structure) |
| 14-5 | (structure) |
| 14-6 | (structure) |

TABLE 7-continued

| Reference example | Structure |
|---|---|
| 14-7 | |
| 14-8 | |
| 14-9 | |
| 14-10 | |
| 14-11 | 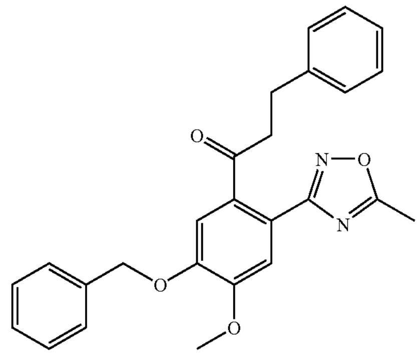 |
| 14-12 | 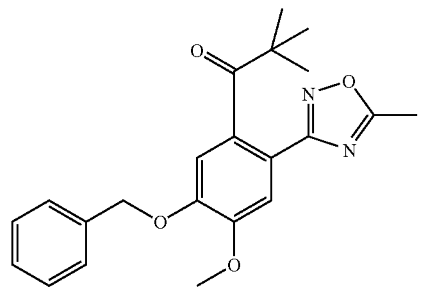 |
| 14-13 | 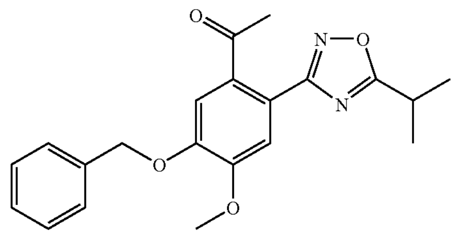 |
| 14-14 | 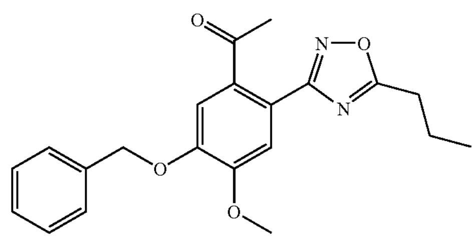 |
| 14-15 | 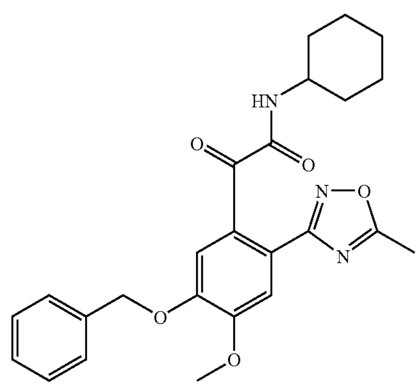 |

TABLE 7-continued

| Reference example | Structure |
|---|---|
| 14-16 | (structure shown) |
| 14-17 | (structure shown) |

The physical data of reference examples 14-3 to 14-17 were shown below.

Reference Example 14-3

$^1$H-NMR (CDCl$_3$) δ ppm: 1.06 (6H, d, J=6.8 Hz), 2.62 (3H, s), 2.79-2.86 (1H, m), 3.97 (3H, s), 5.22 (2H, s), 6.92 (1H, s), 7.29-7.44 (6H, m)

Reference Example 14-4

$^1$H-NMR (CDCl$_3$) δ ppm: 1.32 (9H, s), 2.60 (3H, s), 3.99 (3H, s), 5.19 (2H, s), 6.94 (1H, br), 7.18 (1H, s), 7.31-7.47 (6H, m)

Reference Example 14-5

$^1$H-NMR (CDCl$_3$) δ ppm: 2.37 (3H, s), 2.44 (3H, s), 4.01 (3H, s), 5.30 (2H, s), 7.03 (1H, s), 7.10-7.70 (10H, m)

Reference Example 14-6

$^1$H-NMR (CDCl$_3$) δ ppm: 2.38 (3H, s), 4.01 (3H, s), 5.21 (2H, s), 7.20-7.55 (8H, m), 7.75-7.85 (1H, m), 8.05-8.20 (1H, m), 8.35-8.50 (1H, m)

Reference Example 14-7

MS (ESI, m/z): 407 (M+1)

Reference Example 14-8

$^1$H-NMR (CDCl$_3$) δ ppm: 0.89-0.93 (2H, m), 1.18-1.22 (2H, m), 2.00-2.06 (1H, m), 2.63 (3H, s), 3.96 (3H, s), 5.22 (2H, s), 7.19 (1H, s), 7.29 (1H, s), 7.30-7.47 (5H, m)

Reference Example 14-9

$^1$H-NMR (CDCl$_3$) δ ppm: 2.45 (3H, s), 3.99 (3H, s), 5.18 (2H, s), 6.96-7.01 (1H, m), 7.08-7.12 (1H, m), 7.14 (1H, s), 7.31-7.45 (7H, m), 7.52-7.57 (1H, m)

Reference Example 14-10

$^1$H-NMR (CDCl$_3$) δ ppm: 2.45 (3H, s), 4.01 (3H, s), 5.22 (2H, s), 7.25-7.50 (6H, m), 7.51 (1H, s), 7.55-7.65 (1H, m), 7.75-7.85 (1H, m)

Reference Example 14-11

$^1$H-NMR (CDCl$_3$) δ ppm: 2.62 (3H, s), 2.93-3.02 (4H, m), 3.95 (3H, s), 5.14 (2H, s), 6.92 (1H, s), 7.13-7.44 (11H, m)

Reference Example 14-12

$^1$H-NMR (CDCl$_3$) δ ppm: 1.11 (9H, s), 2.59 (3H, s), 3.98 (3H, s), 5.22 (2H, s), 6.67 (1H, s), 7.28-7.43 (5H, m), 7.54 (1H, s)

Reference Example 14-13

$^1$H-NMR (CDCl$_3$) δ ppm: 1.40-1.50 (6H, m), 2.36 (3H, s), 3.20-3.40 (1H, m), 3.97 (3H, s), 5.22 (2H, s), 7.13 (1H, s), 7.29 (1H, s), 7.30-7.50 (5H, m)

Reference Example 14-14

$^1$H-NMR (CDCl$_3$) δ ppm: 1.00-1.10 (3H, m), 1.80-2.00 (2H, m), 2.36 (3H, s), 2.80-3.00 (2H, m), 3.96 (3H, s), 5.22 (2H, s), 7.13 (1H, s), 7.29 (1H, s), 7.30-7.50 (5H, m)

Reference Example 14-15

$^1$H-NMR (CDCl$_3$) δ ppm: 1.15-1.41 (5H, m), 1.60-1.88 (5H, m), 2.60 (3H, s), 3.58-3.67 (1H, m), 4.00 (3H, s), 5.19 (2H, s), 6.95 (1H, d, J=8.6 Hz), 7.21 (1H, s), 7.30-7.48 (6H, m)

Reference Example 14-16

$^1$H-NMR (CDCl$_3$) δ ppm: 2.44 (3H, s), 4.00 (3H, s), 5.10 (2H, s), 5.17 (2H, s), 6.89 (2H, d, J=9.0 Hz), 7.01 (1H, s), 7.27-7.44 (10H, m), 7.48 (1H, s), 7.66 (2H, d, J=9.0 Hz)

Reference Example 14-17

$^1$H-NMR (CDCl$_3$) δ ppm: 0.33-0.39 (2H, m), 0.62-0.70 (2H, m), 1.22-1.33 (1H, m), 2.46 (3H, s), 3.83 (2H, d, J=6.9 Hz), 4.01 (3H, s), 5.17 (2H, s), 6.81 (2H, d, J=9.0 Hz), 7.02 (1H, s), 7.28-7.44 (5H, m), 7.49 (1H, s), 7.66 (2H, d, J=9.0 Hz)

Reference Example 15-1

5-Benzyloxy-4-methoxy-2-(5-methyl-[1,2,4]oxadizol-3-yl)benzaldehyde

A mixture of 3-(4-benzyloxy-2-iodo-5-methoxyphenyl)-5-methyl-[1,2,4]oxadiazole (reference example 4-1) (3.52 g)

and tetrahydrofuran (35 mL) was cooled in an ice salt bath under an argon atmosphere. Isopropylmagnesium chloride (2.0 mol/L tetrahydrofuran solution, 5 mL) was added. After stirring under ice-bath cooling for 1 hour, N,N-dimethylformamide (1.28 mL) was added to the mixture. After stirring at room temperature overnight, water, 2 mol/L hydrochloric acid and ethyl acetate were added successively to the mixture. The separated organic layer was dried over anhydrous magnesium sulfate, and concentrated under reduced pressure. The residue was purified by silica gel column chromatography (eluent: 25%-34% ethyl acetate/hexane, gradient elution) to give the title compound (1.83 g).

$^1$H-NMR (CDCl$_3$) δ ppm: 2.69 (3H, s), 4.02 (3H, s), 5.25 (2H, s), 7.30-7.50 (6H, m), 7.67 (1H, s), 10.58 (1H, s)

Reference examples 15-2 to 15-14 were prepared in a manner similar to those as described in Reference Example 15-1 using the corresponding halobenzenes and N,N-dimethylformamide, acid anhydrides, acid chlorides or N-methoxy-N-methylamides instead of 3-(4-benzyloxy-2-iodo-5-methoxyphenyl)-5-methyl-[1,2,4]-oxadiazole and N,N-dimethylformamide. These were illustrated in table 8.

TABLE 8

| Reference example | Structure |
|---|---|
| 15-1 | 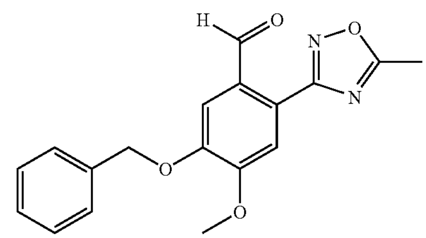 |
| 15-2 | 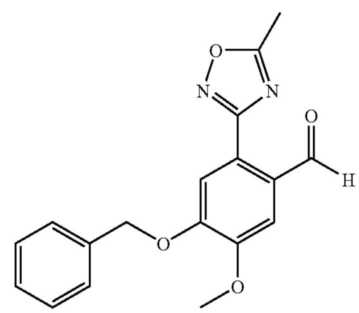 |
| 15-3 | 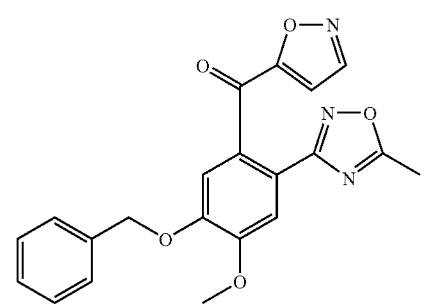 |
| 15-4 | 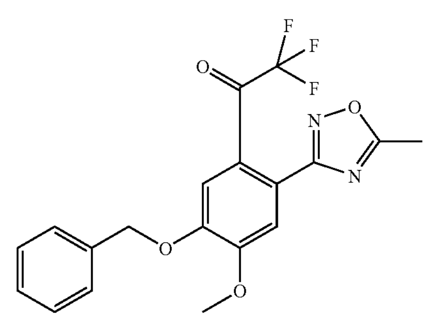 |

TABLE 8-continued

| Reference example | Structure |
|---|---|
| 15-5 | (structure) |
| 15-6 | (structure) |
| 15-7 | (structure) |
| 15-8 | (structure) |
| 15-9 | (structure) |
| 15-10 | (structure) |

TABLE 8-continued

| Reference example | Structure |
|---|---|
| 15-11 | 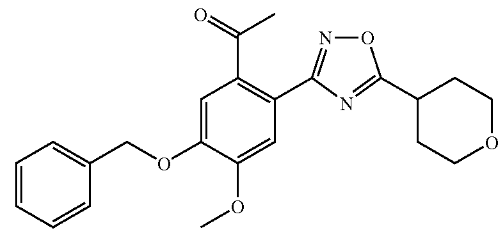 |
| 15-12 | 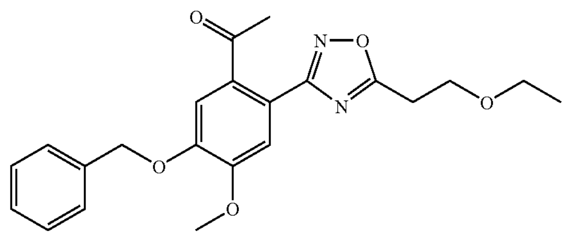 |
| 15-13 | 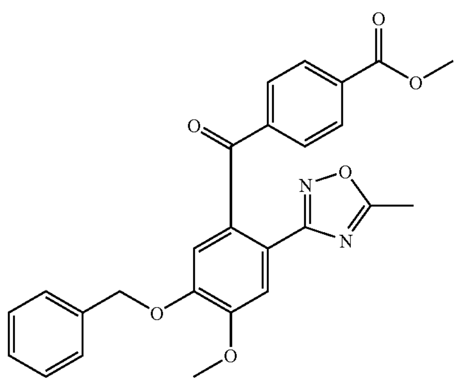 |
| 15-14 | 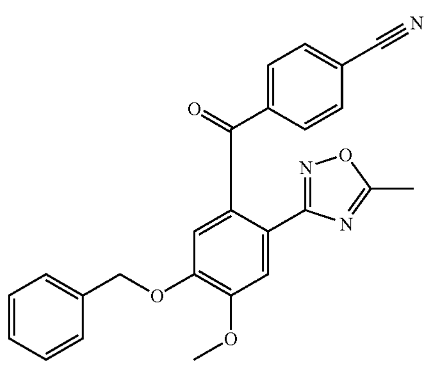 |

The physical data of reference examples 15-2 to 15-14 were shown below.

Reference Example 15-2

$^1$H-NMR (CDCl$_3$) δ ppm: 2.68 (3H, s), 3.99 (3H, s), 2.27 (2H, s), 7.30-7.50 (5H, m), 7.56 (1H, s), 7.62 (1H, s), 10.61 (1H, s)

Reference Example 15-3

$^1$H-NMR (CDCl$_3$) δ ppm: 2.50 (3H, s), 4.03 (3H, s), 5.23 (2H, s), 6.67 (1H, d, J=1.7 Hz), 7.21 (1H, s), 7.30-7.50 (5H, m), 7.51 (1H, s), 8.23 (1H, d, J=1.7 Hz)

Reference Example 15-4

$^1$H-NMR (CDCl$_3$) δ ppm: 2.63 (3H, s), 4.00 (3H, s), 5.21 (2H, s), 7.12 (1H, s), 7.25-7.55 (6H, m)

Reference Example 15-5

MS (ESI, m/z): 431 (M+1)

Reference Example 15-6

$^1$H-NMR (CDCl$_3$) δ ppm: 2.35 (3H, s), 3.96 (3H, s), 5.23 (2H, s), 5.34 (2H, s), 6.95-7.10 (3H, m), 7.14 (1H, s), 7.20-7.60 (8H, m)

Reference Example 15-7

¹H-NMR (CDCl₃) δ ppm: 1.40-1.50 (6H, m), 3.20-3.40 (1H, m), 4.02 (3H, s), 5.25 (2H, s), 7.30-7.50 (6H, m), 7.67 (1H, s), 10.59 (1H, s)

Reference Example 15-8

¹H-NMR (CDCl₃) δ ppm: 1.00-1.10 (3H, m), 1.90-2.00 (2H, m), 2.90-3.00 (2H, m), 4.02 (3H, s), 5.25 (2H, s), 7.30-7.50 (6H, m), 7.67 (1H, s), 10.59 (1H, s)

Reference Example 15-9

¹H-NMR (CDCl₃) δ ppm: 1.27 (3H, t, J=7.1 Hz), 2.35 (3H, s), 2.90 (2H, t, J=7.2 Hz), 3.24 (2H, t, J=7.2 Hz), 3.96 (3H, s), 4.18 (2H, q, J=7.1 Hz), 5.21 (2H, s), 7.11 (1H, s), 7.29 (1H, s), 7.25-7.50 (5H, m)

Reference Example 15-10

¹H-NMR (CDCl₃) δ ppm: 2.44 (3H, s), 3.98 (3H, s), 5.25 (2H, s), 7.21 (1H, s), 7.25 (1H, s), 7.30-7.50 (5H, m)

Reference Example 15-11

¹H-NMR (CDCl₃) δ ppm: 1.95-2.15 (4H, m), 2.37 (3H, s), 3.19-3.30 (1H, m), 3.52-3.62 (2H, m), 3.97 (3H, s), 4.00-4.08 (2H, m), 5.22 (2H, s), 7.13 (1H, s), 7.29 (1H, s), 7.30-7.50 (5H, m)

Reference Example 15-12

¹H-NMR (CDCl₃) δ ppm: 1.19 (3H, d, J=7.0 Hz), 2.36 (3H, s), 3.21 (2H, t, J=6.6 Hz), 3.54 (2H, q, J=7.0 Hz), 3.89 (2H, t, J=6.6 Hz), 3.96 (3H, s), 5.22 (2H, s), 7.13 (1H, s), 7.29 (1H, s), 7.30-7.50 (5H, m)

Reference Example 15-13

¹H-NMR (CDCl₃) δ ppm: 2.42 (3H, s), 3.93 (3H, s), 4.02 (3H, s), 5.19 (2H, s), 7.06 (1H, s), 7.30-7.44 (5H, m), 7.49 (1H, s), 7.71 (2H, d, J=8.6 Hz), 7.98 (2H, d, J=8.6 Hz)

Reference Example 15-14

¹H-NMR (CDCl₃) δ ppm: 2.44 (3H, s), 4.02 (3H, s), 5.20 (2H, s), 7.04 (1H, s), 7.30-7.46 (5H, m), 7.50 (1H, s), 7.61 (2H, d, J=8.8 Hz), 7.73 (2H, d, J=8.8 Hz)

Reference Example 16-1

Methyl 5-benzyloxy-4-methoxy-2-(5-methyl-[1,2,4]oxadiazol-3-yl)benzoate

A mixture of tris(dibenzylideneacetone)dipalladium (0) (163 mg), 1,1'-bis(diphenylphosphino)ferrocene (394 mg) and N,N-dimethylformamide (10 mL) was stirred under an argon atmosphere for 10 minutes. 3-(4-Benzyloxy-2-iodo-5-methoxy-phenyl)-5-methyl-[1,2,4]oxadiazole (reference example 4-1) (1.5 g), methanol (15 mL) and triethylamine (1.5 mL) were added to the mixture. After displacement to a carbon monoxide atmosphere, the mixture was stirred at 90° C. for 16 hours. After cooling to room temperature, ethyl acetate and 2 mol/L hydrochloric acid were added to the mixture. The separated organic layer was washed with water, a 2 mol/L aqueous solution of sodium hydroxide, an aqueous solution of sodium bicarbonate and brine successively, dried over anhydrous magnesium sulfate, and concentrated under reduced pressure. The residue was purified by silica gel column chromatography (eluent: 15%-30% ethyl acetate/hexane, gradient elution) to give the title compound (1.1 g).

¹H-NMR (CDCl₃) δ ppm: 2.65 (3H, s), 3.77 (3H, s), 3.94 (3H, s), 5.21 (2H, s), 7.16 (1H, s), 7.31-7.47 (6H, m)

Reference examples 16-2 to 16-4 were prepared in a manner similar to those as described in Reference Example 16-1 using the corresponding iodobenzenes instead of 3-(4-benzyloxy-2-iodo-5-methoxyphenyl)-5-methyl-[1,2,4]oxadiazole. These were illustrated in table 9.

TABLE 9

| Reference example | Structure |
|---|---|
| 16-1 | *methyl 5-benzyloxy-4-methoxy-2-(5-methyl-[1,2,4]oxadiazol-3-yl)benzoate* |
| 16-2 | *methyl 5-benzyloxy-2-(5-cyclopropyl-[1,2,4]oxadiazol-3-yl)-4-methoxybenzoate* |
| 16-3 | *methyl 5-benzyloxy-4-methoxy-2-(5-methoxymethyl-[1,2,4]oxadiazol-3-yl)benzoate* |
| 16-4 | *methyl 5-benzyloxy-2-(5-tert-butyl-[1,2,4]oxadiazol-3-yl)-4-methoxybenzoate* |

The physical data of reference examples 16-2 to 16-4 were shown below.

Reference Example 16-2

$^1$H-NMR (CDCl$_3$) δ ppm: 1.22-1.30 (4H, m), 2.21-2.27 (1H, m), 3.76 (3H, s), 3.94 (3H, s), 5.21 (2H, s), 7.15 (1H, s), 7.31-7.46 (6H, m)

Reference Example 16-3

$^1$H-NMR (CDCl$_3$) δ ppm: 3.56 (3H, s), 3.77 (3H, s), 3.95 (3H, s), 4.76 (2H, s), 5.22 (2H, s), 7.17 (1H, s), 7.32-7.47 (5H, m), 7.49 (1H, s)

Reference Example 16-4

$^1$H-NMR (CDCl$_3$) δ ppm: 1.49 (9H, s), 3.73 (3H, s), 3.95 (3H, s), 5.21 (2H, s), 7.18 (1H, s), 7.30-7.46 (6H, m)

Reference Example 17-1

3-(4-Benzyloxy-5-methoxy-2-trifluoromethylphenyl)-5-methyl-[1,2,4]oxadiazole

A mixture of 3-(4-benzyloxy-2-iodo-5-methoxyphenyl)-5-methyl-[1,2,4]oxadiazole (reference example 4-1), methyl fluorosulfonyldifluoroacetate (0.59 mL), copper(I) iodide (88 mg) and N,N-dimethylformamide (8 mL) was stirred at 90° C. for 3.5 hours. After cooling to room temperature, ethyl acetate was added to the mixture. The mixture was passed through a layer of Celite (registered mark). The filtrate was washed with an aqueous solution of sodium hydroxide, an aqueous solution of sodium bicarbonate and brine successively, dried over anhydrous magnesium sulfate, and concentrated under reduced pressure. The residue was purified by silica gel column chromatography (eluent: 10%-40% ethylacetate/hexane, gradient elution) to give the title compound (522 mg).

$^1$H-NMR (CDCl$_3$) δ ppm: 2.67 (3H, s), 3.95 (3H, s), 5.22 (2H, s), 7.25 (1H, s), 7.31 (1H, s), 7.32-7.47 (5H, m)

Reference Example 18-1

2-[5-Benzyloxy-4-methoxy-2-(5-methyl-[1,2,4]oxadiazol-3-yl)phenyl]N-cyclohexyl-N-methyl-2-oxoacetamide Mixture of 2-[5-benzyloxy-4-methoxy-2-(5-methyl-[1,2,4]oxadiazol-3-yl)phenyl]N-cyclohexyl-2-oxoacetamide (reference example 14-15) (860 mg) and N,N-dimethylformamide (6 mL) was added sodium hydride (60%, 92 mg). After stirring at room temperature for 20 minutes, iodomethane (0.48 mL) was added to the mixture. After stirring at room temperature for 8 hours, the mixture was poured into a mixture of 2 mol/L hydrochloric acid and ice-water. Ethyl acetate was added to the mixture. The separated organic layer was washed with water, an aqueous solution of sodium bicarbonate and brine successively, dried over anhydrous magnesium sulfate, and concentrated under reduced pressure. The residue was purified by silica gel column chromatography (eluent: 0%-50% ethyl acetate/hexane, gradient elution) to give the title compound (605 mg).

MS (ESI, m/z): 464 (M+1)

Reference Example 19-1

5-Methanesulfonyl-2-methoxy-4-(5-methyl-[1,2,4]oxadiazol-3-yl)phenol

A mixture of 3-(4-benzyloxy-2-iodo-5-methoxyphenyl)-5-methyl-[1,2,4]oxadiazole (reference example 4-1) (0.7 g), triisopropylsilanethiol (0.391 mL), tris(dibenzylidene-acetone)dipalladium (0) (152 mg), (oxydi-2,1-phenylene)bis-(diphenylphosphine) (90 mg), sodium bis(trimethylsilyl)amide (1.0 mol/L tetrahydrofuran solution, 0.39 mL) and toluene (20 mL) was stirred at 80° C. under argon atmosphere for 2 hours. After cooling to room temperature, Florisil (registered mark) (1 g) was added to the mixture. After stirring for 10 minutes, the mixture was passed through a layer of Celite (registered mark). The filtrate was concentrated under reduced pressure to give 3-(4-benzyloxy-5-methoxy-2-triisopropylsilanylsulfanyl-phenyl)-5-methyl-[1,2,4]oxadiazole.

A mixture of 3-(4-benzyloxy-5-methoxy-2-triisopropylsilanylsulfanylphenyl)-5-methyl-[1,2,4]oxadiazole, iodomethane (0.155 mL), cesium fluoride (756 mg) and N,N-dimethylformamide (20 mL) was stirred at room temperature for 30 minutes. Water and ethyl acetate were added to the mixture. The separated organic layer was washed with water, dried over anhydrous magnesium sulfate, and concentrated under reduced pressure to give 3-(4-benzyloxy-5-methoxy-2-methyl-sulfanylphenyl)-5-methyl-[1,2,4]oxadiazole.

A mixture of 3-(4-benzyloxy-5-methoxy-2-methylsulfanyl-phenyl)-5-methyl-[1,2,4]oxadiazole, m-chloroperbenzoic acid (60%, 1.43 g) and methylene chloride (30 mL) was stirred overnight. An aqueous solution of sodium hydrogen sulfite and methylene chloride were added to the mixture. The separated organic layer was washed with a 2 mol/L aqueous solution of sodium hydroxide and brine successively, dried over anhydrous magnesium sulfate, and concentrated under reduced pressure to give 3-(4-benzyloxy-2-methanesulfonyl-5-methoxyphenyl)-5-methyl-[1,2,4]oxa-diazole.

To a mixture of 3-(4-benzyloxy-2-methanesulfonyl-5-methoxyphenyl)-5-methyl-[1,2,4]oxadiazole and methylene chloride (20 mL) was added titanium(IV) chloride (0.472 g). After stirring at room temperature for 15 minutes, 2 mol/L hydrochloric acid and methylene chloride were added to the mixture. The separated organic layer was concentrated under reduced pressure. The residue was purified by silica gel column chromatography (eluent: 10%-100% ethylacetate/hexane, gradient elution) to give the title compound (112 mg).

$^1$H-NMR (CDCl$_3$) δ ppm: 2.67 (3H, s), 3.42 (3H, s), 3.99 (3H, s), 7.18 (1H, s), 7.76 (1H, s)

Reference Example 20-1

5-Hydroxy-4-methoxy-N,N-dimethyl-2-(5-methyl-[1,2,4]oxa-diazol-3-yl)benzenesulfonamide A mixture of 3-(4-benzyloxy-2-iodo-5-methoxyphenyl)-5-methyl-[1,2,4]oxadiazole (reference example 4-1) (0.7 g), triisopropylsilanethiol (0.391 mL), tris(dibenzylidene-acetone)dipalladium (0) (152 mg), (oxydi-2,1-phenylene)bis-(diphenylphosphine) (90 mg), sodium bis(trimethylsilyl)amide (1.0 mol/L tetrahydrofuran solution, 0.39 mL) and toluene (20 mL) was stirred at 80° C. for 2 hours under an argon atmosphere. After cooling to room temperature, Florisil (registered mark) (1 g) was added to the mixture. After stirring for 10 minutes, the mixture was passed through a layer of Celite (registered mark). The filtrate was concentrated under reduced pressure to give 3-(4-benzyloxy-5-methoxy-2-triisopropylsilanylsulfanyl-phenyl)-5-methyl-[1,2,4]oxadiazole.

To a mixture of 3-(4-benzyloxy-5-methoxy-2-triisopropylsilanylsulfanylphenyl)-5-methyl-[1,2,4]oxadiazole, sodium nitrate (352 mg) and acetonitrile (16 mL) was added sulfuryl chloride (0.336 mL) under ice-bath cooling. After stirring at room temperature for 1 hour, the mixture was poured into ice-water. Ethyl acetate was added to the mixture. The separated organic layer was dried over anhydrous magnesium sulfate, and concentrated under reduced pressure to give 5-benzyloxy-4-methoxy-2-(5-methyl-[1,2,4]oxadiazol-3-yl) benzenesulfonyl chloride.

To a mixture of 5-benzyloxy-4-methoxy-2-(5-methyl-[1,2,4]oxadiazol-3-yl)benzenesulfonylchloride, dimethyl-amine hydrochloride (203 mg) and tetrahydrofuran (20 mL) was added triethylamine (0.693 mL) under ice-bath cooling. After stirring at room temperature overnight, 2 mol/L hydrochloric acid was added to the mixture. The separated organic layer was washed with 2 mol/L hydrochloric acid and brine successively, dried over anhydrous magnesium sulfate, and concentrated under reduced pressure to give 5-benzyloxy-4-methoxy-N,N-dimethyl-2-(5-methyl-[1,2,4]oxadiazol-3-yl) benzenesulfonamide.

To a mixture of 5-benzyloxy-4-methoxy-N,N-dimethyl-2-(5-methyl-[1,2,4]oxadiazol-3-yl)benzenesulfonamide and methylene chloride (20 mL) was added titanium(IV) chloride (0.472 g) under ice-bath cooling. After stirring at room temperature overnight, 2 mol/L hydrochloric acid and methylene chloride were added to the mixture. The separated organic layer was washed with 2 mol/L hydrochloric acid and brine successively, and concentrated under reduced pressure. The residue was purified by silica gel column chromatography (eluent: 10%-100% ethyl acetate/hexane, gradient elution) to give the title compound (121 mg).

$^1$H-NMR (CDCl$_3$) δ ppm: 2.66 (3H, s), 2.78 (6H, s), 3.95 (3H, s), 6.95 (1H, s), 7.50 (1H, s)

Reference Example 21-1

[5-Hydroxy-4-methoxy-2-(5-methyl-[1,2,4]oxadiazol-3-yl)phenyl]phenylmethanone

To a mixture of [5-benzyloxy-4-methoxy-2-(5-methyl-[1,2,4]oxadiazol-3-yl)phenyl]phenylmethanone (reference example 14-1) (526 mg) and methylene chloride (22 mL) was added titanium(IV) chloride (0.288 mL) at room temperature. After stirring for 30 minutes, 2 mol/L hydrochloric acid and ethyl acetate were added to the mixture at room temperature. The separated organic layer was dried over anhydrous magnesium sulfate, and concentrated under reduced pressure. The residue was purified by silica gel column chromatography (eluent: 50%-67% ethyl acetate/hexane, gradient elution) to give the title compound (383 mg).

$^1$H-NMR (CDCl$_3$) δ ppm: 2.44 (3H, s), 4.03 (3H, s), 5.93 (1H, s), 7.07 (1H, s), 7.30-7.80 (6H, m)

Reference examples 21-2 to 21-45 were prepared in a manner similar to those as described in Reference example 21-1 using the corresponding benzyl ethers instead of [5-benzyloxy-4-methoxy-2-(5-methyl-[1,2,4]oxadiazol-3-yl)phenyl]phenyl-methanone. These were illustrated in table 10.

TABLE 10

| Reference example | Structure |
|---|---|
| 21-1 | 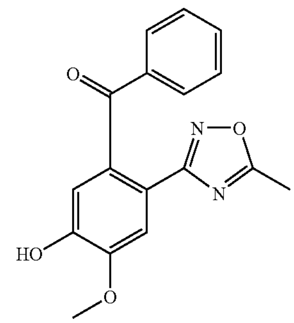 |
| 21-2 | 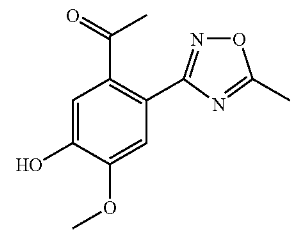 |
| 21-3 | 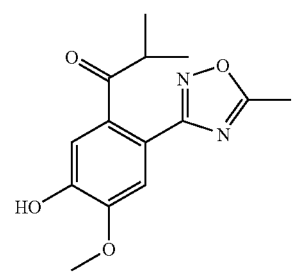 |
| 21-4 | 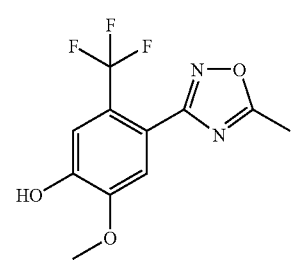 |
| 21-5 | 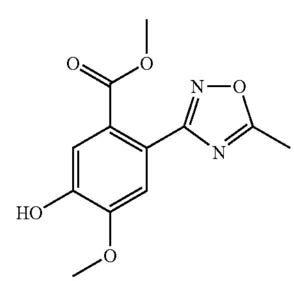 |

TABLE 10-continued

| Reference example | Structure |
|---|---|
| 21-6 | 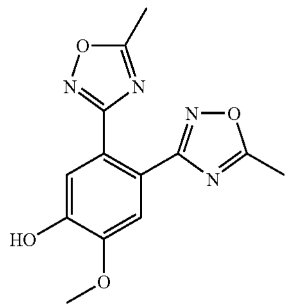 |
| 21-7 | 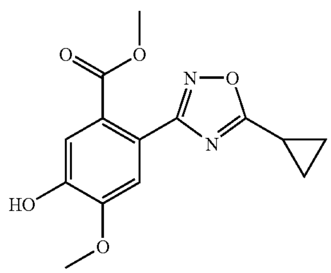 |
| 21-8 | 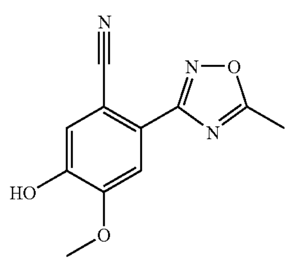 |
| 21-9 | 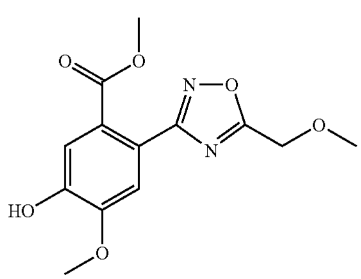 |
| 21-10 | 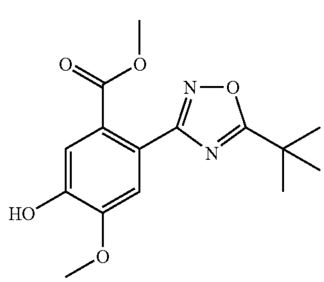 |
| 21-11 | |
| 21-12 | |
| 21-13 | |
| 21-14 | |

TABLE 10-continued

| Reference example | Structure |
|---|---|
| 21-15 | |
| 21-16 | |
| 21-17 | |
| 21-18 | |
| 21-19 | 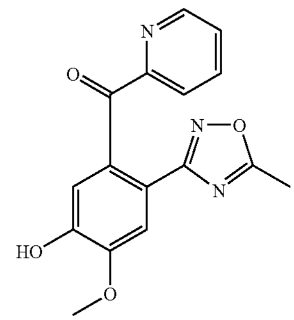 |
| 21-20 | 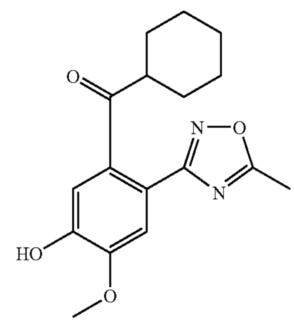 |
| 21-21 | 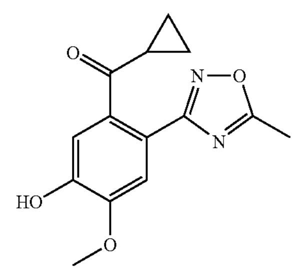 |
| 21-22 | 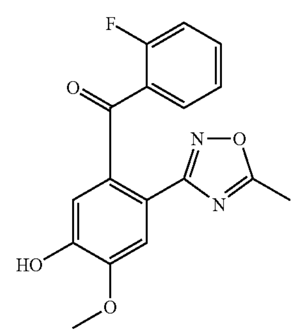 |
| 21-23 | 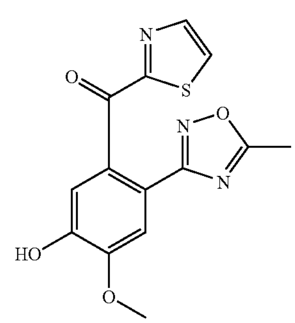 |

TABLE 10-continued

| Reference example | Structure |
|---|---|
| 21-24 | |
| 21-25 | |
| 21-26 | |
| 21-27 | |
| 21-28 | 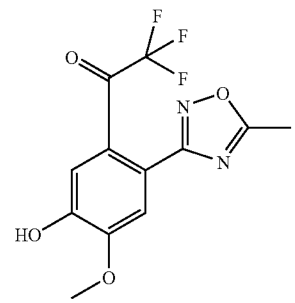 |
| 21-29 | 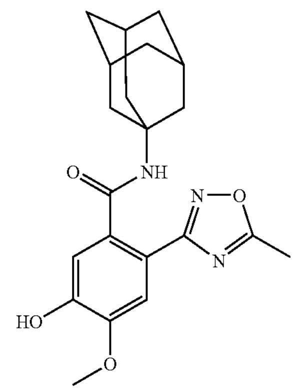 |
| 21-30 | 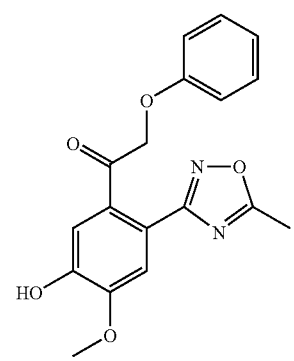 |
| 21-31 | 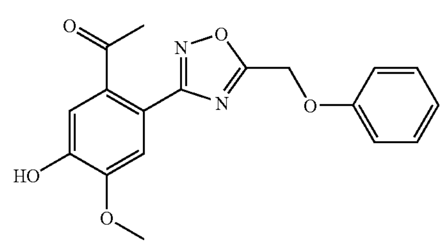 |
| 21-32 | 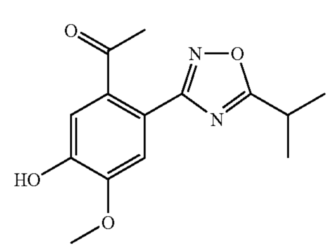 |

TABLE 10-continued

| Reference example | Structure |
|---|---|
| 21-33 | 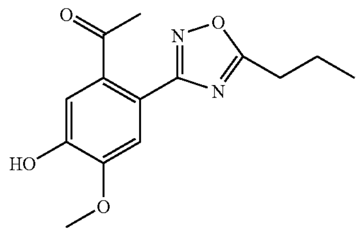 |
| 21-34 | 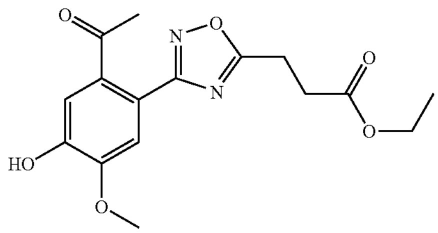 |
| 21-35 | 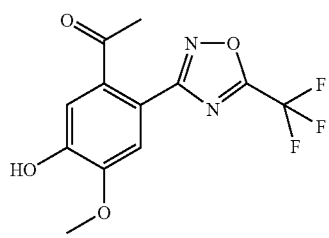 |
| 21-36 | 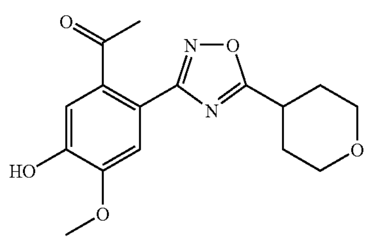 |
| 21-37 | 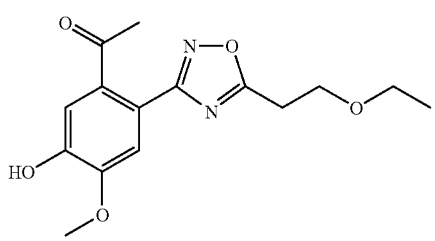 |
| 21-38 | 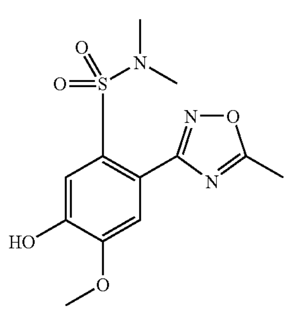 |
| 21-39 | 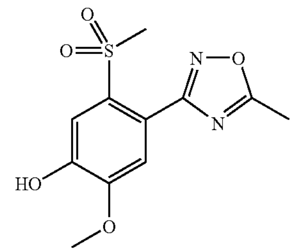 |
| 21-40 | 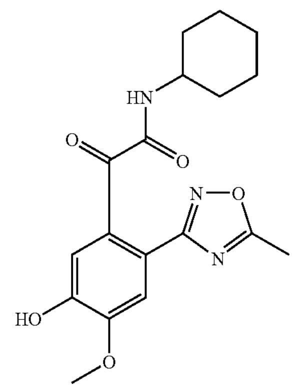 |
| 21-41 | 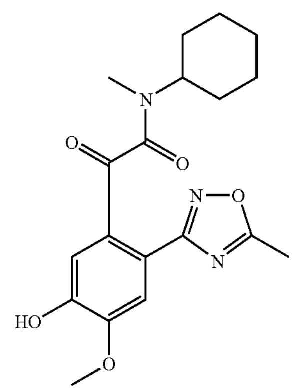 |
| 21-42 | 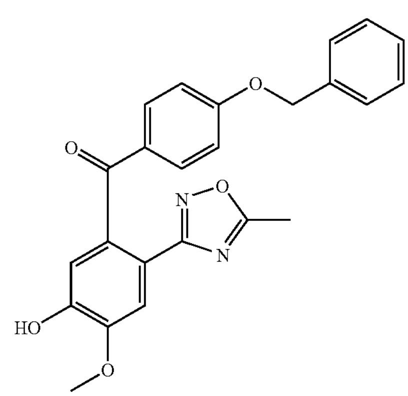 |

TABLE 10-continued

| Reference example | Structure |
|---|---|
| 21-43 | 4-hydroxy-5-methoxy-2-(5-methyl-1,2,4-oxadiazol-3-yl)phenyl (4-(cyclopropylmethoxy)phenyl) ketone |
| 21-44 | methyl 4-(4-hydroxy-5-methoxy-2-(5-methyl-1,2,4-oxadiazol-3-yl)benzoyl)benzoate |
| 21-45 | 4-(4-hydroxy-5-methoxy-2-(5-methyl-1,2,4-oxadiazol-3-yl)benzoyl)benzonitrile |

The physical data of reference examples 21-2 to 21-35 and 21-37 to 21-45 were shown below.

Reference Example 21-2

$^1$H-NMR (CDCl$_3$) δ ppm: 2.48 (3H, s), 2.63 (3H, s), 3.98 (3H, s), 5.90 (1H, s), 7.17 (1H, s)

Reference Example 21-3

$^1$H-NMR (CDCl$_3$) δ ppm: 1.16 (6H, d, J=7.0 Hz), 2.62 (3H, s), 2.90-3.00 (1H, m), 3.99 (3H, s), 5.91 (1H, s), 7.01 (1H, s), 7.38 (1H, s)

Reference Example 21-4

$^1$H-NMR (CDCl$_3$) δ ppm: 2.67 (3H, s), 3.98 (3H, s), 5.90 (1H, s), 7.24 (1H, s), 7.36 (1H, s)

Reference Example 21-5

$^1$H-NMR (CDCl$_3$) δ ppm: 2.64 (3H, s), 3.80 (3H, s), 3.97 (3H, s), 5.85 (1H, s), 7.17 (1H, s), 7.44 (1H, s)

Reference Example 21-6

$^1$H-NMR (CDCl$_3$) δ ppm: 2.59 (3H, s), 2.60 (3H, s), 4.00 (3H, s), 5.88 (1H, s), 7.34 (1H, s), 7.39 (1H, s)

Reference Example 21-7

$^1$H-NMR (CDCl$_3$) δ ppm: 1.21-1.29 (4H, m), 2.21-2.27 (1H, m), 3.78 (3H, s), 3.96 (3H, s), 5.83 (1H, s), 7.16 (1H, s), 7.42 (1H, s)

Reference Example 21-8

$^1$H-NMR (CDCl$_3$) δ ppm: 2.69 (3H, s), 4.04 (3H, s), 5.96 (1H, s), 7.33 (1H, s), 7.57 (1H, s)

Reference Example 21-9

$^1$H-NMR (CDCl$_3$) δ ppm: 3.55 (3H, s), 3.79 (3H, s), 3.97 (3H, s), 4.74 (2H, s), 5.87 (1H, s), 7.18 (1H, s), 7.46 (1H, s)

Reference Example 21-10

$^1$H-NMR (CDCl$_3$) δ ppm: 1.49 (9H, s), 3.76 (3H, s), 3.98 (3H, s), 5.84 (1H, s), 7.19 (1H, s), 7.42 (1H, s)

Reference Example 21-11

$^1$H-NMR (CDCl$_3$) δ ppm: 1.20-1.26 (6H, m), 2.64 (3H, s), 3.96 (3H, s), 5.00-5.20 (1H, m), 5.86 (1H, s), 7.11 (1H, s), 7.46 (1H, s)

Reference Example 21-12

$^1$H-NMR (CDCl$_3$) δ ppm: 1.30-1.90 (10H, m), 2.63 (3H, s), 3.96 (3H, s), 4.80-5.00 (1H, m), 5.83 (1H, s), 7.10 (1H, s), 7.48 (1H, s)

Reference Example 21-13

$^1$H-NMR (CDCl$_3$) δ ppm: 2.63 (3H, s), 3.35 (3H, s), 3.50-3.60 (2H, m), 3.96 (3H, s), 4.30-4.40 (2H, m), 5.89 (1H, s), 7.14 (1H, s), 7.48 (1H, s)

Reference Example 21-14

$^1$H-NMR (CDCl$_3$) δ ppm: 1.20-1.30 (3H, m), 2.64 (3H, s), 3.96 (3H, s), 4.20-4.30 (2H, m), 5.84 (1H, s), 7.14 (1H, s), 7.47 (1H, s)

Reference Example 21-15

$^1$H-NMR (CDCl$_3$) δ ppm: 1.21 (9H, s), 2.60 (3H, s), 3.90 (3H, s), 7.04 (1H, s), 7.30 (1H, s), 7.98 (1H, br), 10.10 (1H, s)

Reference Example 21-16

MS (ESI, m/z): 249 (M−1)

Reference Example 21-17

$^1$H-NMR (CDCl$_3$) δ ppm: 2.39 (3H, s), 2.47 (3H, s), 4.08 (3H, s), 7.10-7.30 (2H, m), 7.60-7.70 (2H, m), 7.79 (1H, s), 10.70 (1H, br s)

Reference Example 21-18

$^1$H-NMR (CDCl$_3$) δ ppm: 2.57 (3H, s), 3.87 (3H, s), 7.02 (1H, s), 7.04-7.07 (1H, m), 7.28-7.32 (2H, m), 7.35 (1H, s), 7.61-7.63 (2H, m), 10.01 (1H, s), 10.23 (1H, br)

Reference Example 21-19

$^1$H-NMR (CDCl$_3$) δ ppm: 2.39 (3H, s), 4.03 (3H, s), 5.94 (1H, brs), 7.12 (1H, s), 7.25-7.40 (1H, m), 7.49 (1H, s), 7.75-7.90 (1H, m), 8.10-8.20 (1H, m), 8.40-8.55 (1H, m)

Reference Example 21-20

$^1$H-NMR (CDCl$_3$) δ ppm: 1.16-1.24 (3H, m), 1.40-1.48 (2H, m), 1.63-1.93 (5H, m), 2.61 (3H, s), 2.63-2.71 (1H, m), 3.98 (3H, s), 5.88 (1H, s), 7.00 (1H, s), 7.38 (1H, s)

Reference Example 21-21

$^1$H-NMR (CDCl$_3$) δ ppm: 1.11-1.14 (2H, m), 1.43-1.46 (2H, m), 2.09-2.15 (1H, m), 2.64 (3H, s), 4.04 (3H, s), 7.64 (1H, s), 10.26 (1H, s)

Reference Example 21-22

$^1$H-NMR (CDCl$_3$) δ ppm: 2.47 (3H, s), 4.02 (3H, s), 5.90 (1H, s), 7.00-7.05 (1H, m), 7.12 (1H, s), 7.12-7.17 (1H, m), 7.39 (1H, s), 7.42-7.48 (1H, m), 7.63-7.67 (1H, m)

Reference Example 21-23

$^1$H-NMR (CDCl$_3$) δ ppm: 2.45 (3H, s), 4.03 (3H, s), 5.94 (1H, s), 7.31 (1H, s), 7.51 (1H, s), 7.62 (1H, d, J=3.0 Hz), 7.84 (1H, d, J=3.0 Hz)

Reference Example 21-24

$^1$H-NMR (CDCl$_3$) δ ppm: 2.50 (3H, s), 4.05 (3H, s), 5.99 (1H, brs), 6.80 (1H, d, J=2.0 Hz), 7.22 (1H, s), 7.52 (1H, s), 8.26 (1H, d, J=2.0 Hz)

Reference Example 21-25

$^1$H-NMR (CDCl$_3$) δ ppm: 1.85 (3H, s), 3.28 (1H, d, J=14.2 Hz), 3.43 (1H, d, J=14.2 Hz), 3.95 (3H, s), 6.07 (1H, s), 7.10 (1H, s), 7.13-7.21 (3H, m), 7.26-7.29 (2H, m), 7.32 (1H, s)

Reference Example 21-26

$^1$H-NMR (CDCl$_3$) δ ppm: 2.61 (3H, s), 3.02-3.08 (4H, m), 3.98 (3H, s), 5.88 (1H, s), 7.03 (1H, s), 7.16-7.20 (3H, m), 7.25-7.29 (2H, m), 7.33 (1H, s)

Reference Example 21-27

$^1$H-NMR (CDCl$_3$) δ ppm: 1.25 (9H, s), 2.60 (3H, s), 3.98 (3H, s), 5.93 (1H, s), 6.82 (1H, s), 7.53 (1H, s)

Reference Example 21-28

$^1$H-NMR (CDCl$_3$) δ ppm: 2.62 (3H, s), 4.03 (3H, s), 5.99 (1H, s), 7.15-7.20 (1H, m), 7.47 (1H, s)

Reference Example 21-29

$^1$H-NMR (CDCl$_3$) δ ppm: 1.70 (6H, br s), 2.08 (9H, br s), 2.62 (3H, s), 3.95 (3H, s), 5.53 (1H, br s), 7.10 (1H, br s), 7.29 (1H, br s)

Reference Example 21-30

$^1$H-NMR (CDCl$_3$) δ ppm: 2.50 (3H, s), 4.00 (3H, s), 4.96 (2H, s), 5.92 (1H, s), 6.83-6.96 (3H, m), 7.12 (1H, s), 7.21-7.26 (2H, m), 7.41 (1H, s)

Reference Example 21-31

$^1$H-NMR (CDCl$_3$) δ ppm: 2.46 (3H, s), 3.98 (3H, s), 5.33 (2H, s), 5.91 (1H, s), 6.95-7.10 (3H, m), 7.19 (1H, s), 7.27 (1H, s), 7.25-7.40 (2H, m)

Reference Example 21-32

$^1$H-NMR (CDCl$_3$) δ ppm: 1.40-1.50 (6H, m), 2.46 (3H, s), 3.20-3.40 (1H, m), 3.98 (3H, s), 5.93 (1H, s), 7.15 (1H, s), 7.28 (1H, s)

Reference Example 21-33

$^1$H-NMR (CDCl$_3$) δ ppm: 1.00-1.10 (3H, m), 1.80-2.00 (2H, m), 2.46 (3H, s), 2.80-3.00 (2H, m), 3.98 (3H, s), 5.92 (1H, s), 7.16 (1H, s), 7.27 (1H, s)

Reference Example 21-34

$^1$H-NMR (CDCl$_3$) δ ppm: 1.27 (3H, t, J=7.2 Hz), 2.45 (3H, s), 2.90 (2H, t, J=7.4 Hz), 3.24 (2H, t, J=7.4 Hz), 3.98 (3H, s), 4.18 (2H, q, J=7.2 Hz), 5.89 (1H, s), 7.14 (1H, s), 7.27 (1H, s)

Reference Example 21-35

$^1$H-NMR (CDCl$_3$) δ ppm: 2.54 (3H, s), 4.00 (3H, s), 5.97 (1H, s), 7.23 (1H, s), 7.29 (1H, s)

Reference Example 21-37

$^1$H-NMR (CDCl$_3$) δ ppm: 1.19 (3H, t, J=7.0 Hz), 2.45 (3H, s), 3.20 (2H, t. J=6.7 Hz), 3.54 (2H, q, J=7.0 Hz), 3.89 (2H, t, J=6.7 Hz), 3.98 (3H, s), 5.91 (1H, s), 7.16 (1H, s), 7.28 (1H, s)

Reference Example 21-38

$^1$H-NMR (CDCl$_3$) δ ppm: 2.66 (3H, s), 2.78 (6H, s), 3.95 (3H, s), 6.95 (1H, s), 7.50 (1H, s)

Reference Example 21-39

$^1$H-NMR (CDCl$_3$) δ ppm: 2.67 (3H, s), 3.42 (3H, s), 3.99 (3H, s), 7.18 (1H, s), 7.76 (1H, s)

Reference Example 21-40

$^1$H-NMR (CDCl$_3$) δ ppm: 1.17-1.41 (5H, m), 1.59-1.91 (5H, m), 2.59 (3H, s), 3.59-3.68 (1H, m), 4.02 (3H, s), 5.94 (1H, br), 6.97 (1H, d, J=8.3 Hz), 7.16 (1H, s), 7.48 (1H, s)

Reference Example 21-41

MS (ESI, m/z): 372 (M−1)

Reference Example 21-42

$^1$H-NMR (CDCl$_3$) δ ppm: 2.45 (3H, s), 4.01 (3H, s), 5.09 (2H, s), 6.13 (1H, s), 6.92 (2H, d, J=8.9 Hz), 7.02 (1H, s), 7.30-7.43 (5H, m), 7.47 (1H, s), 7.74 (2H, d, J=8.9 Hz)

Reference Example 21-43

$^1$H-NMR (CDCl$_3$) δ ppm: 0.31-0.39 (2H, m), 0.61-0.69 (2H, m), 1.21-1.31 (1H, m), 2.46 (3H, s), 3.83 (2H, d, J=6.9 Hz), 4.01 (3H, s), 6.11 (1H, s), 6.84 (2H, d, J=8.8 Hz), 7.02 (1H, s), 7.48 (1H, s), 7.73 (2H, d, J=8.9 Hz)

Reference Example 21-44

$^1$H-NMR (CDCl$_3$) δ ppm: 2.42 (3H, s), 3.93 (3H, s), 4.04 (3H, s), 7.07 (1H, s), 7.49 (1H, s), 7.80 (2H, d, J=8.5 Hz), 8.02 (2H, d, J=8.5 Hz)

Reference Example 21-45

$^1$H-NMR (CDCl$_3$) δ ppm: 2.45 (3H, s), 3.93 (3H, s), 6.95 (1H, s), 7.45 (1H, s), 7.73 (2H, d, J=8.4 Hz), 7.91 (2H, d, J=8.4 Hz)

Reference Example 22-1

[3-Hydroxy-4-methoxy-6-(5-methyl-[1,2,4]oxadiazol-3-yl)-2-nitrophenyl]phenylmethanone To a mixture of [5-hydroxy-4-methoxy-2-(5-methyl-[1,2,4]oxadiazol-3-yl)phenyl]phenylmethanone (reference example 21-1) (383 mg) and methylene chloride (10 mL) was added fuming nitric acid (68 μL) at room temperature, and the mixture was stirred for 20 minutes. The separated organic layer was washed with water, a saturated aqueous solution of sodium chloride, and dried over anhydrous sodium sulfate. The residue was triturated with hexane:methylene chloride=4:1 to give the title compound (377 mg).

$^1$H-NMR (CDCl$_3$) δ ppm: 2.46 (3H, s), 4.09 (3H, s), 7.30-7.90 (6H, m), 10.72 (1H, s)

Reference examples 22-2 to 22-45 were prepared in a manner similar to those as described in Reference example 22-1 using the corresponding phenols instead of [5-hydroxy-4-methoxy-2-(5-methyl-[1,2,4]oxadiazol-3-yl)phenyl]phenylmethanone. These were illustrated in table 11.

TABLE 11

| Reference example | Structure |
|---|---|
| 22-1 | |
| 22-2 | 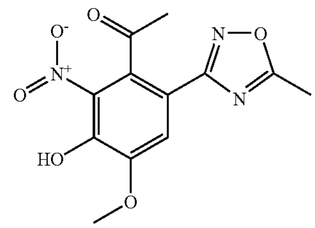 |
| 22-3 | 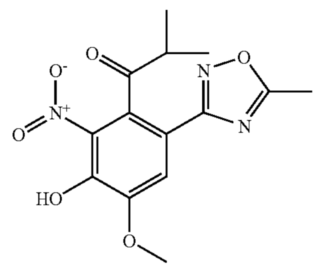 |
| 22-4 | 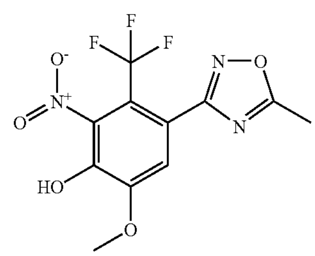 |
| 22-5 | 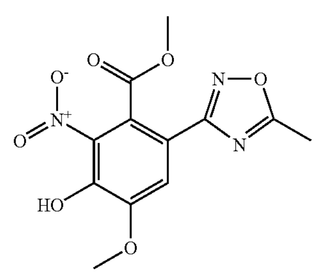 |
| 22-6 | 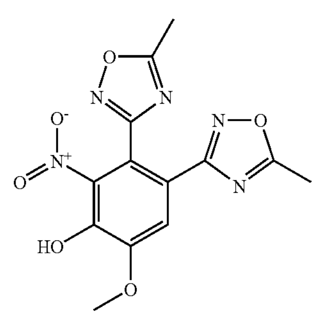 |

TABLE 11-continued

| Reference example | Structure |
|---|---|
| 22-7 | (methyl 2-(5-cyclopropyl-1,2,4-oxadiazol-3-yl)-4-hydroxy-5-methoxy-3-nitrobenzoate) |
| 22-8 | (2-(5-methyl-1,2,4-oxadiazol-3-yl)-4-hydroxy-5-methoxy-3-nitrobenzonitrile) |
| 22-9 | (methyl 2-(5-(methoxymethyl)-1,2,4-oxadiazol-3-yl)-4-hydroxy-5-methoxy-3-nitrobenzoate) |
| 22-10 | (methyl 2-(5-tert-butyl-1,2,4-oxadiazol-3-yl)-4-hydroxy-5-methoxy-3-nitrobenzoate) |
| 22-11 | (isopropyl 2-(5-methyl-1,2,4-oxadiazol-3-yl)-4-hydroxy-5-methoxy-3-nitrobenzoate) |
| 22-12 | (cyclohexyl 2-(5-methyl-1,2,4-oxadiazol-3-yl)-4-hydroxy-5-methoxy-3-nitrobenzoate) |
| 22-13 | (2-methoxyethyl 2-(5-methyl-1,2,4-oxadiazol-3-yl)-4-hydroxy-5-methoxy-3-nitrobenzoate) |
| 22-14 | (ethyl 2-(5-methyl-1,2,4-oxadiazol-3-yl)-4-hydroxy-5-methoxy-3-nitrobenzoate) |
| 22-15 | (N-tert-butyl-2-(2-(5-methyl-1,2,4-oxadiazol-3-yl)-4-hydroxy-5-methoxy-3-nitrophenyl)-2-oxoacetamide) |
| 22-16 | (2-(5-methyl-1,2,4-oxadiazol-3-yl)-4-hydroxy-5-methoxy-3-nitrobenzoic acid) |

TABLE 11-continued

| Reference example | Structure |
|---|---|
| 22-17 | (structure) |
| 22-18 | (structure) |
| 22-19 | (structure) |
| 22-20 | (structure) |
| 22-21 | (structure) |
| 22-22 | (structure) |
| 22-23 | (structure) |
| 22-24 | (structure) |
| 22-25 | (structure) |

TABLE 11-continued

| Reference example | Structure |
|---|---|
| 22-26 | (structure) |
| 22-27 | (structure) |
| 22-28 | (structure) |
| 22-29 | (structure) |
| 22-30 | (structure) |
| 22-31 | (structure) |
| 22-32 | (structure) |
| 22-33 | (structure) |
| 22-34 | (structure) |
| 22-35 | (structure) |

TABLE 11-continued

| Reference example | Structure |
|---|---|
| 22-36 | 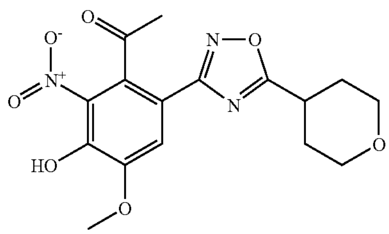 |
| 22-37 | 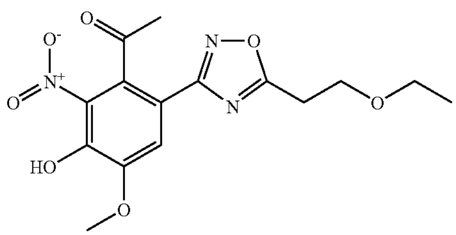 |
| 22-38 | 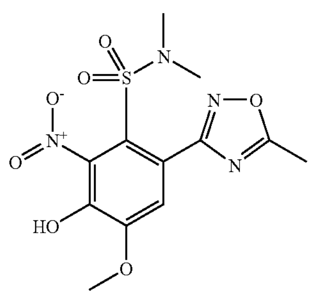 |
| 22-39 | 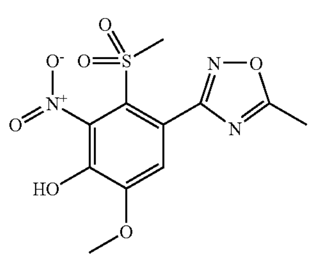 |
| 22-40 | 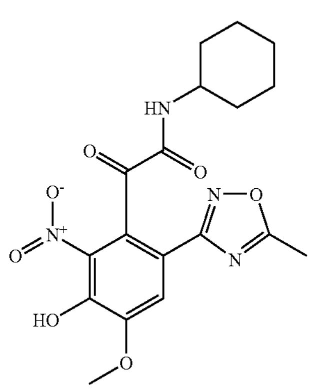 |
| 22-41 | |
| 22-42 | |
| 22-43 | |
| 22-44 | |

TABLE 11-continued

| Reference example | Structure |
|---|---|
| 22-45 | (structure: benzoyl group with 4-cyanophenyl, nitro, hydroxy, methoxy, and 5-methyl-1,3,4-oxadiazole substituents) |

The physical data of reference examples 22-2 to 22-20, 22-22 to 22-32, 22-34, 22-35 and 22-37 to 22-45 were shown below.

Reference Example 22-2

$^1$H-NMR (CDCl$_3$) δ ppm: 2.64 (3H, s), 2.68 (3H, s), 4.04 (3H, s), 7.75 (1H, s)

Reference Example 22-3

$^1$H-NMR (DMSO-d$_6$) δ ppm: 1.01 (6H, d, J=6.8 Hz), 2.57-2.64 (1H, m), 2.67 (3H, s), 4.00 (3H, s), 7.54 (1H, s), 11.47 (1H, br s)

Reference Example 22-4

$^1$H-NMR (DMSO-d$_6$) δ ppm: 2.70 (3H, s), 3.99 (3H, s), 7.43 (1H, s), 11.82 (1H, br)

Reference Example 22-5

MS (ESI, m/z): 308 (M−1)

Reference Example 22-6

$^1$H-NMR (DMSO-d$_6$) δ ppm: 2.59 (3H, s), 2.62 (3H, s), 4.03 (3H, s), 7.62 (1H, s)

Reference Example 22-7

$^1$H-NMR (CDCl$_3$) δ ppm: 1.12-1.15 (2H, m), 1.28-1.32 (2H, m), 2.38-2.43 (1H, m), 3.68 (3H, s), 3.99 (3H, s), 7.50 (1H, s), 11.54 (1H, br)

Reference Example 22-8

$^1$H-NMR (CDCl$_3$) δ ppm: 2.72 (3H, s), 4.10 (3H, s), 7.67 (1H, s), 9.99 (1H, br s)

Reference Example 22-9

$^1$H-NMR (DMSO-d$_6$) δ ppm: 3.42 (3H, s), 3.69 (3H, s), 4.01 (3H, s), 4.83 (2H, s), 7.55 (1H, s), 11.66 (1H, br)

Reference Example 22-10

$^1$H-NMR (DMSO-d$_6$) δ ppm: 1.42 (9H, s), 3.68 (3H, s), 4.00 (3H, s), 7.51 (1H, s), 11.58 (1H, br)

Reference Example 22-11

$^1$H-NMR (CDCl$_3$) δ ppm: 1.30-1.40 (6H, m), 2.64 (3H, s), 4.04 (3H, s), 5.30-5.40 (1H, m), 7.71 (1H, s), 10.54 (1H, s)

Reference Example 22-12

$^1$H-NMR (CDCl$_3$) δ ppm: 1.00-2.10 (10H, m), 2.63 (3H, s), 4.03 (3H, s), 5.10-5.20 (1H, m), 7.71 (1H, s), 10.51 (1H, br s)

Reference Example 22-13

$^1$H-NMR (CDCl$_3$) δ ppm: 2.64 (3H, s), 3.38 (3H, s), 3.70-3.80 (2H, m), 4.04 (3H, s), 4.50-4.60 (2H, s), 7.74 (1H, s), 10.65 (1H, br s)

Reference Example 22-14

$^1$H-NMR (CDCl$_3$) δ ppm: 1.30-1.40 (3H, m), 2.64 (3H, s), 4.04 (3H, s), 4.40-4.50 (2H, m), 7.73 (1H, s), 10.58 (1H, s)

Reference Example 22-15

$^1$H-NMR (DMSO-d$_6$) δ ppm: 1.25 (9H, s), 2.62 (3H, s), 4.02 (3H, s), 7.59 (1H, s), 8.00 (1H, br), 11.53 (1H, br)

Reference Example 22-16

$^1$H-NMR (DMSO-d$_6$) δ ppm: 2.66 (3H, s), 3.97 (3H, s), 7.43 (1H, s)

Reference Example 22-18

MS (ESI, m/z): 369 (M−1)

Reference Example 22-19

$^1$H-NMR (DMSO-d$_6$) δ ppm: 2.45 (3H, s), 4.03 (3H, s), 7.50-7.70 (2H, m), 7.95-8.15 (2H, m), 8.40-8.50 (1H, m), 11.00-11.70 (1H, br)

Reference Example 22-20

MS (ESI, m/z): 362 (M+1)

Reference Example 22-22

$^1$H-NMR (DMSO-d$_6$) δ ppm: 2.48 (3H, s), 4.03 (3H, s), 7.20-7.28 (2H, m), 7.60 (1H, s), 7.61-7.65 (2H, m), 11.59 (1H, br s)

Reference Example 22-23

$^1$H-NMR (DMSO-d$_6$) δ ppm: 2.49 (3H, s), 4.05 (3H, s), 7.65 (1H, s), 7.94 (1H, d, J=3.0 Hz), 8.22 (1H, d, J=3.0 Hz), 11.00-12.00 (1H, br)

Reference Example 22-24

$^1$H-NMR (DMSO-d$_6$) δ ppm: 2.53 (3H, s), 4.05 (3H, s), 7.16 (1H, d, J=2.2 Hz), 7.68 (1H, s), 8.76 (1H, d, J=2.2 Hz)

Reference Example 22-25

$^1$H-NMR (DMSO-d$_6$) δ ppm: 1.77 (3H, s), 3.97 (3H, s), 7.16-7.24 (5H, m), 7.57 (1H, s), 11.67 (1H, br)

Reference Example 22-26

¹H-NMR (DMSO-d₆) δ ppm: 2.66 (3H, s), 2.88-2.95 (4H, m), 3.97 (3H, s), 7.15-7.28 (5H, m), 7.61 (1H, s), 11.56 (1H, br)

Reference Example 22-27

¹H-NMR (DMSO-d₆) δ ppm: 1.00 (9H, s), 2.67 (3H, s), 3.99 (3H, s), 7.54 (1H, s), 11.49 (1H, brs)

Reference Example 22-28

¹H-NMR (DMSO-d₆) δ ppm: 2.68 (3H, s), 4.06 (3H, s), 7.68 (1H, s)

Reference Example 22-29

¹H-NMR (CDCl₃) δ ppm: 1.70 (6H, br s), 2.05-2.20 (9H, m), 2.65 (3H, s), 4.01 (3H, s), 5.39 (1H, br s), 7.53 (1H, s), 9.86 (1H, br s)

Reference Example 22-30

¹H-NMR (CDCl₃) δ ppm: 2.58 (3H, s), 4.06 (3H, s), 5.10 (2H, s), 6.78-6.81 (2H, m), 6.93-6.97 (1H, m), 7.21-7.25 (2H, m), 7.76 (1H, s), 10.85 (1H, s)

Reference Example 22-31

¹H-NMR (DMSO-d₆) δ ppm: 2.30 (3H, s), 4.00 (3H, s), 5.60 (2H, s), 6.95-7.15 (3H, m), 7.25-7.40 (2H, m), 7.60 (1H, s)

Reference Example 22-32

¹H-NMR (CDCl₃) δ ppm: 1.40-1.50 (6H, m), 2.70 (3H, s), 3.20-3.30 (1H, m), 4.05 (3H, s), 7.77 (1H, s), 10.73 (1H, br s)

Reference Example 22-34

¹H-NMR (DMSO-d₆) δ ppm: 1.18 (3H, t, J=7.1 Hz), 2.32 (3H, s), 2.88 (2H, t, J=6.8 Hz), 3.24 (2H, t, J=6.8 Hz), 3.99 (3H, s), 4.08 (2H, q, J=7.1 Hz), 7.56 (1H, s), 11.00-12.00 (1H, br)

Reference Example 22-35

¹H-NMR (DMSO-d₆) δ ppm: 2.43 (3H, s), 4.01 (3H, s), 7.62 (1H, s), 11.05-12.50 (1H, br)

Reference Example 22-37

¹H-NMR (DMSO-d₆) δ ppm: 1.07 (3H, t, J=7.0 Hz), 2.34 (3H, s), 3.25 (2H, t, J=6.1 Hz), 3.46 (2H, q, J=7.0 Hz), 3.80 (2H, t, J=6.1 Hz), 3.99 (3H, s), 7.57 (1H, s), 11.40-11.70 (1H, br)

Reference Example 22-38

¹H-NMR (CDCl₃) δ ppm: 2.69 (3H, s), 2.81 (6H, s), 3.99 (3H, s), 6.96 (1H, s)

Reference Example 22-39

¹H-NMR (CDCl₃) δ ppm: 2.69 (3H, s), 3.55 (3H, s), 4.04 (3H, s), 7.15 (1H, s)

Reference Example 22-40

¹H-NMR (DMSO-d₆) δ ppm: 1.03-1.73 (10H, m), 2.61 (3H, s), 3.39-3.50 (1H, m), 4.03 (3H, s), 7.59 (1H, s), 8.66 (1H, d, J=8.6 Hz), 11.56 (1H, br)

Reference Example 22-41

¹H-NMR (CDCl₃) δ ppm: 1.07-2.01 (10H, m), 2.59-2.60 (3H, m), 2.94-3.36 (3H, m), 4.03-4.04 (3H, m), 4.25-4.80 (1H, m), 7.75-7.80 (1H, m), 10.87 (1H, br)

Reference Example 22-42

¹H-NMR (CDCl₃) δ ppm: 2.48 (3H, s), 4.08 (3H, s), 5.09 (2H, s), 6.95 (2H, d, J=9.0 Hz), 7.31-7.44 (5H, m), 7.63-7.80 (3H, m)

Reference Example 22-43

¹H-NMR (CDCl₃) δ ppm: 0.32-0.39 (2H, m), 0.63-0.71 (2H, m), 1.22-1.32 (1H, m), 2.48 (3H, s), 3.84 (2H, d, J=6.9 Hz), 4.08 (3H, s), 6.86 (2H, d, J=9.1 Hz), 7.60-7.79 (3H, m)

Reference Example 22-44

¹H-NMR (CDCl₃) δ ppm: 2.45 (3H, s), 3.93 (3H, s), 4.10 (3H, s), 7.82-7.88 (3H, m), 8.07 (2H, d, J=8.8 Hz)

Reference Example 22-45

¹H-NMR (CDCl₃) δ ppm: 2.47 (3H, s), 4.09 (3H, s), 7.69-7.95 (5H, m)

Reference Example 23-1

[3-Hydroxy-4-methoxy-6-(5-methyl-[1,2,4]oxadiazol-3-yl)-2-nitrophenyl]-(4-hydroxyphenyl)methanone A mixture of (4-benzyloxyphenyl)-[3-hydroxy-4-methoxy-6-(5-methyl-[1,2,4]oxadiazol-3-yl)-2-nitrophenyl]methanone (reference example 22-42) (395 mg) and a 25% hydrogen bromide-acetic acid solution (10 mL) was stirred at 45° C. for 2 hours. The mixture was concentrated under reduced pressure to give the title compound (310 mg).

¹H-NMR (CDCl₃) δ ppm: 2.48 (3H, s), 4.06 (3H, s), 6.81 (2H, d, J=8.8 Hz), 7.53-7.68 (2H, m), 7.71 (1H, s)

Example 1-1

[3,4-Dihydroxy-6-(5-methyl-[1,2,4]oxadiazol-3-yl)-2-nitro-phenyl]phenylmethanone (compound 1-1)

To a mixture of [3-hydroxy-4-methoxy-6-(5-methyl-[1,2,4]oxadiazol-3-yl)-2-nitrophenyl]phenylmethanone (reference example 22-1) (377 mg) and ethyl acetate (10.6 mL) were added aluminum chloride (361 mg) and pyridine (0.387 mL). The mixture was refluxed for 2.5 hours. After cooling to room temperature, 1 mol/L hydrochloric acid was added to the mixture. The separated organic layer was washed with brine, dried over anhydrous magnesium sulfate, and concentrated under reduced pressure. The residue was triturated with hexane:methylene chloride=4:1 to give the title compound (317 mg) as an amorphous.

¹H-NMR (DMSO-d₆) δ ppm: 2.43 (3H, s), 7.40-7.70 (6H, m), 11.28 (2H, brs)

MS (ESI, m/z): 342 (M+1)

Compounds 1-2 to 1-45 were prepared in a manner similar to those as described in Example 1-1 using the corresponding 3-nitrobenzene-1-methoxy-2-ols instead of [3-hydroxy-4-methoxy-6-(5-methyl-[1,2,4]oxadiazol-3-yl)-2-nitrophenyl]phenylmethanone. These were illustrated in table 12.

TABLE 12

| Compound No. | Structure |
|---|---|
| 1-1 | 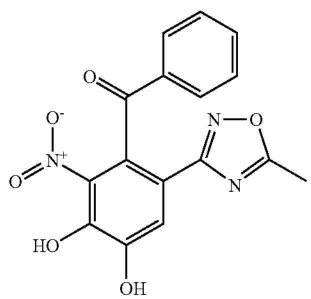 |
| 1-2 | 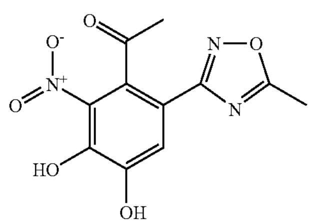 |
| 1-3 | 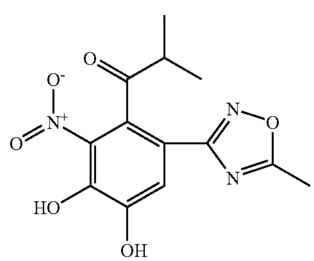 |
| 1-4 | 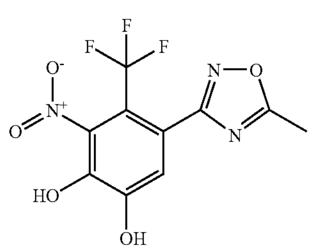 |
| 1-5 | 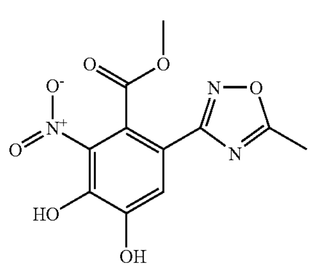 |

TABLE 12-continued

| Compound No. | Structure |
|---|---|
| 1-6 | 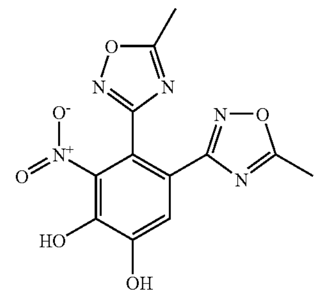 |
| 1-7 | 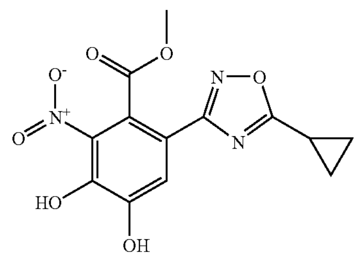 |
| 1-8 | 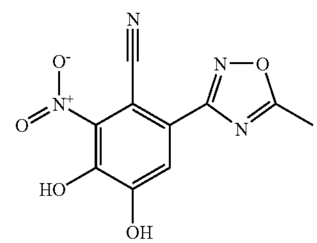 |
| 1-9 | 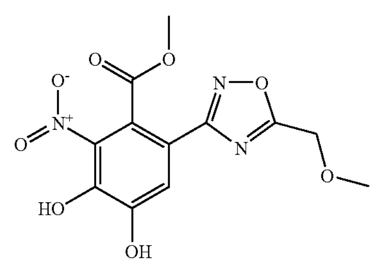 |
| 1-10 | 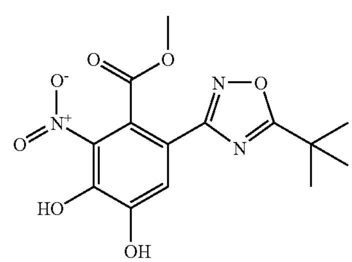 |
| 1-11 | 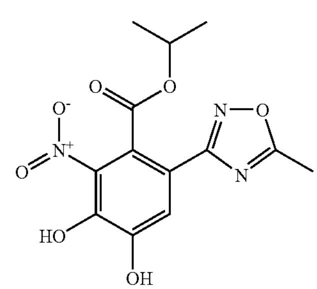 |

TABLE 12-continued

| Compound No. | Structure |
|---|---|
| 1-12 | cyclohexyl ester of 2-(5-methyl-1,2,4-oxadiazol-3-yl)-6-nitro-3,4-dihydroxybenzoate |
| 1-13 | 2-methoxyethyl ester of 2-(5-methyl-1,2,4-oxadiazol-3-yl)-6-nitro-3,4-dihydroxybenzoate |
| 1-14 | ethyl ester of 2-(5-methyl-1,2,4-oxadiazol-3-yl)-6-nitro-3,4-dihydroxybenzoate |
| 1-15 | N-tert-butyl 2-oxo-2-[2-(5-methyl-1,2,4-oxadiazol-3-yl)-6-nitro-3,4-dihydroxyphenyl]acetamide |
| 1-16 | 2-(5-methyl-1,2,4-oxadiazol-3-yl)-6-nitro-3,4-dihydroxybenzoic acid |
| 1-17 | (4-methylphenyl)(2-(5-methyl-1,2,4-oxadiazol-3-yl)-6-nitro-3,4-dihydroxyphenyl)methanone |
| 1-18 | N-phenyl 2-(5-methyl-1,2,4-oxadiazol-3-yl)-6-nitro-3,4-dihydroxybenzamide |
| 1-19 | pyridin-2-yl (2-(5-methyl-1,2,4-oxadiazol-3-yl)-6-nitro-3,4-dihydroxyphenyl)methanone |
| 1-20 | cyclohexyl (2-(5-methyl-1,2,4-oxadiazol-3-yl)-6-nitro-3,4-dihydroxyphenyl)methanone |
| 1-21 | cyclopropyl (2-(5-methyl-1,2,4-oxadiazol-3-yl)-6-nitro-3,4-dihydroxyphenyl)methanone |

TABLE 12-continued

| Compound No. | Structure |
|---|---|
| 1-22 | (2-fluorophenyl)(3-(5-methyl-1,2,4-oxadiazol-3-yl)-5,6-dihydroxy-2-nitrophenyl)methanone |
| 1-23 | (thiazol-2-yl)(3-(5-methyl-1,2,4-oxadiazol-3-yl)-5,6-dihydroxy-2-nitrophenyl)methanone |
| 1-24 | (isoxazol-5-yl)(3-(5-methyl-1,2,4-oxadiazol-3-yl)-5,6-dihydroxy-2-nitrophenyl)methanone |
| 1-25 | 1-(3-(5-methyl-1,2,4-oxadiazol-3-yl)-5,6-dihydroxy-2-nitrophenyl)-2-phenylethan-1-one |
| 1-26 | 1-(3-(5-methyl-1,2,4-oxadiazol-3-yl)-5,6-dihydroxy-2-nitrophenyl)-3-phenylpropan-1-one |
| 1-27 | 2,2-dimethyl-1-(3-(5-methyl-1,2,4-oxadiazol-3-yl)-5,6-dihydroxy-2-nitrophenyl)propan-1-one |
| 1-28 | 2,2,2-trifluoro-1-(3-(5-methyl-1,2,4-oxadiazol-3-yl)-5,6-dihydroxy-2-nitrophenyl)ethan-1-one |
| 1-29 | N-(adamantan-1-yl)-3-(5-methyl-1,2,4-oxadiazol-3-yl)-5,6-dihydroxy-2-nitrobenzamide |
| 1-30 | 1-(3-(5-methyl-1,2,4-oxadiazol-3-yl)-5,6-dihydroxy-2-nitrophenyl)-2-phenoxyethan-1-one |
| 1-31 | 1-(3-(5-(phenoxymethyl)-1,2,4-oxadiazol-3-yl)-5,6-dihydroxy-2-nitrophenyl)ethan-1-one |

TABLE 12-continued

| Compound No. | Structure |
|---|---|
| 1-32 | 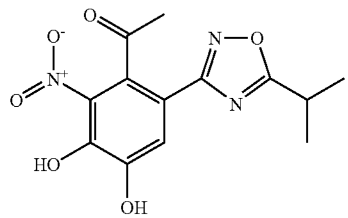 |
| 1-33 | 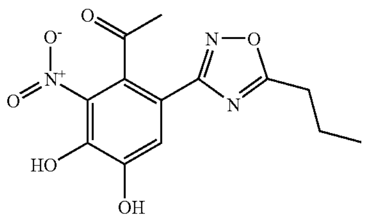 |
| 1-34 | 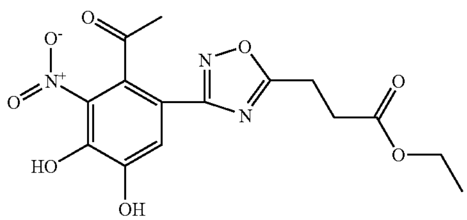 |
| 1-35 | 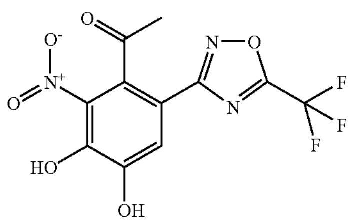 |
| 1-36 | 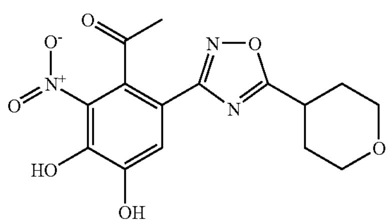 |
| 1-37 | 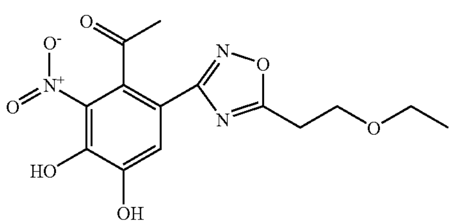 |
| 1-38 | 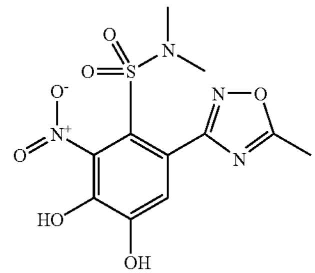 |
| 1-39 | 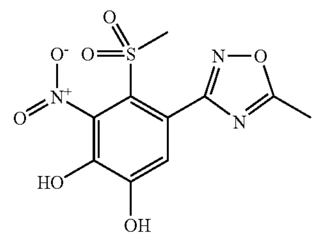 |
| 1-40 | 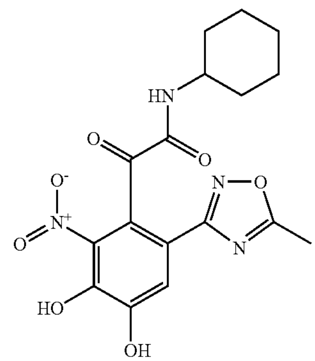 |
| 1-41 | 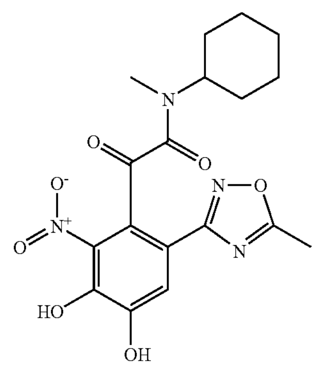 |
| 1-42 | 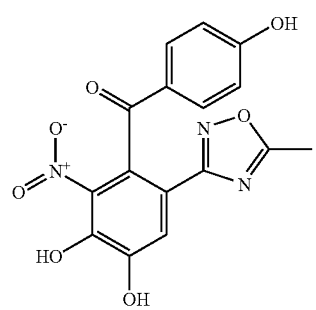 |

TABLE 12-continued

| Compound No. | Structure |
|---|---|
| 1-43 | (structure: 4-(cyclopropylmethoxy)phenyl ketone with nitro, dihydroxy phenyl bearing 5-methyl-1,2,4-oxadiazole) |
| 1-44 | (structure: methyl 4-benzoate with nitro, dihydroxy phenyl bearing 5-methyl-1,2,4-oxadiazole) |
| 1-45 | (structure: 4-cyanophenyl ketone with nitro, dihydroxy phenyl bearing 5-methyl-1,2,4-oxadiazole) |

The physical data of compounds 1-2 to 1-45 were shown below.

Compound 1-2

$^1$H-NMR (DMSO-$d_6$) δ ppm: 2.34 (3H, s), 2.65 (3H, s), 7.52 (1H, s), 11.17 (1H, br s)

Compound 1-3

$^1$H-NMR (DMSO-$d_6$) δ ppm: 1.00 (6H, d, J=6.8 Hz), 2.56-2.63 (1H, m), 2.64 (3H, s), 7.46 (1H, s), 11.18 (2H, br s)

Compound 1-4

$^1$H-NMR (DMSO-$d_6$) δ ppm: 2.68 (3H, s), 7.21 (1H, s), 11.57 (2H, br)

Compound 1-5

$^1$H-NMR (DMSO-$d_6$) δ ppm: 2.64 (3H, s), 3.67 (3H, s), 7.42 (1H, s), 11.29 (2H, br)

Compound 1-6

$^1$H-NMR (DMSO-$d_6$) δ ppm: 2.56 (3H, s), 2.61 (3H, s), 7.54 (1H, s), 11.38 (2H, br s)

Compound 1-7

$^1$H-NMR (DMSO-$d_6$) δ ppm: 1.10-1.14 (2H, m), 1.26-1.31 (2H, m), 2.35-2.42 (1H, m), 3.66 (3H, s), 7.40 (1H, s), 11.27 (2H, br)

Compound 1-8

$^1$H-NMR (DMSO-$d_6$) δ ppm: 2.70 (3H, s), 7.61 (1H, s)

Compound 1-9

$^1$H-NMR (DMSO-$d_6$) δ ppm: 3.41 (3H, s), 3.67 (3H, s), 4.81 (2H, s), 7.44 (1H, s), 11.38 (2H, br)

Compound 1-10

$^1$H-NMR (DMSO-$d_6$) δ ppm: 1.41 (9H, s), 3.67 (3H, s), 7.45 (1H, s), 11.33 (2H, br)

Compound 1-11

$^1$H-NMR (DMSO-$d_6$) δ ppm: 1.10-1.20 (6H, m), 2.63 (3H, s), 4.90-5.00 (1H, m), 7.63 (1H, s), 11.27 (2H, br s)

Compound 1-12

$^1$H-NMR (DMSO-$d_6$) δ ppm: 1.20-1.80 (10H, m), 2.62 (3H, s), 4.70-4.80 (1H, m), 7.36 (1H, s), 11.26 (2H, br s)

Compound 1-13

$^1$H-NMR (DMSO-$d_6$) δ ppm: 2.62 (3H, s), 3.18 (3H, s), 3.40-3.50 (2H, m), 4.10-4.20 (2H, m), 7.38 (1H, s), 11.16 (1H, br s)

Compound 1-14

$^1$H-NMR (DMSO-$d_6$) δ ppm: 1.00-1.20 (3H, m), 2.64 (3H, s), 4.10-4.20 (2H, m), 7.38 (1H, s), 11.25 (1H, br s)

Compound 1-15

$^1$H-NMR (DMSO-$d_6$) δ ppm: 1.24 (9H, s), 2.60 (3H, s), 7.50 (1H, s), 7.97 (1H, br), 11.32 (2H, br)

Compound 1-16

$^1$H-NMR (DMSO-$d_6$) δ ppm: 2.63 (3H, s), 7.31 (1H, s)

Compound 1-17

$^1$H-NMR (DMSO-$d_6$) δ ppm: 2.33 (3H, s), 2.45 (3H, s), 7.20-7.30 (2H, m), 7.50-7.60 (3H, m), 11.22 (1H, br s)

Compound 1-18

$^1$H-NMR (DMSO-$d_6$) δ ppm: 2.55 (3H, s), 7.05-7.10 (1H, m), 7.27-7.32 (2H, m), 7.46-7.49 (2H, m), 7.55 (1H, s), 10.41 (1H, s), 10.98 (1H, br), 11.08 (1H, br)

Compound 1-19

$^1$H-NMR (DMSO-d$_6$) δ ppm: 2.42 (3H, s), 7.50-7.65 (2H, m), 7.95-8.15 (2H, m), 8.40-8.50 (1H, m), 10.50-11.50 (2H, m)

Compound 1-20

$^1$H-NMR (DMSO-d$_6$) δ ppm: 1.02-1.78 (10H, m), 2.22-2.30 (1H, m), 2.65 (3H, s), 7.46 (1H, s), 11.11 (1H, br)

Compound 1-21

$^1$H-NMR (DMSO-d$_6$) δ ppm: 0.91-0.99 (4H, m), 1.91-1.98 (1H, m), 2.64 (3H, s), 7.43 (1H, s), 11.18 (2H, br)

Compound 1-22

$^1$H-NMR (DMSO-d$_6$) δ ppm: 2.45 (3H, s), 7.19-7.27 (2H, m), 7.51 (1H, s), 7.58-7.64 (2H, m), 11.27 (1H, br s)

Compound 1-23

$^1$H-NMR (DMSO-d$_6$) δ ppm: 2.46 (3H, s), 7.56 (1H, s), 7.93 (1H, d, J=3.0 Hz), 8.20 (1H, d, J=3.0 Hz), 10.50-12.00 (2H, br)

Compound 1-24

$^1$H-NMR (DMSO-d$_6$) δ ppm: 7.13 (1H, d, J=2.0 Hz), 7.62 (1H, s), 8.74 (1H, d, J=2.0 Hz)

Compound 1-25

$^1$H-NMR (DMSO-d$_6$) δ ppm: 1.75 (3H, s), 3.25-3.33 (2H, m), 7.13 (1H, s), 7.14-7.23 (5H, m), 11.52 (1H, br)

Compound 1-26

$^1$H-NMR (DMSO-d$_6$) δ ppm: 2.64 (3H, s), 2.87-2.93 (4H, m), 7.14-7.28 (5H, m), 7.55 (1H, s), 11.17 (2H, br)

Compound 1-27

$^1$H-NMR (DMSO-d$_6$) δ ppm: 1.00 (9H, s), 2.65 (3H, s), 7.47 (1H, s), 11.11 (2H, br s)

Compound 1-28

$^1$H-NMR (DMSO-d$_6$) δ ppm: 2.66 (3H, s), 7.59 (1H, s)

Compound 1-29

$^1$H-NMR (DMSO-d$_6$) δ ppm: 1.60 (6H, br s), 1.89 (6H, br s), 1.99 (3H, br s), 2.62 (3H, s), 7.40 (1H, s), 7.81 (1H, s), 10.69 (1H, br s), 10.81 (1H, br s)

Compound 1-30

$^1$H-NMR (DMSO-d$_6$) δ ppm: 2.56 (3H, s), 4.94 (2H, s), 6.84-6.96 (3H, m), 7.23-7.27 (2H, m), 7.58 (1H, s), 11.30 (2H, br)

Compound 1-31

$^1$H-NMR (DMSO-d$_6$) δ ppm: 2.29 (3H, s), 5.59 (2H, s), 6.95-7.15 (3H, m), 7.30-7.40 (2H, m), 7.54 (1H, s), 10.00-12.00 (2H, br)

Compound 1-32

$^1$H-NMR (DMSO-d$_6$) δ ppm: 1.30-1.40 (6H, m), 2.35 (3H, s), 7.56 (1H, s), 11.17 (2H, br s)

Compound 1-33

$^1$H-NMR (DMSO-d$_6$) δ ppm: 0.90-1.00 (3H, m), 1.70-1.90 (2H, m), 2.34 (3H, s), 2.90-3.00 (2H, m), 7.54 (1H, s), 11.18 (2H, br s)

Compound 1-34

$^1$H-NMR (DMSO-d$_6$) δ ppm: 1.10-1.25 (3H, m), 2.31 (3H, s), 2.86 (2H, t, J=6.8 Hz), 3.22 (2H, t, J=6.8 Hz), 4.00-4.15 (2H, m), 7.50 (1H, s), 10.50-11.50 (2H, br)

Compound 1-35

$^1$H-NMR (DMSO-d$_6$) δ ppm: 2.41 (3H, s), 7.57 (1H, s), 10.50-12.00 (2H, br)

Compound 1-36

MS (ESI, m/z): 348 (M−1)

Compound 1-37

$^1$H-NMR (DMSO-d$_6$) δ ppm: 1.07 (3H, t, J=7.0 Hz), 2.33 (3H, s), 3.23 (2H, t, J=6.2 Hz), 3.45 (2H, q, J=7.0 Hz), 3.79 (2H, t, J=6.2 Hz), 7.52 (1H, s), 10.80-11.80 (2H, br)

Compound 1-38

$^1$H-NMR (DMSO-d$_6$) δ ppm: 2.63 (6H, s), 6.95 (1H, s)

Compound 1-39

$^1$H-NMR (DMSO-d$_6$) δ ppm: 2.68 (3H, s), 3.46 (3H, s), 7.11 (1H, s)

Compound 1-40

$^1$H-NMR (DMSO-d$_6$) δ ppm: 1.02-1.72 (10H, m), 2.59 (3H, s), 3.37-3.48 (1H, m), 7.51 (1H, s), 8.61 (1H, d, J=8.5 Hz), 11.32 (2H, br)

Compound 1-41

$^1$H-NMR (DMSO-d$_6$) δ ppm: 1.03-1.89 (10H, m), 2.60-2.65 (3H, m), 2.60-3.05 (3H, m), 3.83-3.94 (1H, m), 7.40-7.45 (1H, m), 11.30 (2H, br)

Compound 1-42

$^1$H-NMR (DMSO-d$_6$) δ ppm: 2.47 (3H, s), 6.74 (2H, d, J=9.1 Hz), 7.48 (2H, d, J=8.2 Hz), 7.54 (1H, s)

Compound 1-43

$^1$H-NMR (DMSO-d$_6$) δ ppm: 0.29-0.38 (2H, m), 0.53-0.63 (2H, m), 1.19-1.29 (1H, m), 2.47 (3H, s), 3.86-3.92 (2H, m), 6.90-6.97 (3H, m), 7.51 (2H, d, J=8.8 Hz)

Compound 1-44

$^1$H-NMR (DMSO-d$_6$) δ ppm: 2.43 (3H, s), 3.86 (3H, s), 7.60 (1H, s), 7.76 (2H, d, J=8.7 Hz), 7.99 (2H, d, J=8.7 Hz)

Compound 1-45

¹H-NMR (DMSO-d₆) δ ppm: 2.44 (3H, s), 7.60 (1H, s), 7.81 (2H, d, J=8.6 Hz), 7.92 (2H, d, J=8.6 Hz)

Example 2-1

2,2-Dimethylpropionic acid=6-(2,2-dimethylpropionyloxy)-3-isobutyryl-4-(5-methyl-[1,2,4]oxadiazol-3-yl)-2-nitrophenyl ester (compound 2-1)

To a mixture of 1-[3,4-dihydroxy-6-(5-methyl-[1,2,4]-oxadiazol-3-yl)-2-nitrophenyl]-2-methylpropane-1-one (compound 1-3) (100 mg) and tetrahydrofuran (2 mL) were added trimethylacetyl chloride (94 μL) and triethylamine (100 μL) under ice bath cooling while stirring. The mixture was stirred for 30 minutes, warmed to room temperature, and stirred overnight. The mixture was diluted with ethyl acetate, washed with 1 mol/L hydrochloric acid and brine, dried over anhydrous magnesium sulfate, and concentrated under reduced pressure. The residue was purified by silica gel column chromatography (eluent: 0%-20% ethyl acetate/hexane, gradient elution) to give the title compound (174 mg). The structural formula was illustrated in table 13.

¹H-NMR (CDCl₃) δ ppm: 1.20 (6H, d, J=6.9 Hz), 1.34 (9H, s), 1.36 (9H, s), 2.65 (3H, s), 2.82 (1H, septet, J=6.9 Hz), 8.04 (1H, s)

Example 3-1

Methyl 4-ethoxycarbonyloxy-3-hydroxy-6-(5-methyl-[1,2,4]-oxadiazol-3-yl)-2-nitrobenzoate (compound 3-1)

A mixture of methyl 3,4-dihydroxy-6-(5-methyl-[1,2,4]-oxadiazol-3-yl)-2-nitrobenzoate (compound 1-5) (50 mg), ethyl chlorocarbonate (0.02 mL), potassium carbonate (28 mg) and N,N-dimethylformamide (2 mL) was stirred at 50° C. for 3 hours. After cooling to room temperature, water and ethyl acetate were added to the mixture. The separated organic layer was washed with water and brine successively, dried over anhydrous magnesium sulfate, and concentrated under reduced pressure. The residue was purified by silica gel column chromatography (eluent: 20%-100% ethyl acetate/hexane, gradient elution) to give the title compound (51 mg). The structural formula was illustrated in table 13.

¹H-NMR (CDCl₃) δ ppm: 1.42 (3H, t, J=7.2 Hz), 2.64 (3H, s), 4.01 (3H, s), 4.38 (2H, q, J=7.2 Hz), 8.23 (1H, s), 10.98 (1H, br)

Example 4-1

Methyl 4-diethylcarbamoyloxy-3-hydroxy-6-(5-methyl-[1,2,4]-oxadiazol-3-yl)-2-nitrobenzoate (compound 4-1)

A mixture of methyl 3,4-dihydroxy-6-(5-methyl-[1,2,4]-oxadiazol-3-yl)-2-nitrobenzoate (compound 1-5) (50 mg), diethylcarbamoyl chloride (0.024 mL), 4-dimethylaminopyridine (4 mg) and pyridine (2 mL) was stirred at room temperature for 3 hours. After addition of ethyl acetate, the mixture was acidified with 2 mol/L hydrochloric acid. The separated organic layer was washed with water, dried over anhydrous magnesium sulfate, and concentrated under reduced pressure. The residue was purified by silica gel column chromatography (eluent: 20%-100% ethyl acetate/hexane, gradient elution) to give the title compound (31 mg). The structural formula was illustrated in table 13.

¹H-NMR (CDCl₃) δ ppm: 1.14-1.27 (6H, m), 2.61-2.67 (3H, m), 3.32-3.46 (4H, m), 3.88-4.02 (3H, m), 8.13-8.19 (1H, m)

TABLE 13

| Compound No. | Structure |
|---|---|
| 2-1 | (structure) |
| 3-2 | (structure) |
| 4-1 | (structure) |

Example 5-1

[3,4-Dihydroxy-6-(5-methyl-[1,2,4]oxadiazol-3-yl)-2-nitro-phenyl]phenylmethanone mono potassium salt (compound 5-1)

To a mixture of [3,4-dihydroxy-6-(5-methyl-[1,2,4]-oxadiazol-3-yl)-2-nitrophenyl]phenylmethanone (compound 1-1) (100 mg), water (2.5 mL) and tert-butanol (2.5 mL) was added a 1 mol/L aqueous solution of potassium hydroxide (0.292 mL). The mixture was concentrated under reduced pressure to give the title compound (103 mg) as an amorphous.

¹H-NMR (DMSO-d₆) δ ppm: 2.38 (3H, s), 6.94 (1H, s), 7.35-7.41 (2H, m), 7.45-7.51 (1H, m), 7.63-7.68 (2H, m)

Compounds 5-2 to 5-6 were prepared in a manner similar to those as described in Example 5-1 using the corresponding 3-nitrobenzene-1,2-diols and sodium hydroxide or potassium hydroxide instead of [3,4-dihydroxy-6-(5-methyl-[1,2,4]-oxadiazol-3-yl)-2-nitrophenyl]phenylmethanone and potassium hydroxide.

Compound 5-2

[3,4-Dihydroxy-6-(5-methyl-[1,2,4]oxadiazol-3-yl)-2-nitro-phenyl]phenylmethanone Mono Sodium Salt $^1$H-NMR (DMSO-$d_6$) δ ppm: 2.38 (3H, s), 6.93 (1H, s), 7.34-7.41 (2H, m), 7.44-7.51 (1H, m), 7.62-7.68 (2H, m)

Compound 5-3

Methyl 3,4-dihydroxy-6-(5-methyl-[1,2,4]oxadiazol-3-yl)-2-nitrobenzoate Mono Potassium Salt $^1$H-NMR (DMSO-$d_6$) δ ppm: 2.56 (3H, s), 3.60 (3H, s), 6.72 (1H, s)

Compound 5-4

Methyl 3,4-dihydroxy-6-(5-methyl-[1,2,4]oxadiazol-3-yl)-2-nitrobenzoate Mono Sodium Salt $^1$H-NMR (DMSO-$d_6$) δ ppm: 2.56 (3H, s), 3.59 (3H, s), 6.68 (1H, s)

Compound 5-5

1-[3,4-Dihydroxy-6-(5-methyl-[1,2,4]oxadiazol-3-yl)-2-nitrophenyl]-2-methylpropan-1-one Mono Potassium Salt $^1$H-NMR (DMSO-$d_6$) δ ppm: 1.04 (6H, d, J=7.0 Hz), 2.55 (3H, s), 2.59-2.72 (1H, m), 6.84 (1H, s)

Compound 5-6

1-[3,4-Dihydroxy-6-(5-methyl-[1,2,4]oxadiazol-3-yl)-2-nitrophenyl]-2-methylpropan-1-one Mono Sodium Salt $^1$H-NMR (DMSO-$d_6$) δ ppm: 1.03 (6H, d, J=6.8 Hz), 2.55 (3H, s), 2.59-2.70 (1H, m), 6.81 (1H, s)

Test Example 1

Human COMT Inhibitory Potency

1) Preparation of Recombinant Human COMT
(1) Preparation of Recombinant Human Catechol-O-methyl Transferase According to the DNA sequence of NCBI (National Center for Biotechnology Information) accession number (BC011935), two oligonucleotide primers were designed to amplify the target DNA sequence coding full-length human catechol-O-methyl transferase (hereinafter referred to as "COMT") as shown in Sequence ID No. 1. Sequences of the 5'-primer and the 3'-primer were indicated in Sequence ID No. 3 and 4, respectively. For ease in insertion of corresponding PCR product into the desired vector, these primers includes restriction enzyme sites of BamH I and EcoR I on the 5'-side and the 3'-side, respectively.

Each of the 5'-primer indicated in Sequence ID No. 3 and the 3'-primer indicated in Sequence ID No. 4 was diluted with TE buffer to prepare 15 pmol/μL solutions. A mixture for PCR reaction was prepared with H$_2$O (for PCR, 34.8 μL), 25 mmol/L MgSO$_4$ (2.0 μL), 2 mmol/L dNTPs (5.0 μL) and 10-fold concentrated buffer for KOD plus DNA Polymerase (5.0 μL, TOYOBO). After the addition of each primer pairs (1 μL, 15 μmol) following human liver cDNA (5.0 μL, Clontech), 1.0 μL KOD plus (TOYOBO) was added to the above reaction mixture. Thereafter, PCR reaction was executed as referred to hereinafter; after the procedure at 94° C. for 2 minutes, PCR reactions were carried out for 40 cycles, each consisting of 94° C. for 15 seconds, 59° C. for 30 seconds, and 68° C. for 1 minutes and then terminated at 68° C. for 5 minutes and at 4° C. for 10 minutes.

PCR product was purified using a QIAquick PCR Purification Kit (QIAGEN) and the desired DNA insert was eluted using EB buffer (30 μL) included in the corresponding kit.
(2) Double Digestion of Recombinant Human COMT DNA Insert and pGEX-2T Vector The obtained recombinant human COMT DNA insert (1.5 μg) was mixed with 10-fold concentrated EcoR I buffer (3.0 μL, New England Biolab), H$_2$O (11.1 μL), BamH I (1.5 μL, 15 U, 10 U/μL) and EcoR I (1.0 μL, 15 U, 10 U/μL) and then incubated at 37° C. for 1.5 hours. Thereafter 10-fold concentrated loading buffer was added to the mixture. Following the purification on an electrophoresis, a piece of the gel region including objective digested fragment was removed and purified with a MinElute Gel Extraction Kit (QIAGEN). Double digestion and purification of pGEX-2T vector DNA (1.5 μg, Amersham) was also performed in a similar way as described above.
(3) Ligation and E. coli JM109 Transformation Double-digested DNA of pGEX-2T vector (2.0 μL, 50 ng) and insert DNA (1.24 μL, 33.4 ng) were added to 2-fold concentrated ligation buffer (3.24 μL, Promega) and mixed. The mixture was incubated at 25° C. for 1 hour following the addition of T4 ligase (1.0 μL, 3 U/μL, Promega). This solution of ligase-treated mixture (5 μL) was transferred to E. coli JM109 (100 μL) thawed at 0° C., and was gently mixed and incubated at 0° C. for 30 minutes. The mixture was heat-shocked at 42° C. for 40 seconds, without excessive shaking, followed by cooling at 0° C. for 10 minutes. After heat shock step, SOC medium (450 μL) was added and the mixture was shaken at 37° C. for 1 hour. Each aliquot (50 μL and 200 μL) of the mixture was subsequently seeded onto LB plates (a diameter of 9 cm, ampicillin 100 μg/mL) and statically cultured at 37° C. for 16 hours. As a result, colonies were observed on the plates.
(4) Colony Selection of JM109 Transformed with GST-Fusion Recombinant Human COMT Plasmid Some colonies were selected from above-mentioned statically cultured plates and each colony was inoculated into 2 mL of LB-ampicillin (100 μg/mL) liquid medium using sterile picks. After the shaking culture at 37° C. for 16 hours, aliquots (200 μL) of each culture were removed into 1.5 mL microtubes and plasmids were extracted by a phenol extraction. The obtained plasmids were resolubilized in TE buffer and separated by electrophoresis. Primary positive colonies were identified according to the electrophoretic mobilities of their extracted plasmids similar to that of pGEX-2T vector without insert DNA and reconfirmed by double digestion using restriction enzymes as follows.

DNA solutions (7 μL) prepared from primary positive colonies indicated above were mixed with 10-fold concentrated EcoR I buffer (0.9 μL, New England Biolab), then BamH I (0.5 μL, 10 U/μL) and EcoR I (0.5 μL, 15 U/μL) were added to the mixture. The solution was analyzed by electrophoresis after warming (37° C., 1 hour). Secondary positive colonies were identified as those with a band of about 670 bp.

(5) Extraction and Purification of GST-Fusion Recombinant Human COMT Plasmid from *E. coli* JM109

An aliquot (100 μL) from the culture of *E. coli* JM109 transformed with GST-fusion recombinant human COMT plasmid, which determined as a secondary positive colony at (4), was stored as a glycerol stock, whereas the rest was centrifuged at 12,000 rpm for 10 minutes to obtain *E. coli* pellet. Plasmid DNA was purified from the *E. coli* pellet by QIAGEN Plasmid mini kit (QIAGEN) and its concentration was determined by OD 260 nm (247 ng/μL). DNA sequence analysis according to a conventional method confirmed that the DNA sequence indicated in Sequence ID No. 2 was properly inserted at the desired site.

(6) Transformation of Competent *E. Coli* BL21 (DE3) CODON PLUS RP by GST-Fusion Recombinant Human COMT Plasmid DNA For transformation and plate culture in the same fashion as (3), 1 μL of purified GST-fusion recombinant human COMT plasmid DNA (1 ng/μL) with valid sequence indicated in (5) was added to 50 μl of cell suspension of competent *E. Coli* BL21 (DE3) CODON PLUS RP thawed at 0° C.

(7) Expression of GST-Fusion Recombinant Human COMT

A colony was picked up from the plate with transformed *E. Coli* BL21 (DE3) CODON PLUS RP and cultured with shaking at 37° C. for 15 hours in 5 mL of LB-ampicillin (100 μg/mL) liquid medium. An aliquot of culture medium (50 μL) was stored at −80° C. as a glycerol stock. A piece of the glycerol stock was used to inoculate into 150 mL of LB-ampicillin (100 μg/mL) medium and cultured with shaking at 37° C. for 16 hours. The culture was diluted into 7 culture flasks with LB-ampicillin (100 μg/mL) medium (500 mL each), and then each culture was grown at 20° C. for 4.5 hours with shaking to a cell density of OD 600 nm=0.44, at which point 50 μL of isopropyl-β-D-thiogalactopyranoside (1 mol/L) was added to each culture. After that, each culture was incubated under the same conditions for an additional 18 hours. *E. coli* pellet was harvested by centrifugation for 20 minutes at 9,000 rpm, divided into four equal portions (4 g) and stored at −80° C. until use.

(8) Thrombin Processing of GST-Fusion Recombinant Human COMT

*E. coli* pellet obtained in (7) was suspended in BugBuster Reagent (Novagen, 40 mL) containing Bensonase (Novagen, 30 μL) and rLysozyme (Novagen, 1 μL) and the *E. coli* treated with a gentle rotation at room temperature for 15 minutes. The obtained cell lysate was separated by centrifugation at 12,000 rpm for 20 minutes at 4° C. and the supernatant was recovered. This supernatant was incubated at 4° C. for 1 hour on a rotating platform with a 20 mL of a 50% slurry of Glutathione Sepharose 4B (resin-bed volume of 10 mL), which was previously equilibrated with D-PBS (Dulbecco's phosphate-buffered saline). The resultant resin was separated on a filter from the filtrate and washed five times with 30 mL of D-PBS, followed by three additional washing steps with 30 mL of thrombin processing buffer (150 mmol/L NaCl, 50 mmol/L Tris-HCl pH8.0, 10% glycelol, 2.5 mmol/L $CaCl_2$, and 0.5% n-octyl-β-D-glucopyranoside). After the last wash, the resin was again suspended with thrombin processing buffer at a final volume of 30 mL. Thirty units of thrombin protease (Amersham Biosciences) was added to the resin suspension, and thrombin processing was allowed to proceed with a gentle rotation for 15 hours at 4° C. The resin suspension was filtrated and recombinant human COMT solution obtained as a filtrate was stored at −80° C. until assayed.

2) Measurement of Human COMT Inhibitory Potency

Measurement of human COMT inhibitory potency was performed according to the method of G. Zürcher et al (J. Neurochem., 1982, vol. 38, p. 191-195) with a minor modification. Aliquot (0.25 μL) of recombinant human COMT prepared in 1) (approximately 1 mg/mL) was preincubated with a test compound for 5 minutes at 37° C. in the reaction mixture, composed of 40 μL potassium phosphate buffer (500 mmol/L, pH7.6), 10 μL magnesium chloride (100 mmol/L), 10 μL dithiothreitol (62.5 mmol/L) and 0.5 adenosine deaminase (2550 units/mL). Control samples were prepared in the same way, but the test compounds were replaced with an equal volume (5 μL) of dimethyl sulfoxide. After the addition of 20 μL [$^3$H]-S-adenosyl-L-methionine (12.5 mmol/L, 1.2 Ci/mol; Amersham Biosciences), the reaction was started by the addition of 25 μL catechol substrate (7 mmol/L). The reaction mixture, final volume 0.25 mL, was incubated at 37° C. for 30 minutes. The reaction was then stopped by the addition of 0.25 mL of ice-cold 1 mol/L hydrochloric acid containing 0.1 g/L guaiacol. After the addition of 2.5 mL scintillator OPTI-FLUOR (registered mark) 0 (Packerd), and following 1-minute vigorous shaking, the radioactivity present in the organic phase was then directly counted in a liquid scintillation counter (Packard; TRICARB 1900CA). Blanks were incubated without catechol substrate (substrate was added after the termination of reaction). The $IC_{50}$ value indicates the molar concentration required to inhibit 50% of the enzyme activity. As comparative examples, tolcapone, entacapone and 5-(3-methyl-[1,2,4]oxadiazol-5-yl)-3-nitrobenzene-1,2-diol (comparative example 1), which is described in example 75 of the patent literature 1, were assayed in the similar fashion. These results were shown in Table 14.

TABLE 14

| Compound No. | $IC_{50}$ (nmol/L) |
|---|---|
| 1-1 | 9.4 |
| 1-3 | 8.1 |
| 1-5 | 9.3 |
| 1-9 | 7.7 |
| 1-20 | 8.7 |
| 1-22 | 8.3 |
| 1-24 | 7.6 |
| 1-37 | 4.7 |
| 1-40 | 8.8 |
| 1-41 | 4.7 |
| Tolcapone | 9.0 |
| Entacapone | 11.1 |
| Comparative example 1 | 13.2 |

Test Example 2

Rat Hepatocyte Toxicities

After rat cryopreserved hepatocytes $3 \times 10^{-6}$ cells/vial, stored at −150° C., was warmed at 37° C., and the hepatocytes were added into a thawing medium with glucose (10 mL) and agitated. The suspension was centrifuged at 1000 rpm for 1 minute. After the supernatant was removed, the cell pellet was suspended in Williams E medium (15 mL). A solution of drug in dimethyl sulfoxide was prepared at 45, 15, 4.5, 1.5, 0.45 mmol/L, then each of the drug solutions and dimethyl sulfoxide as a control was dispensed by 2.0 μL to a test tube. The above cell suspension (300 μL) was dispensed into the tube and re-suspended. Every 100 μL of each suspension was dispensed to a 96 well-plate, and the plate was incubated for 4 hours at 37° C. in $CO_2$ incubators. According to Cell viability assay provided from Promega Corporation, ATP activity was measured. The EC50 value indicates the concentration that shows 50% of the number of viable cells of control. These results were shown in Table 15.

TABLE 15

| Compound No. | EC$_{50}$(µmol/L) |
|---|---|
| 1-1 | 683 |
| 1-2 | 645 |
| 1-3 | 698 |
| 1-5 | >1000 |
| 1-9 | >1000 |
| 1-22 | 523 |
| 1-24 | >1000 |
| Tolcapone | 34.3 |
| Entacapone | 111 |
| Comparative example 1 | 172 |

These results suggest that the compounds of the present invention exhibited extremely minor hepatocyte toxicities as compared with tolcapone, entacapone and comparative example 1.

Test Example 3

Evaluation of Plasma L-Dopa Concentration (1) Compound Administration and Plasma Sampling 6-week-old male Sprague-Dawley rats weighing 170 g to 190 g (Charles River Laboratories Japan Inc.) were fasted overnight. A suspension of test compounds (0.6 mg/mL) and a mixed suspension of L-dopa (1 mg/mL) and carbidopa (6 mg/mL) were prepared with agate mortar using 0.5% methylcellulose solution as a medium. The mixed suspension of L-dopa (5 mg/kg) and carbidopa (30 mg/kg) was orally administrated either 4 or 6 hours after the oral administration of test compounds (3 mg/kg). Blood samples were obtained at 2 hours after the oral administration of mixed suspension of L-dopa and carbidopa and transferred to tubes containing sodium heparin, ethylene glycol tetraacetic acid and reduced glutathione on ice. Plasma sample for the determination of L-dopa concentration was obtained by centrifugation.

(2) Measurement of L-Dopa Concentration

To 0.05 mL of the plasma obtained in (1) described above, was added 0.01 mL of 100 µg/mL aqueous solution of metformin hydrochloride as an internal standard material according to a conventional method and then deproteinization was performed by adding 0.05 mL of 250 mmol/L ethylenediamine-tetraacetic acid disodium salt in 0.5 mol/L perchloric acid solution. After centrifugation, 0.002 mL of its supernatant was injected into LC-MS/MS. Plasma concentration of L-dopa was measured by LC-MS/MS under the condition mentioned below. L-dopa concentration was shown in Table 16 as a percentage of the L-dopa concentration of control group without any test compound administration.

LC

Instrument: Agilent1100

Column: Capcellpak C18 MGIII 5 µm 4.6×50 mm

Mobile phase: 0.5% aqueous solution of heptafluorobutyric acid/acetonitrile

Column temperature: 40° C.

Flow rate: 0.5 mL/minute

MS/MS

Instrument: API-4000

Ionization method: ESI (Turbo Ion Spray)

TABLE 16

| | Plasma L-dopa (%) | |
|---|---|---|
| Compound No. | 4 hour | 6 hour |
| 1-1 | 182.9 ± 5.0 | 189.2 ± 32.8 |
| Comparative example 1 | 143.3 ± 13.3 | 106.9 ± 18.2 |

The results clearly shows that the increase in plasma L-dopa concentration was more sustained when the compound of the present invention was co-administrated with L-dopa and carbidopa as compared to that when the comparative example 1 was co-administrated with L-dopa and carbidopa.

Test Example 4

The Potentiation on the Effecacy of L-DOPA in Unilateral 6-Hydroxydopamine-Lesioned Hemi-Parkinsonian Rats (1) Drugs The following compounds were used: 6-hydroxydopamine hydrochloride (6-OHDA, Sigma); desipramine hydrochloride (desipramine, Sigma); L-ascorbic acid (Sigma); sodium pentobarbital (Nembutal inj., Dainippon Sumitomo Pharma Co., Ltd); apomorphine hydrochloride hemihydrate (apomorphine, Sigma); 3,4-dihydroxyphenylalanine (L-dopa, Sigma); carbidopa monohydrate (carbidopa, Kemprotec Ltd.); 0.5% methylcellulose (Wako Pure Chemicals).

6-OHDA was dissolved at 2 mg/ml in a saline solution containing 0.2% L-ascorbic acid. Desipramine was dissolved at 10 mg/mL in distilled water in a hot-water bath. Apomorphine was dissolved at 0.1 mg/mL in a saline solution. L-dopa/carbidopa was suspended in a 0.5% methylcellulose solution. Test compounds were dissolved in a solution containing 0.5% dimethylsulfoxide, 20% polyethylene glycol and 79.5% of a 0.1 mol/L aqueous solution of arginine.

(2) Preparation of 6-OHDA-Lesioned Model

Preparation of 6-OHDA-lesioned model was performed according to the method of nonpatent literature 6 with a minor modification. Male Sprague-Dawley rats (6-weeks-old, Charles River Laboratories Japan Inc.) were anaesthetized with intraperitoneal sodium pentobarbital (45 mg/kg) administration and placed in a stereotaxic frame (Narishige, Tokyo, Japan). In order to prevent 6-OHDA-induced damage of noradrenergic neurons, intraperitoneal desipramine injection (25 mg/kg) was given 30 minutes before the 6-OHDA injection. After the bregma identification via a middle calvarial incision, the skull was drilled using a dental drill at the site of 6-OHDA injection. The lesion was made by injecting 6-OHDA (8 µg in 4 µL at a speed of 1 µL/minute) unilaterally into the left medial forebrain bundle (the lesion coordinates; A/P −2.5 mm, L/M −1.8 mm, and V/D −8.0 mm, from the bregma point and surface of the skull) by using a injection cannula (30 gauge needle) connected to a microsyringe (Hamilton). The cannula was carefully removed from the animal after keeping placed on the lesion site for 5 minutes. The skull was filled its hole with dental cement, disinfected, and the scalp incision was surgically sutured. Animals recovered from anesthesia were housed as usual until the day of the experiment.

(3) Evaluation of Turning Behavior

Three weeks after the lesion, rats were tested on the basis of their contralateral rotation (single rotation was defined as a 360° turn) in response to 0.1 mg/kg apomorphine given subcutaneously. For behavioral observation, rats were placed in plastic cylinders of radius 20 cm and turning behavior was videotaped and quantified by rat-rotation auto counting system R-RACS (Kissei Wellcom Co., Ltd.). Animals that turned over 100 rotation counts during 1 hour were accepted for further experiments. On the experimental day, animals were fasted for 10 hours from 9 am, and all test compounds were orally given at doses of 10 mg/kg with concomitant oral administration of 5 mg/kg L-dopa and 30 mg/kg carbidopa. The drug potency was measured as the number of contralateral turning, and duration of the response was defined as a time period until the animal exhibited less than 10 rotation counts per 10 minutes for more than 60 minutes period. Total counts and the duration of the response were listed in Table 17. Similarly, the result of the control group that was treated only with L-dopa and carbidopa was shown in the same table.

TABLE 17

| Compound No. | Duration (minutes) | Total counts |
| --- | --- | --- |
| Control | 133.8 | 611.9 |
| 1-1 | 293.8 | 2060.8 |
| 1-2 | 312.5 | 2103.0 |
| 1-5 | 321.3 | 2051.9 |
| 1-14 | 275.0 | 1678.4 |

From these results, as compared with control animals which were treated only with L-dopa/carbidopa, remarkable potentiation of drug effects were observed in animals administered with compounds of the present invention in combination with L-dopa/carbidopa.

INDUSTRIAL APPLICABILITY

Compounds of the present invention exhibit potent COMT inhibitory activities, and are accordingly useful for treating or preventing Parkinson's disease, depression or hypertension. Especially, compounds of the present invention are useful for treating or preventing Parkinson's disease since use of compounds of the present invention in combination with L-dopa increases the bioavailability of L-dopa remarkably.

Sequence Listing Free Text

[SEQ ID No. 1]
Sequence ID No. 1 indicates the sequence of recombinant human catechol-O-methyl transferase.

[SEQ ID No. 2]
Sequence ID No. 2 indicates the DNA sequence, which was intended to express the recombinant human catechol-O-methyl transferase shown in sequence ID No. 1, amplified by using primer pair shown in sequence ID No. 3 and 4.

[SEQ ID No. 3]
Sequence ID No. 3 indicates the sequence of 5'-primer employed to amplify the DNA sequence shown in sequence ID No. 2.

[SEQ ID No. 4]
SEQ ID No. 4 indicates the sequence of 3'-primer employed to amplify the DNA sequence shown in sequence ID No. 2.

The invention claimed is:
1. A compound represented by general formula (I):
or a pharmaceutically acceptable salt thereof,

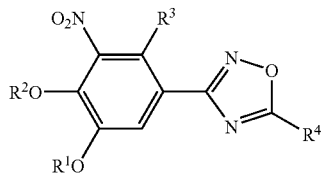

wherein
$R^1$ and $R^2$ are each independently a hydrogen atom, a lower acyl group, a lower alkoxycarbonyl group, an aralkylcarbonyl group or —C(O)NR$^{11}$R$^{12}$, or $R^1$ and $R^2$ are joined together to form —C(O)— or a lower alkylene group;
$R^3$ is:
a) a halo-lower alkyl group,
b) a lower acyl group,
c) a halo-lower alkylcarbonyl group,
d) a cycloalkylcarbonyl group,
e) an arylcarbonyl group, wherein the ring of the arylcarbonyl group is unsubstituted or substituted with 1 to 5 substituents selected from the group consisting of a halogen atom, a lower alkyl group, a halo-lower alkyl group, a lower alkoxy group, a cycloalkyl-lower alkoxy group, a hydroxy group, a lower alkoxycarbonyl group, —C(O)NR$^{11}$R$^{12}$ and a cyano group,
f) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
g) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
h) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
i) a lower alkoxycarbonyl group,
j) a cycloalkyloxycarbonyl group,
k) a lower alkoxy-lower alkoxycarbonyl group,
l) a carboxy group,
m) a cyano group,
n) —C(O)NR$^{11}$R$^{12}$,
o) —C(O)C(O)NR$^{11}$R$^{12}$,
p) a lower alkylsulfonyl group,
q) —SO$_2$NR$^{11}$R$^{12}$ or
r) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group;
$R^4$ is:
a) a lower alkyl group,
b) a halo-lower alkyl group,
c) a cycloalkyl group,
d) a heterocycloalkyl group,
e) a lower alkoxy-lower alkyl group,
f) an aryloxy-lower alkyl group,
g) a lower alkoxycarbonyl-lower alkyl group or
h) a hydroxy-lower alkyl group; and
$R^{11}$ and $R^{12}$ are each independently a hydrogen atom, a lower alkyl group, a cycloalkyl group, a bridged cyclic hydrocarbon group, a phenyl group or an aralkyl group, or $R^{11}$ and $R^{12}$, together with the nitrogen atom to which they are bonded, form a cyclic amino group.

2. The compound according to claim 1, or a pharmaceutically acceptable salt thereof, wherein
$R^1$ and $R^2$ are each independently a hydrogen atom, a lower acyl group, a lower alkoxycarbonyl group or —C(O)NR$^{11}$R$^{12}$, or $R^1$ and $R^2$ are joined together to form —C(O)—;
$R^3$ is:
a) a halo-lower alkyl group,
b) a lower acyl group,
c) a halo-lower alkylcarbonyl group,
d) a cycloalkylcarbonyl group,
e) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
f) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
g) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
h) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
i) a lower alkoxycarbonyl group,
j) a cycloalkyloxycarbonyl group,
k) a lower alkoxy-lower alkoxycarbonyl group,
l) a carboxy group,
m) a cyano group,
n) —C(O)NR$^{11}$R$^{12}$,
o) —C(O)C(O)NR$^{11}$R$^{12}$,
p) a lower alkylsulfonyl group,
q) —SO$_2$NR$^{11}$R$^{12}$ or
r) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group;
$R^4$ is:
a) a lower alkyl group,
b) a halo-lower alkyl group,
c) a cycloalkyl group,
d) a heterocycloalkyl group,
e) a lower alkoxy-lower alkyl group,
f) an aryloxy-lower alkyl group or
g) a lower alkoxycarbonyl-lower alkyl group; and
$R^{11}$ and $R^{12}$ are each independently a hydrogen atom, a lower alkyl group, a cycloalkyl group, a bridged cyclic hydrocarbon group, a phenyl group or an aralkyl group, or R¹¹ and R¹², together with the nitrogen atom to which they are bonded, form a cyclic amino group.

3. The compound according to claim 2, or a pharmaceutically acceptable salt thereof, wherein R¹ and R² are a hydrogen atom.

4. The compound according to claim 3, or a pharmaceutically acceptable salt thereof, wherein R³ is:
   a) a lower acyl group,
   b) a halo-lower alkylcarbonyl group,
   c) a cycloalkylcarbonyl group,
   d) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
   e) a heteroarylcarbonyl group, wherein the ring of the heteroarylcarbonyl group is unsubstituted or substituted with 1 to 3 substituents selected from the group consisting of a halogen atom, a lower alkyl group, a halo-lower alkyl group and a lower alkoxy group,
   f) an aralkylcarbonyl group, wherein the ring of the aralkylcarbonyl group is unsubstituted or substituted with 1 to 5 substituents selected from the group consisting of a halogen atom, a lower alkyl group, a halo-lower alkyl group and a lower alkoxy group,
   g) an aryloxy-lower alkylcarbonyl group, wherein the ring of the aryloxy-lower alkylcarbonyl group is unsubstituted or substituted with 1 to 5 substituents selected from the group consisting of a halogen atom, a lower alkyl group, a halo-lower alkyl group and a lower alkoxy group,
   h) a lower alkoxycarbonyl group,
   i) a cycloalkyloxycarbonyl group,
   j) a lower alkoxy-lower alkoxycarbonyl group,
   k) —C(O)C(O)NR¹¹R¹² or
   l) a heteroaryl group, wherein the ring of the heteroaryl group is unsubstituted or substituted with 1 to 3 substituents selected from the group consisting of a halogen atom, a lower alkyl group, a halo-lower alkyl group and a lower alkoxy group.

5. The compound according to claim 4, or a pharmaceutically acceptable salt thereof, wherein R⁴ is:
   a) a lower alkyl group,
   b) a cycloalkyl group,
   c) a lower alkoxy-lower alkyl group or
   d) a lower alkoxycarbonyl-lower alkyl group.

6. The compound according to claim 5, or a pharmaceutically acceptable salt thereof, wherein R³ is:
   a) a lower acyl group,
   b) a cycloalkylcarbonyl group,
   c) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
   d) a lower alkoxycarbonyl group,
   e) a cycloalkyloxycarbonyl group,
   f) a lower alkoxy-lower alkoxycarbonyl group or
   g) —C(O)C(O)NR¹¹R¹².

7. The compound according to claim 5, or a pharmaceutically acceptable salt thereof, wherein R³ is:
   a) a lower acyl group,
   b) a cycloalkylcarbonyl group,
   c) an arylcarbonyl group, wherein the ring of the arylcarbonyl group is unsubstituted or substituted with 1 to 5 substituents selected from the group consisting of a halogen atom, a lower alkyl group, a halo-lower alkyl group and a lower alkoxy group,
   d) a lower alkoxycarbonyl group or
   e) —C(O)C(O)NR¹¹R¹².

8. A compound, or a pharmaceutically acceptable salt thereof, selected from the group consisting of:
   [3,4-dihydroxy-6-(5-methyl-[1,2,4]oxadiazol-3-yl)-2-nitrophenyl]phenylmethanone;
   1-[3,4-dihydroxy-6-(5-methyl-[1,2,4]oxadiazol-3-yl)-2-nitrophenyl]ethanone;
   methyl 3,4-dihydroxy-6-(5-methyl-[1,2,4]oxadiazol-3-yl)-2-nitrobenzoate;
   N-cyclohexyl-2-[3,4-dihydroxy-6-(5-methyl-[1,2,4]oxadiazol-3-yl)-2-nitrophenyl]-2-oxoacetamide;
   N-cyclohexyl-2-[3,4-dihydroxy-6-(5-methyl-[1,2,4]oxadiazol-3-yl)-2-nitrophenyl]-N-methyl-2-oxoacetamide;
   1-{6-[5-(2-ethoxyethyl)-[1,2,4]oxadiazol-3-yl]-3,4-dihydroxy-2-nitrophenyl}ethanone; and
   cyclohexyl-[3,4-dihydroxy-6-(5-methyl-[1,2,4]oxa-diazol-3-yl)-2-nitrophenyl]methanone.

9. A pharmaceutical composition which comprises, as an active ingredient, a compound according to claim 1 or a pharmaceutically acceptable salt thereof.

10. A pharmaceutical combination comprising a compound according to claim 1 or a pharmaceutically acceptable salt thereof and at least one selected from L-dopa or an aromatic L-amino acid decarboxylase inhibitor.

* * * * *

```
                        SEQUENCE LISTING

<160> NUMBER OF SEQ ID NOS: 4

<210> SEQ ID NO 1
<211> LENGTH: 223
<212> TYPE: PRT
<213> ORGANISM: Homo sapiens

<400> SEQUENCE: 1

Gly Ser Met Gly Asp Thr Lys Glu Gln Arg Ile Leu Asn His Val Leu
1               5                   10                  15

Gln His Ala Glu Pro Gly Asn Ala Gln Ser Val Leu Glu Ala Ile Asp
            20                  25                  30

Thr Tyr Cys Glu Gln Lys Glu Trp Ala Met Asn Val Gly Asp Lys Lys
        35                  40                  45

Gly Lys Ile Val Asp Ala Val Ile Gln Glu His Gln Pro Ser Val Leu
    50                  55                  60

Leu Glu Leu Gly Ala Tyr Cys Gly Tyr Ser Ala Val Arg Met Ala Arg
65                  70                  75                  80

Leu Leu Ser Pro Gly Ala Arg Leu Ile Thr Ile Glu Ile Asn Pro Asp
                85                  90                  95

Cys Ala Ala Ile Thr Gln Arg Met Val Asp Phe Ala Gly Val Lys Asp
            100                 105                 110

Lys Val Thr Leu Val Val Gly Ala Ser Gln Asp Ile Ile Pro Gln Leu
        115                 120                 125

Lys Lys Lys Tyr Asp Val Asp Thr Leu Asp Met Val Phe Leu Asp His
    130                 135                 140

Trp Lys Asp Arg Tyr Leu Pro Asp Thr Leu Leu Leu Glu Glu Cys Gly
145                 150                 155                 160
```

```
Leu Leu Arg Lys Gly Thr Val Leu Leu Ala Asp Asn Val Ile Cys Pro
            165                 170                 175

Gly Ala Pro Asp Phe Leu Ala His Val Arg Gly Ser Ser Cys Phe Glu
        180                 185                 190

Cys Thr His Tyr Gln Ser Phe Leu Glu Tyr Arg Glu Val Val Asp Gly
    195                 200                 205

Leu Glu Lys Ala Ile Tyr Lys Gly Pro Gly Ser Glu Ala Gly Pro
        210                 215                 220

<210> SEQ ID NO 2
<211> LENGTH: 684
<212> TYPE: DNA
<213> ORGANISM: Artificial
<220> FEATURE:
<223> OTHER INFORMATION: insert DNA

<400> SEQUENCE: 2
tctggatcca tgggtgacac caaggagcag cgcatcctga accacgtgct gcagcatgcg      60
gagcccggga acgcacagag cgtgctggag gccattgaca cctactgcga gcagaaggag     120
tgggccatga acgtgggcga caagaaaggc aagatcgtgg acgccgtgat tcaggagcac     180 cagcccctccg tgctgctgga gctgggggcc tactgtggct actcagctgt gcgcatggcc     240
cgcctgctgt caccaggggc gaggctgatc accatcgaga tcaaccccga ctgtgccgcc     300
atcacccagc ggatggtgga tttcgctggc gtgaaggaca aggtcaccct tgtggttgga     360
gcgtcccagg acatcatccc ccagctgaag aagaagtatg atgtggacac actggacatg     420
gtcttcctcg accactggaa ggaccggtac ctgccggaca cgcttctctt ggaggaatgt     480
ggcctgctgc ggaaggggac agtgctactg gctgacaacg tgatctgccc aggtgcgcca     540
gacttcctag cacacgtgcg cgggagcagc tgctttgagt gcacacacta ccaatcgttc     600
ctggaataca gggaggtggt ggacggcctg gagaaggcca tctacaaggg cccaggcagc     660
gaagcagggc cctgagaatt ctct                                            684

<210> SEQ ID NO 3
<211> LENGTH: 27
<212> TYPE: DNA
<213> ORGANISM: Artificial
<220> FEATURE:
<223> OTHER INFORMATION: 5'-primer

<400> SEQUENCE: 3
tctggatcca tgggtgacac caaggag                                         27

<210> SEQ ID NO 4
<211> LENGTH: 28
<212> TYPE: DNA
<213> ORGANISM: Artificial
<220> FEATURE:
<223> OTHER INFORMATION: 3'-primer

<400> SEQUENCE: 4
agagaattct cagggccctg cttcgctg                                        28
```